(12) United States Patent
Carlson et al.

(10) Patent No.: US 12,007,382 B2
(45) Date of Patent: Jun. 11, 2024

(54) SYSTEMS, METHODS AND APPARATUS FOR SEPARATING COMPONENTS OF A SAMPLE

(71) Applicant: Crown Laboratories, Inc., Johnson City, TN (US)

(72) Inventors: Scott Carlson, Dallas, TX (US); John Tepper, Carrollton, TX (US)

(73) Assignee: Crown Laboratories, Inc., Johnson City, TN (US)

(*) Notice: Subject to any disclaimer, the term of this patent is extended or adjusted under 35 U.S.C. 154(b) by 250 days.

(21) Appl. No.: 17/085,043

(22) Filed: Oct. 30, 2020

(65) Prior Publication Data

US 2021/0132036 A1    May 6, 2021

Related U.S. Application Data

(60) Provisional application No. 62/928,584, filed on Oct. 31, 2019.

(51) Int. Cl.
*A61M 1/02* (2006.01)
*G01N 1/10* (2006.01)
(Continued)

(52) U.S. Cl.
CPC ......... *G01N 33/48785* (2013.01); *G01N 1/10* (2013.01); *B04B 5/0414* (2013.01); *G01N 2001/1006* (2013.01); *G01N 33/80* (2013.01)

(58) Field of Classification Search
CPC .... G01N 33/48785; G01N 1/10; G01N 33/80; G01N 2001/1006; G01N 33/491; B04B 5/0414; A61M 1/029; A61M 2202/0415
(Continued)

(56) References Cited

U.S. PATENT DOCUMENTS

| 10,618 A | 3/1854 | Wright |
|---|---|---|
| 1,543,846 A | 6/1925 | Hansen |

(Continued)

FOREIGN PATENT DOCUMENTS

| CA | 2181462 C | 8/2002 |
|---|---|---|
| CH | 696752 A5 | 11/2007 |

(Continued)

OTHER PUBLICATIONS

Landi A, Tarantino R, Marotta N, Ruggeri AG, Domenicucci M, Giudice L, Martini S, Rastelli M, Ferrazza G, De Luca N, Tomei G, Delfini R. The use of platelet gel in postero-lateral fusion: preliminary results in a series of 14 cases. Eur Spine J. May 2011;20 Suppl 1(Suppl 1):S61-7. Epub Mar. 17, 2011. PMID: 21416280.

(Continued)

*Primary Examiner* — Robert R Raevis
(74) *Attorney, Agent, or Firm* — KDW FIRM PLLC

(57) ABSTRACT

Described herein are methods, systems, and apparatus for separating components of a sample; as well as methods of using compositions prepared by same. In one aspect, the apparatus can comprise a tubular body for receiving sample, a thixotropic material, and a float. The system comprising the apparatus can be configured to separate the component of the sample using centrifugation. The float can have a specific gravity less than or equal to the specific gravity of the thixotropic material. The thixotropic material can be positioned along a bottom inner surface of the tubular body, and a portion of the float can be embedded in the thixotropic material. The float can be made of a single, integral piece or a plurality of pieces that are configured to be fixed and immobile relative to each other during centrifugation. The float can be solid, nonporous and without any aperture.

57 Claims, 13 Drawing Sheets

(51) Int. Cl.
*G01N 33/487* (2006.01)
*B04B 5/04* (2006.01)
*G01N 33/80* (2006.01)

(58) Field of Classification Search
USPC ...... 73/64.56, 863, 863.21; 210/782, 360.01, 210/512.1
See application file for complete search history.

(56) References Cited

U.S. PATENT DOCUMENTS

| | | |
|---|---|---|
| 2,796,558 A | 6/1957 | Koehler |
| 3,774,454 A | 11/1973 | Shaw |
| 3,814,248 A | 6/1974 | Lawhead |
| 3,852,194 A | 12/1974 | Zine |
| 3,909,419 A | 9/1975 | Ayres |
| 3,929,646 A | 12/1975 | Adler |
| 3,957,654 A | 5/1976 | Ayres |
| 3,981,804 A | 9/1976 | Gigliello |
| 4,055,501 A | 10/1977 | Cornell |
| 4,101,422 A | 7/1978 | Lamont et al. |
| 4,148,764 A | 4/1979 | Lamont et al. |
| 4,190,535 A | 2/1980 | Luderer et al. |
| 4,267,269 A | 5/1981 | Grode et al. |
| 4,350,593 A | 9/1982 | Kessler |
| 4,417,981 A * | 11/1983 | Nugent ............... B01L 3/50215 422/918 |
| 4,567,754 A | 2/1986 | Wardlaw et al. |
| 4,599,219 A | 7/1986 | Cooper et al. |
| 4,752,449 A | 6/1988 | Jackson et al. |
| 4,784,990 A | 11/1988 | Nimrod et al. |
| 4,917,801 A | 4/1990 | Luderer et al. |
| 4,946,601 A | 8/1990 | Fiehler |
| 4,954,264 A | 9/1990 | Smith |
| 5,065,768 A | 11/1991 | Coleman et al. |
| 5,086,784 A | 2/1992 | Levine et al. |
| 5,174,961 A | 12/1992 | Smith |
| 5,236,604 A | 8/1993 | Fiehler |
| 5,252,557 A | 10/1993 | Kita et al. |
| 5,393,674 A | 2/1995 | Levine et al. |
| 5,462,752 A | 10/1995 | Chao et al. |
| 5,494,590 A | 2/1996 | Smith et al. |
| 5,510,102 A | 4/1996 | Cochrum |
| 5,510,237 A | 4/1996 | Isogawa et al. |
| 5,560,830 A | 10/1996 | Coleman et al. |
| 5,583,114 A | 12/1996 | Barrows et al. |
| 5,585,007 A | 12/1996 | Antanavich et al. |
| 5,589,167 A | 12/1996 | Cleland et al. |
| 5,667,963 A | 9/1997 | Smith et al. |
| 5,707,876 A | 1/1998 | Levine |
| 5,733,545 A | 3/1998 | Hood, III |
| 5,791,352 A | 8/1998 | Reich et al. |
| 5,891,617 A | 4/1999 | Watson et al. |
| 5,906,744 A | 5/1999 | Carroll et al. |
| 5,977,056 A | 11/1999 | Powell-Jones et al. |
| 6,054,122 A | 4/2000 | MacPhee et al. |
| 6,071,422 A | 6/2000 | Hlavinka et al. |
| 6,117,425 A | 9/2000 | MacPhee et al. |
| 6,123,655 A | 9/2000 | Fell |
| 6,197,325 B1 | 3/2001 | MacPhee et al. |
| 6,390,966 B2 | 5/2002 | Anderson |
| 6,398,972 B1 | 6/2002 | Blasetti et al. |
| 6,428,527 B1 | 8/2002 | Jones et al. |
| 6,465,256 B1 | 10/2002 | Iskra |
| 6,472,162 B1 | 10/2002 | Coelho et al. |
| 6,559,119 B1 | 5/2003 | Burgess et al. |
| 7,074,577 B2 | 7/2006 | Haubert et al. |
| 7,077,273 B2 | 7/2006 | Ellsworth et al. |
| 7,094,464 B2 | 8/2006 | Mao et al. |
| 7,112,342 B2 | 9/2006 | Worden |
| 7,153,477 B2 | 12/2006 | DiCesare et al. |
| 7,179,391 B2 | 2/2007 | Leach et al. |
| 7,223,346 B2 | 5/2007 | Dorian et al. |
| 7,329,534 B2 | 2/2008 | Haubert et al. |
| 7,358,095 B2 | 4/2008 | Haubert et al. |
| 7,374,678 B2 | 5/2008 | Leach et al. |
| 7,445,125 B2 | 11/2008 | Ellsworth et al. |
| 7,470,371 B2 | 12/2008 | Dorian et al. |
| 7,771,590 B2 | 8/2010 | Leach et al. |
| 7,780,860 B2 | 8/2010 | Higgins et al. |
| 7,837,884 B2 | 11/2010 | Dorian et al. |
| 7,845,499 B2 | 12/2010 | Higgins et al. |
| 7,915,029 B2 | 3/2011 | Haubert et al. |
| 7,947,236 B2 | 5/2011 | Losada et al. |
| 7,992,725 B2 | 8/2011 | Leach et al. |
| 8,012,742 B2 | 9/2011 | Haubert et al. |
| 8,048,297 B2 | 11/2011 | Leach et al. |
| 8,048,321 B2 | 11/2011 | Leach et al. |
| 8,119,013 B2 | 2/2012 | Leach et al. |
| 8,177,072 B2 | 5/2012 | Chapman et al. |
| 8,187,477 B2 | 5/2012 | Dorian et al. |
| 8,236,258 B2 | 8/2012 | Leach et al. |
| 8,282,839 B2 | 10/2012 | Ellsworth |
| 8,328,024 B2 | 12/2012 | Leach et al. |
| 8,348,066 B2 | 1/2013 | Ellsworth |
| 8,377,395 B2 | 2/2013 | Coleman |
| 8,394,342 B2 | 3/2013 | Felix et al. |
| 8,445,264 B2 | 5/2013 | Seubert et al. |
| 8,474,630 B2 | 7/2013 | Dorian et al. |
| 8,506,823 B2 | 8/2013 | Chapman et al. |
| 8,511,479 B2 | 8/2013 | Chapman et al. |
| 8,511,480 B2 | 8/2013 | Chapman et al. |
| 8,518,272 B2 | 8/2013 | Hoeppner |
| 8,529,957 B2 * | 9/2013 | Turzi ................... A61L 24/106 424/530 |
| 8,596,470 B2 | 12/2013 | Leach et al. |
| 8,603,345 B2 | 12/2013 | Ross et al. |
| 8,603,346 B2 | 12/2013 | Leach et al. |
| 8,632,736 B2 | 1/2014 | Spatafore et al. |
| 8,632,740 B2 | 1/2014 | Dastane et al. |
| 8,747,781 B2 | 6/2014 | Bartfeld et al. |
| 8,794,452 B2 | 8/2014 | Crawford et al. |
| 8,808,551 B2 | 8/2014 | Leach et al. |
| 8,945,537 B2 | 2/2015 | Turzi |
| 8,950,586 B2 | 2/2015 | Dorian et al. |
| 8,992,862 B2 | 3/2015 | Leach et al. |
| 8,998,000 B2 | 4/2015 | Crawford et al. |
| 9,011,800 B2 | 4/2015 | Leach et al. |
| 9,079,123 B2 | 7/2015 | Crawford et al. |
| 9,095,849 B2 | 8/2015 | Losada et al. |
| 9,114,334 B2 | 8/2015 | Leach et al. |
| 9,120,095 B2 | 9/2015 | O'Connell |
| 9,138,664 B2 | 9/2015 | Leach et al. |
| 9,162,232 B2 | 10/2015 | Ellsworth |
| 9,239,276 B2 | 1/2016 | Landrigan et al. |
| 9,272,083 B2 | 3/2016 | Duffy et al. |
| 9,333,445 B2 | 5/2016 | Battles et al. |
| 9,339,741 B2 | 5/2016 | Newby et al. |
| 9,364,828 B2 | 6/2016 | Crawford et al. |
| 9,375,661 B2 | 6/2016 | Chapman et al. |
| 9,393,575 B2 | 7/2016 | Ellsworth et al. |
| 9,393,576 B2 | 7/2016 | Ellsworth et al. |
| 9,399,226 B2 | 7/2016 | Ellsworth et al. |
| 9,452,427 B2 | 9/2016 | Felix et al. |
| 9,517,255 B2 | 12/2016 | Turzi |
| 9,642,956 B2 | 5/2017 | Landrigan et al. |
| 9,649,579 B2 | 5/2017 | Leach et al. |
| 9,656,274 B2 | 5/2017 | Ellsworth et al. |
| 9,694,359 B2 | 7/2017 | Losada et al. |
| 9,700,886 B2 | 7/2017 | Felix et al. |
| 9,714,890 B2 | 7/2017 | Newby et al. |
| 9,731,290 B2 | 8/2017 | Crawford et al. |
| 9,802,189 B2 | 10/2017 | Crawford et al. |
| 9,833,478 B2 | 12/2017 | Turzi et al. |
| 9,897,589 B2 | 2/2018 | Woodell-May |
| 9,919,307 B2 | 3/2018 | Crawford et al. |
| 9,919,308 B2 | 3/2018 | Crawford et al. |
| 9,919,309 B2 | 3/2018 | Crawford et al. |
| 9,933,344 B2 | 4/2018 | Newby et al. |
| 9,937,445 B2 | 4/2018 | King et al. |
| 9,962,480 B2 * | 5/2018 | Esteron ............... A61M 1/3693 |
| 10,005,081 B2 | 6/2018 | Duffy et al. |
| 10,016,459 B1 * | 7/2018 | Brahm ................. A61K 35/19 |
| 10,052,349 B2 | 8/2018 | Turzi et al. |

(56) References Cited

U.S. PATENT DOCUMENTS

| | | |
|---|---|---|
| 10,092,598 B2 | 10/2018 | Turzi et al. |
| 10,183,042 B2 | 1/2019 | Leach et al. |
| 10,343,157 B2 | 7/2019 | Crawford et al. |
| 10,350,591 B2 | 7/2019 | Felix et al. |
| 10,376,879 B2 | 8/2019 | Crawford et al. |
| 10,393,728 B2 | 8/2019 | Woodell-May |
| 10,413,898 B2 | 9/2019 | Crawford et al. |
| 10,456,782 B2 | 10/2019 | Crawford et al. |
| 10,603,665 B2 | 3/2020 | Levine et al. |
| 10,618,044 B1 | 4/2020 | Petrie, Jr. |
| 2002/0123140 A1 | 9/2002 | Bandyopadhyay et al. |
| 2002/0187130 A1 | 12/2002 | Kindness et al. |
| 2002/0193448 A1 | 12/2002 | Wallace et al. |
| 2003/0161938 A1 | 8/2003 | Johnson |
| 2003/0205538 A1 | 11/2003 | Dorian et al. |
| 2003/0233064 A1 | 12/2003 | Arm et al. |
| 2004/0059255 A1 | 3/2004 | Manoussakis et al. |
| 2004/0071786 A1 | 4/2004 | Grippi et al. |
| 2004/0103951 A1 | 6/2004 | Osborne et al. |
| 2004/0151709 A1 | 8/2004 | Barrueta et al. |
| 2004/0208786 A1 | 10/2004 | Kevy et al. |
| 2004/0251217 A1 | 12/2004 | Leach et al. |
| 2005/0008629 A1 | 1/2005 | Arm |
| 2005/0170327 A1 | 8/2005 | Sumida et al. |
| 2005/0205498 A1 | 9/2005 | Sowemimo-Coker et al. |
| 2006/0128016 A1 | 6/2006 | Tokushima et al. |
| 2007/0034579 A1 | 2/2007 | Dorian et al. |
| 2007/0036766 A1 | 2/2007 | Kevy et al. |
| 2007/0184029 A1 | 8/2007 | Mishra |
| 2008/0089918 A1 | 4/2008 | Lebreton |
| 2008/0199845 A1 | 8/2008 | Rosiello et al. |
| 2009/0035382 A1 | 2/2009 | Aldecoa et al. |
| 2009/0274627 A1 | 11/2009 | Yamada et al. |
| 2009/0298173 A1 | 12/2009 | Ueda et al. |
| 2010/0015226 A1 | 1/2010 | Turzi et al. |
| 2010/0184720 A1 | 7/2010 | Molliard et al. |
| 2013/0058906 A1 | 3/2013 | Turzi |
| 2014/0010857 A1 | 1/2014 | Turzi et al. |
| 2015/0090650 A1 | 4/2015 | Grippi et al. |
| 2015/0151858 A1 | 6/2015 | Turzi |
| 2015/0231626 A1 | 8/2015 | Shi et al. |
| 2016/0158286 A1 | 6/2016 | Turzi et al. |
| 2017/0080028 A1 | 3/2017 | Turzi et al. |
| 2017/0087228 A1 | 3/2017 | Turzi |
| 2017/0258839 A1 | 9/2017 | Turzi et al. |
| 2017/0304823 A1 | 10/2017 | Sparks et al. |
| 2017/0326544 A1 | 11/2017 | Emerson |
| 2018/0265839 A1* | 9/2018 | Retting ............... C12N 5/0656 |
| 2018/0304251 A1 | 10/2018 | Ellson et al. |
| 2018/0353952 A1 | 12/2018 | Olson |
| 2020/0009304 A1 | 1/2020 | Dorian et al. |
| 2020/0009552 A1 | 1/2020 | Crawford et al. |
| 2020/0129560 A1 | 4/2020 | Centeno et al. |
| 2020/0197929 A1 | 6/2020 | Weinstock et al. |
| 2020/0215243 A1 | 7/2020 | Dorian et al. |
| 2020/0246516 A1 | 8/2020 | Dorian et al. |
| 2020/0289720 A1 | 9/2020 | Streit |

FOREIGN PATENT DOCUMENTS

| | | | |
|---|---|---|---|
| CN | 105640993 A * | 6/2016 | |
| DE | 8910591 U1 | 12/1989 | |
| EP | 0744026 B1 | 11/2001 | |
| EP | 1547606 A1 | 6/2005 | |
| EP | 1444984 B1 | 9/2008 | |
| EP | 2068268 A1 | 6/2009 | |
| EP | 2073862 A2 | 7/2009 | |
| EP | 1543846 B1 | 8/2009 | |
| EP | 2185163 A2 | 5/2010 | |
| EP | 2544697 B1 | 5/2017 | |
| EP | 3111974 A3 | 5/2017 | |
| EP | 3184114 B1 | 10/2018 | |
| ES | 2333498 B1 | 1/2011 | |
| FR | 2918276 B1 | 1/2010 | |
| JP | 2006515853 A | 6/2006 | |
| JP | 2006181365 A | 7/2006 | |
| JP | 2008214771 A | 9/2008 | |
| JP | 2009235004 A | 10/2009 | |
| JP | 2010535188 A | 11/2010 | |
| JP | 2015232028 A | 12/2015 | |
| KR | 20100075827 A | 7/2010 | |
| RU | 2010107463 A | 9/2011 | |
| RU | 2614722 C2 * | 3/2017 | ........... A61K 31/728 |
| WO | 8605984 A1 | 10/1986 | |
| WO | 9515352 A1 | 6/1995 | |
| WO | 9618897 A1 | 6/1996 | |
| WO | 9717025 A1 | 5/1997 | |
| WO | 9856247 A1 | 12/1998 | |
| WO | 9966923 A1 | 12/1999 | |
| WO | 9966964 A1 | 12/1999 | |
| WO | 2000044022 A1 | 7/2000 | |
| WO | 03092894 A2 | 11/2003 | |
| WO | 2004024198 | 6/2004 | |
| WO | 2004084825 A2 | 10/2004 | |
| WO | 2005048958 A1 | 6/2005 | |
| WO | 2006082661 A1 | 8/2006 | |
| WO | 2006123579 A1 | 11/2006 | |
| WO | 2006136870 A1 | 12/2006 | |
| WO | 2008022651 A1 | 2/2008 | |
| WO | 2008023026 A2 | 2/2008 | |
| WO | 2009066102 A1 | 5/2009 | |
| WO | 2009071445 A1 | 6/2009 | |
| WO | 2009016451 A9 | 4/2010 | |
| WO | 2009098698 A3 | 4/2010 | |
| WO | 2011110948 A2 | 9/2011 | |
| WO | 2012103100 A1 | 8/2012 | |
| WO | 2012118922 A3 | 12/2012 | |
| WO | 2013061309 A2 | 5/2013 | |
| WO | 2013103982 A1 | 7/2013 | |
| WO | 2016083549 A3 | 7/2016 | |
| WO | 2018197562 A1 | 11/2018 | |
| WO | 2018197564 A1 | 11/2018 | |
| WO | 2018197592 A1 | 11/2018 | |
| WO | 2019107509 A1 | 6/2019 | |
| WO | 2020013981 A1 | 1/2020 | |
| WO | 2020013997 A1 | 1/2020 | |
| WO | 2020154305 A1 | 7/2020 | |
| WO | 2020163105 A1 | 8/2020 | |

OTHER PUBLICATIONS

Laurens, I. "Development of a new extraction method for platelet-rich plasma and partial purification of platelet-derived growth factor and transforming growth factor beta" University of Pretoria, Oct. 2013, pp. 148.

Leitner GC, Gruber R, Neumüller J, Wagner A, Kloimstein P, Höcker P, Körmöczi GF, Buchta C. Platelet content and growth factor release in platelet-rich plasma: a comparison of four different systems. Vox Sang. Aug. 2006;91(2):135-9.

Lippross, S. and M. Alini. "Platelet-rich plasma for bone healing—to use or not to use ?" (2007).

Liu L, Hartwig D, Harloff S, Herminghaus P, Wedel T, Kasper K, Geerling G. Corneal epitheliotrophic capacity of three different blood-derived preparations. Invest Ophthalmol Vis Sci. Jun. 2006;47(6):2438-44.

Liu Y, Kalén A, Risto O, Wahlström O. Fibroblast proliferation due to exposure to a platelet concentrate in vitro is pH dependent. Wound Repair Regen. Sep.-Oct. 2002;10(5):336-40.

Lozada JL, Caplanis N, Proussaefs P, Willardsen J, Kammeyer G. Platelet-rich plasma application in sinus graft surgery: Part I—Background and processing techniques. J Oral Implantol. 2001;27(1):38-42.

Magalon J, Bausset O, Serratrice N, Giraudo L, Aboudou H, Veran J, Magalon G, Dignat-Georges F, Sabatier F. Characterization and comparison of 5 platelet-rich plasma preparations in a single-donor model. Arthroscopy. May 2014;30(5):629-38.

Magalon J, Chateau AL, Bertrand B, Louis ML, Silvestre A, Giraudo L, Veran J, Sabatier F. DEPA classification: a proposal for standardising PRP use and a retrospective application of available devices. BMJ Open Sport Exerc Med. Feb. 4, 2016;2(1).

(56) References Cited

OTHER PUBLICATIONS

Maino VC, Suni MA, Ruitenberg JJ. Rapid flow cytometric method for measuring lymphocyte subset activation. Cytometry. Jun 1, 1995;20(2):127-33.
Man D, Plosker H, Winland-Brown JE. The use of autologous platelet-rich plasma (platelet gel) and autologous platelet-poor plasma (fibrin glue) in cosmetic surgery. Plast Reconstr Surg. Jan. 2001;107(1):229-37; discussion 238-9.
Marlovits S, Mousavi M, Gäbler C, Erdös J, Vécsei V. A new simplified technique for producing platelet-rich plasma: a short technical note. Eur Spine J. Oct. 2004;13 Suppl 1(Suppl 1):S102-6. Epub Jun. 22, 2004.
Martin Lind (1996) Growth factors: Possible new clinical tools: A review, Acta Orthopaedica Scandinavica, 67:4, 407-417.
Marx RE, Carlson ER, Eichstaedt RM, Schimmele SR, Strauss JE, Georgeff KR. Platelet-rich plasma: Growth factor enhancement for bone grafts. Oral Surg Oral Med Oral Pathol Oral Radiol Endod. Jun. 1998;85(6):638-46.
Marx RE. Platelet-rich plasma (PRP): what is PRP and what is not PRP? Implant Dent. 2001;10(4):225-8.
Mazzucco L, Medici D, Serra M, Panizza R, Rivara G, Orecchia S, Libener R, Cattana E, Levis A, Betta PG, Borzini P. The use of autologous platelet gel to treat difficult-to-heal wounds: a pilot study. Transfusion. Jul. 2004;44(7):1013-8.
Mazzucco L., et al, Platelet-Rich Plasma and Platelet Gel Preparation Using Plateltex®, Journal Compliation 2008 Blackwell Publishing Ltd., Vor Sanquinis Ltd, 7 pgs.
Melmed EP. Autologous platelet gel in plastic surgery. Aesthet Surg J. Jul. 2001;21(4):377-9.
Mishra A, Harmon K, Woodall J, Vieira A. Sports medicine applications of platelet rich plasma. Curr Pharm Biotechnol. Jun. 2012;13(7):1185-95.
Mishra A, Pavelko T. Treatment of chronic elbow tendinosis with buffered platelet-rich plasma. Am J Sports Med. Nov. 2006;34(11):1774-8. Epub May 30, 2006.
Mizuno D, Kagami H, Mizuno H, Mase J, Usami K, Ueda M. Bone regeneration of dental implant dehiscence defects using a cultured periosteum membrane. Clin Oral Implants Res. Mar. 2008;19(3):289-94. Epub Dec. 13, 2007.
Napolitano M, Matera S, Bossio M, Crescibene A, Costabile E, Almolla J, Almolla H, Togo F, Giannuzzi C, Guido G. Autologous platelet gel for tissue regeneration in degenerative disorders of the knee. Blood Transfus. Jan. 2012;10(1):72-7. Epub Oct. 25, 2011.
NCCLS. "Tubes and Additives for Venous Blood Specimen Collection; Approved Standard" Fifth Edition. NCCLS document H1-A5 [ISBN 1-56238-519-4]. NCCLS, 940 West Valley Road, Suite 1400, Wayne, Pennsylvania 19087-1898 USA, 2003.
Okuda K, Kawase T, Momose M, Murata M, Saito Y, Suzuki H, Wolff LF, Yoshie H. Platelet-rich plasma contains high levels of platelet-derived growth factor and transforming growth factor-beta and modulates the proliferation of periodontally related cells in vitro. J Periodontol. Jun. 2003,74(6):849-57.
Pape HC, Evans A, Kobbe P. Autologous bone graft: properties and techniques. J Orthop Trauma. Mar. 2010;24 Suppl 1:S36-40.
Parkinson, E. K. et al. "3. The Epidermis" "Culture of Epithelial Cells", 2002, pp. 65-94, 2nd Edition.
PCT Patent Application No. PCT/EP2006/065493 dated Aug. 21, 2006, Inventor Antoine Turzi, 35 pgs.
Perttilä J, Salo M, Peltola O. Plasma fibronectin concentrations in blood products. Intensive Care Med. 1990;16(1):41-3.
Pierce GF, Vande Berg J, Rudolph R, Tarpley J, Mustoe TA. Platelet-derived growth factor-BB and transforming growth factor beta 1 selectively modulate glycosaminoglycans, collagen, and myofibroblasts in excisional wounds. Am J Pathol. Mar. 1991,138(3):629-46.
Pietrzak WS, Eppley BL. Platelet rich plasma: biology and new technology. J Craniofac Surg. Nov. 2005;16(6):1043-54.
Platelet count—definition of platelet count by medical dictionary. https://medical-dictionary.thefreedictionary.com/platelet+count.
Powell DM, Chang E, Farrior EH. Recovery from deep-plane rhytidectomy following unilateral wound treatment with autologous platelet gel: a pilot study. Arch Facial Plast Surg. Oct.-Dec. 2001;3(4):245-50.
Raffoul, Wassim & Guerid, S. & Darwich, S. & Berger, Mette & Hayoz, Daniel & Benathan, M . . . (2008). Impact of platelets concentrate and keratinocyte suspension on wound healing—a prospective randomized trial. The International journal of artificial organs. 31. 16 pgs.
Regen Lab brochure entitled "RegenPRP-Kit" available at www.regenkit.com as of Sep. 26, 2004.
Regen Lab presentation entitled "Innovation in Biological Tissue Regeneration", 2005.
Mandle, Robert, Research Study, Comparison of EmCyte GS30-PurePRP II, EmCyte GS60-PurePRP II, Arteriocyte Magellan, Stryker RegenKit THT, and Eclipse PRP, May 6, 2016, 14 pgs.
Rheinwald, J. G. et al. "Formation of a Keratinizing Epithelium in Culture by a Cloned Cell Line Derived from a Teratoma" Cell, Nov. 1975, pp. 317-330, vol. 6.
Ronfard, V. et al. "Use of human keratinocytes cultured on fibrin glue in the treatment of burn wounds" Burns, 1991, pp. 181-184, vol. 17, No. 3.
Sadati, K., et al., "Platelet-Rich Plasma (PRP) Utilized To Promote Greater Graft Volume Retention in Autologous Fat Grafting", The American Journal of Cosmetic Surgery, vol. 23, No. 4, 2006.
Sánchez AR, Sheridan PJ, Kupp LI. Is platelet-rich plasma the perfect enhancement factor? A current review. Int J Oral Maxillofac Implants. Jan.-Feb. 2003;18(1):93-103.
Sánchez M, Anitua E, Azofra J, Aguirre JJ, Andia I. Intra-articular injection of an autologous preparation rich in growth factors for the treatment of knee OA: a retrospective cohort study. Clin Exp Rheumatol. Sep.-Oct. 2008;26(5):910-3.
Schnabel LV, Mohammed HO, Miller BJ, McDermott WG, Jacobson MS, Santangelo KS, Fortier LA. Platelet rich plasma (PRP) enhances anabolic gene expression patterns in flexor digitorum superficialis tendons. J Orthop Res. Feb. 2007,25(2):230-40.
Selected Normal Pediatric Laboratory Values, https://pdf4pro.com/view/selected-normal-pediatric-laboratory-values-37fca4.html.
Shenkman B, Brill A, Brill G, Lider O, Savion N, Varon D. Differential response of platelets to chemokines: Rantes non-competitively inhibits stimulatory effect of SDF-1 alpha. J Thromb Haemost. Jan. 2004;2(1):154-60. d.
Slater M, Patava J, Kingham K, Mason RS. Involvement of platelets in stimulating osteogenic activity. J Orthop Res. Sep. 1995;13(5):655-63.
Slichter, et al., "Platelet Transfusion Therapy", Chapter 14 in "Platelets In Hematologic And Cardiovascular Disorders. A Clinical Handbook". Edited by Paolo Gresele et al.; Cambridge University Press 2008.
Smith, R. G. et al. "Platelet-rich Plasma: Properties and Clinical Applications." The Journal of Lancaster General Hospital • Summer 2007 • vol. 2—No. 2.
Biomet Biologics, Recover Platelet Separation Kit, 20 pgs.
Biomet Europe, Cell Factor Technologies, Inc., GPS II System, Gravitational Platelet Separation System User Manual, 14 pgs.
Cellenis PRP Revive Your Natural Beauty in a Natural Way, Estar Aesthetics, www.estar-medical.com, 2 pgs. Tropocells System.
Cellenis PRP Skin Rejuvenation, PRP Preparation Simplicity For Success, 2 pgs., www.estar-medical.com, Tropocells System.
Greiner Bio-One, Instructions on Proper Use of Serum Tubes, 2 pgs.
Lind M. Growth factors: possible new clinical tools. A review. Acta Orthop Scand. Aug. 1996;67(4):407-17.
OMS Patient Procedures, Bone Grafting, Whitewater Oral Surgery Group, http://www.whitewatersurgery.com, 5 pgs.
Rheinwald JG, Green H. Serial cultivation of strains of human epidermal keratinocytes: the formation of keratinizing colonies from single cells. Cell. Nov. 1975;6(3):331-43.
Sotiri I, Overton JC, Waterhouse A, Howell C. Immobilized liquid layers: A new approach to anti-adhesion surfaces for medical applications. Exp Biol Med (Maywood). May 2016;241(9):909-18. Epub Mar. 27, 2016.
Storry JR. Review: the function of blood group-specific RBC membrane components. Immunohematology. 2004;20(4):206-16.

(56) References Cited

OTHER PUBLICATIONS

Stryer, L. Biochemistry, 3rd Edition. Stanford University, W.H. Freeman & Company, New York, Chapter 11, Connective-Tissue Proteins.
The Merck Manual for Health Care Professionals, "Appendix II Normal Laboratory Values, 2011, pp. 1-9."
Thermo Scientific, Tech Tip #40, Convert Between Times Gravity (xg) and Centrifuge Rotor Speed (RPM), 1 pg.
Tischler M. "Platelet rich plasma—utilizing autologous growth factors for dental surgery to enhance bone and soft tissue grafts", New York State Dental Journal 3-02.
Toit, Don F & Kleintjes, Wayne & Otto, Morkel & Mazyala, Erick J & Page, BenedictJ. Soft and hard-tissue augmentation with platelet-rich plasma: Tissue culture dynamics, regeneration and molecular biology perspective. International Journal of Shoulder Surgery. IJSS Apr. 2007, vol. 1, Issue 2.
Tözüm TF, Demiralp B. Platelet-rich plasma: a promising innovation in dentistry. J Can Dent Assoc. Nov. 2003;69(10):664.
Tsay et al., "Differential growth factor retention by platelet-rich plasma composites". J. Oral. Maxil/ofac. Surg. 2005. 63:521-528.
Van Den Dolder, J. et al, "Platelet-Rich Plasma: Quantification of Growth Factor Levels and the Effect on Growth and Differentiation of Rat Bone Marrow Cells", Tissue Engineering, vol. 12, No. 11, 2006; pp. 3067-3073.
Van Laethem K, Beuselinck K, Van Dooren S, De Clercq E, Desmyter J, Vandamme AM. Diagnosis of human immunodeficiency virus infection by a polymerase chain reaction assay evaluated in patients harbouring strains of diverse geographical origin. J Virol Methods. Feb. 1998;70(2):153-66.
Wang HL, Avila G. Platelet rich plasma: myth or reality? Eur J Dent. Oct. 2007;1(4):192-4.
Waters JH, Roberts KC. Database review of possible factors influencing point-of-care platelet gel manufacture. J Extra Corpor Technol. Sep. 2004;36(3):250-4.
Weibrich G, Hansen T, Kleis W, Buch R, Hitzler WE. Effect of platelet concentration in platelet-rich plasma on peri-implant bone regeneration. Bone. Apr. 2004;34(4):665-71.
Weibrich G, Kleis WK, Buch R, Hitzler WE, Hafner G. The Harvest Smart PRePTM system versus the Friadent-Schütze platelet-rich plasma kit. Clin Oral Implants Res. Apr. 2003;14(2):233-9.
Weibrich G, Kleis WK. Curasan PRP kit vs. PCCS PRP system. Collection efficiency and platelet counts of two different methods for the preparation of platelet-rich plasma. Clin Oral Implants Res. Aug. 2002;13(4):437-43.
Woodell-May JE, Ridderman DN, Swift MJ, Higgins J. Producing accurate platelet counts for platelet rich plasma: validation of a hematology analyzer and preparation techniques for counting. J Craniofac Surg. Sep. 2005;16(5):749-56; discussion 757-9.
World Health Organization, "Use of Anticoagulants in Diagnostic Laboratory Investigations", 2002 WHO/DIL/LAB/99.1 Rev.2, 64 pgs.
Wyss Institute for Biologically Inspired Engineering at Harvard. "Bioinspired coating for medical devices repels blood, bacteria." ScienceDaily. ScienceDaily, Oct. 12, 2014.
Zenker S., "Platelet Rich Plasma (PRP) for Facial Rejuvenation" J. Med. Esth. et Chir. Derm. vol. XXXVII, 148, Dec. 2010, 179-183.
Zillmann A, Luther T, Müller I, Kotzsch M, Spannagl M, Kauke T, Oelschlägel U, Zahler S, Engelmann B. Platelet-associated tissue factor contributes to the collagen-triggered activation of blood coagulation. Biochem Biophys Res Commun. Feb. 23, 2001;281(2):603-9.
Abuzeni, P.Z., et al, "Enhancement of Autologous Fat Transplantation with Platelet Rich Plasma", The American Journal of Cosmetic Surgery vol. 18, No. 2, 2001, 12 pgs.
Agrawal A.A., "Evolution, Current Status and Advances in Application of Platelet Concentrate in Periodontics and Implantology", World Journal of Clinical Cases May 16, 2017; 5(5): 159-171, ISSN 2307-8960 (online).

Alberts B., et al. "Molecular Biology of the Cell", 4th edition. New York: Garland Science; 2002. Chapter 19, "Cell Junctions, Cell Adhesion, and the Extracellular Matrix", 65 pgs.
Alberts B., et al. "Molecular Biology of the Cell", 6th edition. New York: Garland Science; 2008. Chapter 19, "Cell Junctions and the Extracellular Matrix", 29 pgs.
Annunziata M., et al, "In Vitro Cell-Types Specific Biological Response of Human Periodontally Related Cells to Platelet-Rich Plasma", Journal of Periodontal Research, 2005; 40; 489-495, 7 pgs.
Antoine Turzi & Regen Lab Team Biobridge Foundation Editions, Platelet-Rich Plasma (PRP) Standardization & Cell Therapies, Biobridge Foundation ed. www.briobridge-event.com/knowledge, Regen Lab SA , www.regenlab.com, 180 pgs.
Appel, T. R., et al, "Comparison of Three Different Preparations of Platelet Concentrates for Growth Factor Enrichment", Clin. Oral Impl. Res. 13, 2002 / 522-528, 7 pgs.
BD Vacutainer CPT Cell Preparation Tube with Sodium Citrate. Product Insert, 2003.
Becton Dickinson Vacutainer Tube Guide, 2005.
Bornes, T.D., et al, "Mesenchymal Stem Cells in the Treatment of Traumatic Articular Cartilage Defects: A Comprehensive Review", Arthritis Research & Therapy 2014; 16(5), 30 pgs.
Braccini, F., et al, "Platelet-Rich Fibrin during Facial Lipostructure" Body Language, The UK Journal of Medical Aesthetics and Anti-Ageing, pp. 51-54.
Castillo, T. N., et al, "Comparison of Growth Factor and Platelet Concentration from Commercial Platelet-Rich Plasma Separation Systems", The American Journal of Sports Medicine, Feb. 2011;39(2):266-71.
Celotti, F., et al, "Effect of platelet-rich plasma on migration and proliferation of SaOS-2 osteoblasts: role of platelet-derived growth factor and transforming growth factor", Wound Repair and Regeneration (2006) 14; 195-202.
Christensen, K., et al, "Autologous Platelet Gel: An In Vitro Analysis of Platelet-Rich Plasma Using Multiple Cycles", The Journal of The American Society of Extra-Corporeal Technology, 2006;38:249-253.
Claim Chart for U.S. Appl. No. 12/438,236.
Currie, L.J., et al, "The Use of Fibrin Glue in Skin Grafts and Tissue-Engineered Skin Replacements: A Review", Plastic and Reconstructive Surgery, Nov. 2001, vol. 108, No. 6, 1713-1726.
De Oliveira S, Saldanha C. An overview about erythrocyte membrane. Clin Hemorheol Microcirc. 2010;44(1):63-74.
Delong, J.M, et al, "Level V. Evidence, Platelet-Rich Plasma: The PAW Classification System", Arthroscopy: The Journal of Arthroscopic and Related Surgery, vol. 28, No. 7 Jul. 2012: pp. 998-1009.
Demiralp, B., et al, "Treatment of Periapical Inflammatory Lesion with the Combination of Platelet-Rich Plasma and Tricalcium Phosphate: A Case Report", The American Association of Endodontists, Journal of Endodontics vol. 30, No. 11, Nov. 2004; pp. 796-800.
Details of clinical trial NCT00856934 from ClinicaiTrials.gov. Effect of Platelet Rich Plasma and Keratinocyte Suspensions on Wound Healing, 19 pgs.
Doucet, C., et al. "Platelet Lysates Promote Mesenchymal Stem Cell Expansion: A Safety Substitute for Animal Serum in Cell-Based Therapy Applications", Journal of Cellular Physiology 205: 228-236 (2005).
Eppley BL, et al, "Platelet quantification and growth factor analysis from platelet-rich plasma: implications for wound healing", American Society of Plastic Surgeons Nov. 2004;114(6):1502-8.
Eppley, B.L, et al, "Platelet-Rich Plasma: A Review of Biology and Applications in Plastic Surgery", Plastic and Reconstructive, Nov. 2006, vol. 118, No. 6, pp. 147e-159e.
Everts et al., "Platelet rich plasma and platelet gel, A review." J. Extra Corpor. Techn. 2006; 38: 174-187. Presented at: 21st Mechanisms of Perfusion Congress May 18-21, 2006, Orlando FL, USA.
Everts, P.A., et al, "Platelet-rich plasma preparation using three devices: Implications for platelet activation and platelet growth factor release" Growth Factors, Sep. 2006; 24(3): 165-171.
Evidence Based Healthcare Group, "Efficacy of Autologous Platelet Rich Plasma in Bone Healing—Evidence Based Review", Jun. 2007, pp. 1-32.

(56) References Cited

OTHER PUBLICATIONS

Erreira CF, et al, "Platelet-rich plasma influence on human osteoblasts growth", Clinical Oral Implants Research, Aug. 2005;16(4):456-60.
Forni, F., et al, "Platelet gel: applications in dental regenerative surgery", Blood Transfus. Jan. 2013;11(1):102-7.
Fried DW, et al, Quantitative and qualitative analysis of platelet-rich plasma collection using the Haemonetics Cell Saver 5 in open heart surgery, The Journal of The American Society of Extra-Corporeal Technology, Sep. 2006;38(3):235-40.
Fulton, J. "Breast Contouring with 'Gelled' Autologous Fat: A 10-Year Update" International Journal of Cosmetic Surgery and Aesthetic Dermatology, 2003, pp. 155-163, vol. 5, No. 2.
Weibrich G., et al, "Effect of Platelet Concentration in Platelet-Rich Plasma on Peri-Implant Bone Regeneration", Elsevier, Bone 34 (2004) 665-671.
Gadol et al., "A new method for separating mononuclear cell from whole blood". Diagn. Immunol. 1985; 3(3): 145-54.
Garratty G, Telen MJ, Petz LD. "Red cell antigens as functional molecules and obstacles to transfusion", Hematology Am Soc Hematol Educ Program. 2002:445-62.
Gentile P, Di Pasquali C, Bocchini I, Floris M, Eleonora T, Fiaschetti V, Floris R, Cervelli V. Breast reconstruction with autologous fat graft mixed with platelet-rich plasma. Surg Innov. Aug. 2013;20(4):370-6.
Gluckman E, Rocha V, Boyer-Chammard A, Locatelli F, Arcese W, Pasquini R, Ortega J, Souillet G, Ferreira E, Laporte JP, Fernandez M, Chastang C. Outcome of cord-blood transplantation from related and unrelated donors. Eurocord Transplant Group and the European Blood and Marrow Transplantation Group. N Engl J Med. Aug. 7, 1997;337(6):373-81.
Gobbi A, Karnatzikos G, Mahajan V, Malchira S. Platelet-rich plasma treatment in symptomatic patients with knee osteoarthritis: preliminary results in a group of active patients. Sports Health. Mar. 2012;4(2):162-72.
Graziani et al., "The in vitro effect of different PRP concentrations on osteoblasts and fibroblasts", Clinical Oral. Implants Research May 2006; 17(2): 212-219.
Greco, J . . . "Micro Needling and Injecting Platelet Rich Plasma to Enhance Collagen Synthesis and Skin Tightening." (2007).
Guerid S, Darwiche SE, Berger MM, Applegate LA, Benathan M, Raffoul W. Autologous keratinocyte suspension in platelet concentrate accelerates and enhances wound healing—a prospective randomized clinical trial on skin graft donor sites: platelet concentrate and keratinocytes on donor sites. Fibrogenesis Tissue Repair. Apr. 9, 2013;6(1):8.
Guy Fortier et al., "Study Report, Regen THT Tube Performance Testing at US FDA Request", Study 2010-01 REV00, 2010, 17 pgs.
Hanson SR, Harker LA. Interruption of acute platelet-dependent thrombosis by the synthetic antithrombin D-phenylalanyl-L-prolyl-L-arginyl chloromethyl ketone. Proc Natl Acad Sci U S A. May 1988;85(9):3184-8.
Haynesworth, S. et al. "Mitogenic Stimulation of Human Mesenchymal Stem Cells by Platelet Releasate Suggests a Mechanism for Enhancement of Bone Repair by Platelet Concentrate." 48th Annual Meeting of the Orthopaedic Research Society, Poster No. 0462 (2001).
Hooiveld MJ, Roosendaal G, van den Berg HM, Bijlsma JW, Lafeber FP. Haemoglobin-derived iron-dependent hydroxyl radical formation in blood-induced joint damage: an in vitro study. Rheumatology (Oxford). Jun. 2003;42(6):784-90. Epub Mar. 31, 2003.
Kaux JF, Le Goff C, Renouf J, Peters P, Lutteri L, Gothot A, Crielaard JM. Comparison of the platelet concentrations obtained in platelet-rich plasma (PRP) between the GPS™ II and GPS™ III systems. Pathol Biol (Paris). Oct. 2011;59(5):275-7. Epub Dec. 8, 2010.
Kaux JF, Le Goff C, Seidel L, Péters P, Gothot A, Albert A, Crielaard JM. Étude comparative de cinq techniques de préparation plaquettaire (platelet-rich plasma) [Comparative study of five techniques of preparation of platelet-rich plasma]. Pathol Biol (Paris). Jun. 2011;59(3):157-60. French. Epub May 28, 2009.
Kawase T, Okuda K, Wolff LF, Yoshie H. Platelet-rich plasma-derived fibrin clot formation stimulates collagen synthesis in periodontal ligament and osteoblastic cells in vitro. J Periodontol. Jun. 2003;74(6):858-64.
Kevy SV, Jacobson MS. Comparison of methods for point of care preparation of autologous platelet gel. J Extra Corpor Technol. Mar. 2004,36(1):28-35.
Kubota S, Kawata K, Yanagita T, Doi H, Kitoh T, Takigawa M. Abundant retention and release of connective tissue growth factor (CTGF/CCN2) by platelets. J Biochem. Sep. 2004;136(3):279-82.
Kubota Y, Tanaka T, Ohnishi H, Kitanaka A, Okutani Y, Taminato T, Ishida T, Kamano H. Constitutively activated phosphatidylinositol 3-kinase primes platelets from patients with chronic myelogenous leukemia for thrombopoietin-induced aggregation. Leukemia. Jun. 2004;18(6):1127-37.
Kushida S, Kakudo N, Morimoto N, Hara T, Ogawa T, Mitsui T, Kusumoto K. Platelet and growth factor concentrations in activated platelet-rich plasma: a comparison of seven commercial separation systems. J Artif Organs. Jun. 2014;17(2):186-92. Epub Apr. 20, 2014.
Japanese Office Action for Application No. 2022525168 dated Nov. 5, 2023 including JPO English translation.
European Search Report for Application No. 208834960 dated Nov. 22, 2023 but received Nov. 21, 2023.
Canadian Office Action for Application No. 3159372 dated Nov. 3, 2023.

\* cited by examiner

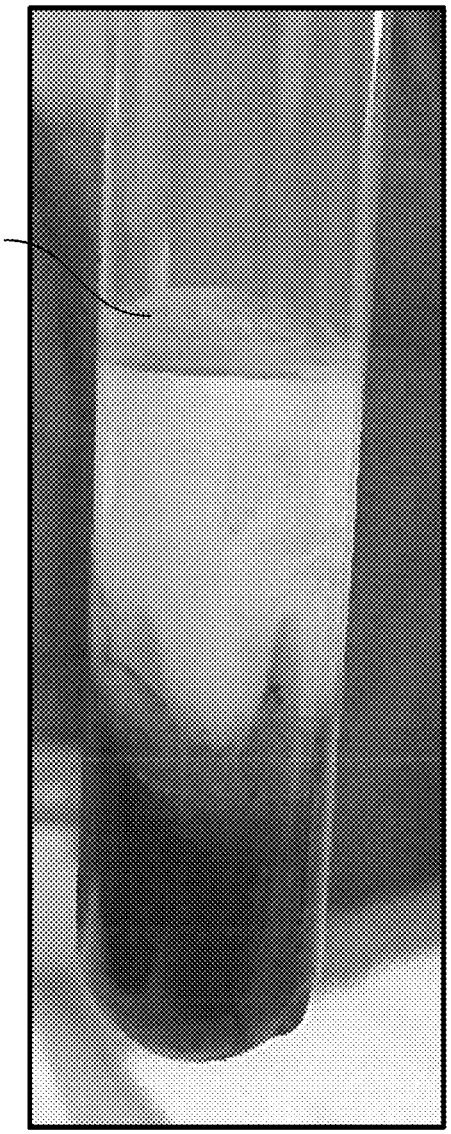 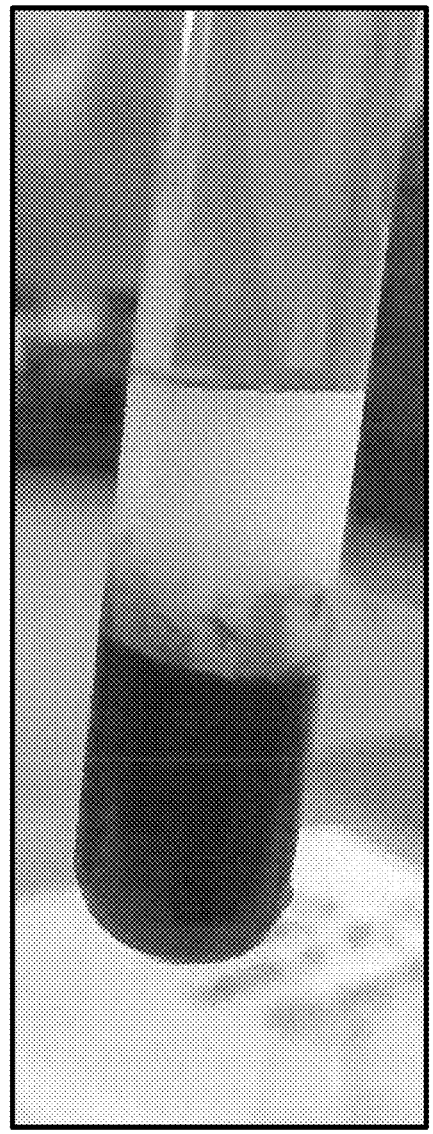
*FIG. 4A*  *FIG. 4B*

SYSTEMS, METHODS AND APPARATUS FOR SEPARATING COMPONENTS OF A SAMPLE

BACKGROUND

This background section is intended to provide a discussion of related aspects of the art that could be helpful to understanding the embodiments discussed in this disclosure. It is not intended that anything contained herein be an admission of what is or is not prior art, and accordingly, this section should be considered in that light.

Platelet-rich plasma (PRP) is generally understood to be a concentrate of platelets in plasma, that also contains growth factors, such as Platelet-Derived Growth Factor (PDGF); Transforming Growth Factor (TGF); Epidermal Growth Factor (EGF); Vascular Endothelial Growth Factor (VEGF); Fibroblast Growth Factor (FGF); and Keratinocyte Growth Factor (KGF), which regulate the healing cascade by signaling surrounding cells to repair damaged tissue and regenerate new tissue.

Various systems and methods for preparing PRP are known; but, for a variety of reasons, these methods and systems do not consistently provide efficient platelet capture. For example, devices and systems utilizing a separator gel tend to have issues with platelets adhering to the separator gel and breach of the separator gel following centrifugation. As a result, the clinician is often left with a less than desirable number of platelets available for administration to a patient. In addition, systems utilizing separator floats or barriers alone to separate components of a sample are often difficult to manufacture and/or complex and therefore not practical for point of care use.

To overcome the aforementioned challenges, there remains a need for simple, cost-effective, reliable, and clinically useful methods that enrich platelet concentrations and increase the number of platelets available for administration to a patient. Embodiments of the present disclosure are designed to meet these and other ends.

SUMMARY

This summary provides a discussion of aspects of certain embodiments of the invention. It is not intended to limit the claimed invention or any of the terms in the claims. The summary provides some aspects but there are aspects and embodiments of the invention that are not discussed here.

In some embodiments, the present disclosure is directed to a system for separating components of a sample, comprising: an apparatus comprising: a tubular body for receiving a liquid biological sample; a thixotropic material; and a float comprising: a core; a top surface; and a bottom surface; wherein the float has a specific gravity less than or equal to the specific gravity of the thixotropic material. In some embodiments, the tubular body comprises a proximal end and a distal end, the distal end being closed to the external environment and the proximal end having an aperture capable of receiving a sample. In some embodiments, the proximal end of the tubular body is sealed from the external environment by a stopper.

Other embodiments of the disclosure provide a system for separating components of a sample comprising: a tubular body; a float; and a thixotropic material; wherein the volume and rheological profile of the thixotropic material and the dimensions of the float are configured to permit density separation of the components of the sample by centrifugation.

Other embodiments of the disclosure provide compositions comprising a product produced by any one of the methods or systems described herein, while other embodiments provide methods of using a product produced by any one of the methods or systems described herein.

Still, further embodiments of the disclosure provide a system for separating components of a biological sample comprising: a biological sample; a tube; a thixotropic material and float disposed within the tube; a means for applying a relative centrifugal force to said tube; and a means for agitating said tube.

Further areas of applicability of the present disclosure will become apparent from the detailed description provided hereinafter. The detailed description and specific examples, while describing embodiments, are intended for purposes of illustration only and are not intended to limit the scope of the present disclosure.

BRIEF DESCRIPTION OF THE DRAWINGS

FIG. 4A depicts an embodiment of a tube post-centrifugation with the tube centrifuged at a fixed angle between vertical and horizontal.

FIG. 4B depicts an embodiment of a tube post-centrifugation with the tube centrifuged horizontally.

DETAILED DESCRIPTION

Figure 1:
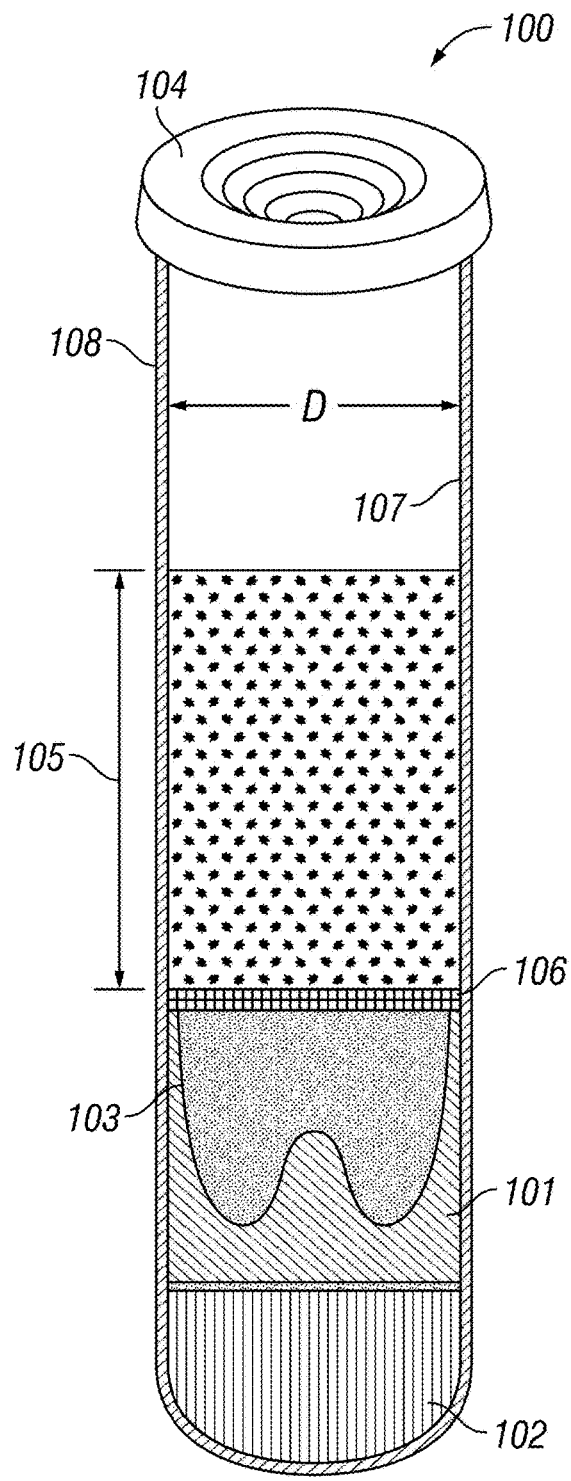
FIG. 1 depicts a partial cross section view of an embodiment of a tube for separating components of a sample, after introduction of a biological sample and post-centrifugation.

In some embodiments, the present disclosure involves the complementary interaction between a float and a thixotropic material situated in a tube. In certain embodiments, the present disclosure provides any one of the systems and apparatus described herein—e.g. a float, a thixotropic material and a tube. In some embodiments, the systems and apparatus of the present disclosure are used to separate components of a sample based on the relative densities of the sample's components. In some embodiments, the sample comprises human blood. In some embodiments, the thixotropic material and the float are each engineered with particular specific gravities, with the float having a specific gravity less than or equal to the specific gravity of the thixotropic material. In some embodiments, the float and thixotropic material each have a lower specific gravity than that of red blood cells. (When reference is made to the specific gravity of the gel, float, or blood component being lower than a referenced item, it is meant that the specific gravity is smaller than the specific gravity of the referenced item. It does not refer to a lower position in the tube pre- or post-centrifugation. For instance, if thixotropic material has a specific gravity of 1.06, a float with a specific gravity of 1.03 has a lower specific gravity than the thixotropic material.) In some embodiments, the float and thixotropic material each have greater specific gravity than plasma.

In some embodiments, the thixotropic material and the float act in a complementary fashion to, in the case of whole blood: 1) form a seal between the top component after centrifugation, also known as supernatant, (e.g., plasma) and a lower component (e.g., the red blood cells) in conjunction with the inner walls of the tube superior to a seal formed by gel alone, whether using a fixed angle or swing bucket centrifuge; 2) increase the platelet yield over a gel only separation system; and 3) reduce the possibility that the thixotropic material will rise above the top surface of the float and contaminate the supernatant (e.g., plasma) and/or adversely impact platelet counts.

As a skilled person would understand upon reading this disclosure, the thixotropic material (e.g., gel) can be provided in any amount that is effective to form a barrier in combination with the float and the inner surface of a tubular body (e.g., test tube). The effective amount of the thixotropic material can vary depending on the size of the test tube and the size of the float used with the thixotropic material and the sample volume. Additionally, as a skilled person would understand, the thixotropic material should not be used in such a large quantity that the thixotropic material will not fit in the tubular body together with the float and any sample to be separated into components. Moreover, it can be advantageous to avoid such a large quantity of thixotropic material that a globule, disk, portion, or the top portion of the thixotropic material tends to move toward a position above the float during or after centrifugation. As a skilled person would recognize, the desired volume of the thixotropic material can be determined by multiplying the desired thickness of the gel times the cross-sectional area of the annular space between the float and the inner surface of the tubular body and also considering the volume necessary to adequately encompass any extensions of the float (see FIG. 1). A skilled person would also recognize that, in some embodiments, the relative specific gravities between the float and the thixotropic material can be made disparate enough to ensure that the top surface of the float remains free or substantially free of the thixotropic material following centrifugation. Meanwhile, as an example, the desired thickness of the gel can be established such that, at a minimum, the thickness is adequate for providing a durable and impermeable barrier after centrifugation. Optionally, the thickness does not exceed a thickness that would cause the thixotropic material to extend above the top end of the float or, as a further alternative, the thickness is chosen to avoid causing the thixotropic material to cover any selected portion of the top surface of the float as described in this disclosure. In some embodiments, it is desirable to use a minimum amount of thixotropic material that provides an adequate barrier in combination with the float and the inner surface of the tubular body (i) in order to avoid costs associated with the thixotropic material, (ii) in order to avoid platelets being trapped by the thixotropic material, or (iii) any combination thereof.

In some embodiments, the float, and the thixotropic material each have specific gravities between that of the supernatant (e.g., plasma) and the red blood cells. The specific gravities of the thixotropic material and the float can be engineered so that, after centrifugation, the thixotropic material encases the float to form a seal in combination with the float while the top surface of float remains free or substantially free of the thixotropic material. This could mean, for example, that after centrifugation, (1) and after the tubular body is oriented with the opening of the tubular body being topmost (regardless of whether the centrifugation occurred at a different orientation) no more than 90, 80, 70, 60, 50, 40, 30, 25, 20, 15, 10, 9, 8, 7, or 6% by volume of the float is below a reference plane parallel to, tangent to or both parallel and tangent to the upper surface of the thixotropic material where the upper surface of the thixotropic material contacts the float; (2) and after the tubular body is oriented with the opening of the tubular body being topmost (regardless of whether the centrifugation occurred at a different orientation) at least 90, 80, 70, 60, 50, 40, 30, 25, 20, 15, 10, 9, 8, 7, 6 or 5% by volume of the float is below a reference plane parallel to, tangent to, or both parallel and tangent to the upper surface of the thixotropic material where the upper surface of the thixotropic material contacts the float; (3) no more than 70, 60, 50, 40, 30, 25, 20, 15, 10, 9, 8, 7, or 6% by volume of the float is coated with the thixotropic material, wherein the volume of the float coated with the thixotropic material is defined as the volume of the float that would be above an imaginary horizontal reference plane that would pass through the lowest point of a continuous mass of the thixotropic material that coats the float if the float were permitted to float freely under the force of gravity in the test liquid (regardless of whether the centrifugation occurred at a different orientation); (4) at least 60, 50, 40, 30, 25, 20, 15, 10, 9, 8, 7, 6 or 5% by volume of the float is coated with the thixotropic material, wherein the volume of the float coated with the thixotropic material is defined as the volume of the float that would be above an imaginary horizontal reference plane that would pass through the lowest point of a continuous mass of the thixotropic material that coats the float if the float were permitted to float freely under the force of gravity in the test liquid (regardless of whether the centrifugation occurred at a different orientation); (5) at least 80, 70, 60, 50, 40, 30, 25, 20, 15, 10, 9, 8, 7, 6 or 5% of the total surface area of the float is coated with the thixotropic material; (6) no more than 80, 70, 60, 50, 40, 30, 25, 20, 15, 10, 9, 8, 7, 6% of the total surface of the float is coated with the thixotropic material; (7) at least 90, 80, 70, 60, 50, 40, 30, 20% of the surface area of the float is below the upper surface of the thixotropic material; (8) no more than 90, 80, 70, 60, 50, 40, 30, 20, 10, 5, 4, 3, 2, 1% of the surface area of the float is below the upper surface of the thixotropic material, (9) at least 60, 50, 40, 30, 25, 20, 15, 10, 9, 8, 7, 6, 5, 4, 3, 2, 1 or 0% of the surface area of the top surface of the float is coated with the thixotropic material; or (10) no more than 70, 60, 50, 40, 30, 25, 20, 15, 10, 9, 8, 7, 6, 5, 4, 3, 2, 1, or 0% of the surface area of the top surface of the float is coated with the thixotropic material in some embodiments, optionally wherein the top surface of the float is defined as the portion of the float that is visible from above the float, optionally (i) from directly above the center of mass of the float, (ii) from a point along the central axis of the float, (iii) from a point along the longitudinal axis of the float or the length of the float, (iv) while the float is floating freely under the force of gravity in a fluid (e.g., relatively flowable fluid, fluid having a viscosity from 0.5 cP up to 40 cP at 25° C., fluid being or approximating a Newtonian fluid, or any combination thereof), (iv) along a line parallel to the axis of centrifugation, or (v) any combination thereof; (11) at least 80, 70, 60, 50, 40, 30, 25, 20, 15, 10, 9, 8, 7, 6 or 5% of the total surface area of the float is coated with plasma; (12) no more than 80, 70, 60, 50, 40, 30, 25, 20, 15, 10, 9, 8, 7, 6% of the total surface of the float is coated with plasma; or (13) any combination thereof.

The surface (e.g., top surface) of the float (or the volume enclosed by the surface of the float) supplants gel in separation systems employing only a thixotropic material as the separator, wherein some of the sought-after supernatant components (e.g., platelets) adhere to the thixotropic material, and harvesting of those components is thereby reduced. In certain embodiments of the present disclosure, wherein the top surface of the float is above the barrier formed, the harvest of sought-after supernatant components (e.g. platelets) is enhanced because the hard, impervious, non-tacky surface of the float minimizes the interaction between the sticky materials used in conventional gel only separations systems described in the art. In some embodiments, a small amount of thixotropic material may rise above the top surface of the float. In other embodiments, however, the upper surface of the thixotropic material is below the top surface of the float after centrifugation, which limits the exposure of platelets to the thixotropic material, thereby avoiding an unnecessary reduction in APC (as defined herein below).

Some embodiments of the present disclosure also address other problems presented by current separation systems. For example, there is a recognized problem in the art with achieving the proper seal or barrier between a float designed to form a seal with the inner diameter of the tube (see, e.g., EP 0 744 026 B1, EP 2 913 108 B1). This is often caused by a lack of precision in the manufacturing process when tubes are mass produced. Embodiments of the present disclosure address this issue through the use of a unique combination of a thixotropic material and a float, which not only eliminates the need for absolute precision in manufacturing and associated cost, but also reduces or eliminates the breach observed with currently available gel only separation systems.

As used herein, the term "breach" refers to the infiltration of red blood cells into the plasma portion of the sample post-centrifugation. In conventional gel only systems, breach can be caused by failure of the separator material to maintain integrity after, for example, agitating, shaking, or inverting the tube post-centrifugation. This agitation, shaking or inversion can occur, for example, because Instructions for Use ("IFU") typically require some method to re-suspend platelets in the PRP sample after centrifugation (which can be used, for example, to loosen platelets from the separator gel). Some embodiments of the present disclosure provide a more resilient barrier between a first component or second phase (e.g., plasma) and a second component or first phase (e.g. blood cells, red blood cells) that are to be separated using centrifugation. Advantageously, the more resilient barrier of some embodiments of the present disclosure enable more vigorous agitation than permitted or suggested by the IFU of existing systems, which may typically require gentler agitation, for example, only inversion or titling of a tube, perhaps 1 time per second for up to 10 seconds, but not shaking. The increased agitation of some embodiments of the present disclosure can also result in better suspension of platelets in a plasma or platelet rich plasma (PRP). Additionally, some embodiments of the present disclosure provide plasma or platelet rich plasma (PRP) with increased available platelet counts (APC) compared to existing embodiments. Furthermore, some embodiments of the present invention provide a commercially useful plasma or PRP after a shorter period of centrifugation at a given relative centrifugal force (RCF).

In some embodiments, the thixotropic material and the float are designed to remain substantially in place (e.g., in a tubular body, for example, a test tube) during transport (e.g., move along a central axis or length of the tubular body by no more than 15, 10, 9, 8, 7, 6, 5, 4, 3, 2 or 1% of the length of the float along the longitudinal axis or the central axis or the length of the float). Specifically, the thixotropic material (e.g., gel) is disposed in the closed end of the tubular body and the float is embedded in the material so that the float remains at the bottom of the tubular body. This can help avoid interference with blood collection by leaving an accessible empty volume at the open end of the tubular body where a biological sample, such as blood, can be placed in the tubular body. This is an important benefit provided by some embodiments of the present disclosure, as it assures that the float is in the correct position prior to the addition of a sample to the tube.

In some embodiments, the sample is a biological sample. In some embodiments, the tube contains a thixotropic material. In some embodiments, the thixotropic material is a glue or a gel. Further embodiments provide systems wherein there is little to no unbound or "free" thixotropic material in the tube after centrifugation. In some embodiments, the tube further comprises an anticoagulant.

Some embodiments of the present disclosure provide a tubular body comprising a material selected from: glass; modified poly amide (MPA); polyethylene terephthalate (PET); and any other material that is inert to a biological sample. In some embodiments, the tubular body comprises a laminate structure wherein an exterior wall of the tubular body is made of a material different than the interior wall.

In some embodiments, the apparatus described herein comprises a vessel having any shape configured to accept a sample. In some embodiments, the apparatus described herein comprises a vessel having any shape capable of being centrifuged. In some embodiments, the vessel is selected from a vessel having a rectangular or square cross-section (e.g. a cuvette) and a vessel having a triangular cross-section. In those embodiments wherein the vessel does not have a substantially circular cross-section, the float is configured according to the vessel geometry.

In some embodiments, the tubular body further comprises a stopper. In some embodiments, the stopper comprises a material inert to biological samples. In other embodiments, the stopper comprises a material that does not crumble. In certain embodiments, the stopper comprises silicone, butyl rubber, or its halo derivative formulations (e.g., halobutyl rubber, chlorobutyl rubber, or bromobutyl rubber). In further embodiments, the stopper has a hardness of from about forty (40) to sixty (60) Shore A. In other embodiments, the stopper is designed to provide stable vacuum (e.g., inside the tubular body) for a period of about eighteen (18) to about thirty-six (36) months.

In some embodiments, the terms "barrier" and "seal" are used interchangeably.

In some embodiments, the tubular body is capable of receiving biological samples of from about four (4) ml to about one hundred (100) ml. In other embodiments, the tubular body is designed to receive biological samples of from about eight (8) ml to about fifty (50) ml. Still further embodiments provide a tubular body designed to receive biological samples of from about ten (10) ml to about thirty (30) or forty (40) ml. Other embodiments provide a tubular body designed to receive biological samples of from about eleven (11) ml or about twenty-two (22) ml.

In some embodiments, the tubular body is selected from: a vacuum tube, a non-vacuum tube, a plastic tube, a glass tube, a rigid tube, a non-rigid tube, a semi rigid tube and any combination thereof. In some embodiments, the terms "tube," "collection tube," "test tube," "tubular body," and the like, can be used interchangeably. In some embodiments, a vacuum tube can be useful to help facilitate the transfer of a liquid biological sample (e.g., blood) into the vacuum tube.

In some embodiments, the tubular body further comprises a gel. In some embodiments, the gel comprises a thixotropic gel. The gel can consist of any thixotropic gel known in the art to form a barrier between red blood cells and plasma following centrifugation. In further embodiments, the gel comprises a polymer. In certain embodiments, the gel can be a homopolymer or a co-polymer comprising a combination of monomers. In some embodiments, the gel comprises a polyacrylate, polyolefin, or polyester. In some embodiments, the gel comprises hydrogenated styrene-butadiene rubber, silica, white oil, and antioxidants. An example of a thixotropic gel is a serum separation gel available from Sekisui Diagnostics, with an address at One Wall Street, Burlington, Mass. 01803, USA.

Still further embodiments provide a thixotropic material (e.g., gel) having a density at 25° C. of from about 1.03 g/cm$^3$ to about 1.09 g/cm$^3$. Other embodiments provide a thixotropic material (e.g., gel) having a density at 25° C. of from about 1.04 g/cm$^3$ to about 1.07 g/cm$^3$. In some embodiments, the thixotropic material (e.g., gel) has a density at 25° C. of about 1.045 g/cm$^3$ to about 1.05 g/cm$^3$, or about 1.035 to about 1.055 g/cm$^3$. In some embodiments, the thixotropic material (e.g., gel) has a density at 25° C. of at least 1.02, 1.03, 1.04, 1.05, 1.06, 1.07 or 1.08 g/cm$^3$; a density at 25° C. that is no more than 1.03, 1.04, 1.05, 1.06, 1.07, 1.08 or 1.09 g/cm$^3$; a density at 25° C. that is less than the density of red blood cells (e.g., from the sample) at 25° C.; a density at 25° C. that is greater than the density of PRP (e.g., from the sample) at 25° C.; a density at 25° C. greater than the density at 25° C. of a float configured to form a barrier with the gel; a density at 25° C. equal to the density at 25° C. of a float configured to form a barrier with the thixotropic material (e.g., gel); or any combination thereof. In some embodiments, the thixotropic material (e.g. gel) can have a viscosity of 400,000 to 700,000 cP, at least 400,000, 500,000, 600,000, or 700,000 cP, no more than 400,000, 500,000, 600,000, or 700,000 cP, or any combination thereof; optionally the viscosity being measured at 20° C., 25° C. or 30° C.; and optionally the viscosity being measured at a first shear rate (e.g., a shear rate lower than a shear rate expected to be experienced during centrifugation at a desired centrifugal acceleration for purposes of separation; as examples, it is expected that the shear rate could be 0.1/s, 0.2/s, 0.3/s, 0.4/s, 0.5/s, 0.6/s, 0.7/s, 0.8/s, 0.9/s 1/s, 2/s, 3/s, 4/s, 5/s, 10/s, 20/s, 30/s, 40/s, 50/s, 100/s, 200/s, 300/s, 400/s, 500/s, 600/s, 700/s, 800/s, or 900/s); or any combination thereof. In some embodiments, the thixotropic material (e.g. gel) can have a viscosity of greater than 0 to 399,000 cP, at least 1, 2, 3, 4, 5, 6, 7, 8, 9, 10, 20, 30, 40, 50, 60, 70, 80, 90, 100, 1000, 10,000, 100,000, 200,000, 300,000, or 399,000; no more than 1, 2, 3, 4, 5, 6, 7, 8, 9, 10, 20, 30, 40, 50, 60, 70, 80, 90, 100, 1000, 10,000, 100,000, 200,000, 300,000, or 399,000; optionally the viscosity being measured at 20° C., 25° C. or 30° C.; and optionally the viscosity being measured at a second shear rate (e.g., a shear rate greater than the first shear rate; at a shear rate expected to be experienced during centrifugation at a desired centrifugal acceleration for purposes of separation; as examples, it is expected that the shear rate could be 0.2/s, 0.3/s, 0.4/s, 0.5/s, 0.6/s, 0.7/s, 0.8/s, 0.9/s 1/s, 2/s, 3/s, 4/s, 5/s, 10/s, 20/s, 30/s, 40/s, 50/s, 100/s, 200/s, 300/s, 400/s, 500/s, 600/s, 700/s, 800/s, 900/s or 1000/s).

In some embodiments, the float has a density at 25° C. of at least 1.02, 1.03, 1.04, 1.05, 1.06, 1.07 or 1.08 g/cm$^3$; a density at 25° C. that is no more than 1.03, 1.04, 1.05, 1.06, 1.07, 1.08 or 1.09 g/cm$^3$; a density at 25° C. that is less than the density of red blood cells (e.g., from the sample) at 25° C.; a density at 25° C. that is greater than the density of PRP (e.g., from the sample) at 25° C.; a density at 25° C. less than the density at 25° C. of a thixotropic material (e.g., gel) configured to form a barrier with the float; a density at 25° C. equal to the density at 25° C. of a thixotropic material (e.g., gel) configured to form a barrier with the float; or any combination thereof.

In some embodiments, the float can take on a variety of shapes and can be constructed from a variety of materials. As examples, the float can be made of, comprise, consist essentially of or consist of a polymer, a plurality of polymers, acrylonitrile butadiene styrene (ABS), polycarbonate, plastic, rubber, metal, a plurality of metals, metal alloys, or any combination thereof. An example of a material that can be used for a float includes ABS with a density of 1.03 grams per cubic centimeter. The float can be bullet shaped, cylindrical, wafer shaped, conic, spherical, or other symmetric or asymmetric shape. In some embodiments, the float can comprise extensions or claws on the lower portion, thereby providing more surface area for thixotropic material adherence when the float is embedded into the thixotropic material in a tube. The float diameter can vary along its length. The top surface of the float can be configured (e.g., shaped) to limit platelet adherence (e.g. conical or convex or other configuration). The surface of the float and/or the tube, or any portion thereof such as the top surface of the tube, can also be treated (e.g., with a coating, material, polymer, plastic, immobilized liquid (IL) layer, fluoropolymers, polytetrafluoroethylene (PTFE), perfluorocarbons, perfluorodecalin, perfluoroperhydrophenanethrene, almond oil, coconut oil, olive oil, canola oil, silicone oil, perfluoropolyethers, perfluorotripentylamines, tethered-liquid perfluorocarbon (TLP) IL layer, expanded polytetrafluoroethylene (ePTFE), or any combination thereof) to limit platelet adhesion. Examples of approaches for providing anti-adhesion surfaces are described by Irini Sotiri et al., Experimental Biology and Medicine (Maywood) (2016 May), 241(9): 909-918, although other materials can also be used to limit platelet adhesion in some embodiments of this disclosure. Advantageously, by preventing the adhesion of platelets to the float, it is possible to provide a plasma or platelet rich plasma with a higher concentration of platelets. The bottom surface of the float can be adapted to conform to the tube bottom. The surfaces of the float adjacent to the inner walls of the tube can be geometrically configured to improve the seal or barrier created by the tube, thixotropic material, and float (e.g. crenellations, grooves, sinusoidal in profile, protuberances, dimples, honeycomb, or other adaptations). The float can exhibit different geometries along its length (e.g. hypocycloid, multi-sided (three, four, five, six or more sides), bolt shaped (e.g. a larger diameter for a portion of the length and a smaller diameter for the remainder of the length), or other geometry). The float can be asymmetric in addition to those geometries set forth, for example, to better accommodate different centrifugation methods.

In certain embodiments, the float is comprised of a non-porous material and has a substantially smooth surface. In some embodiments, the float or a portion of the float comprises protrusions, comprises protuberances, comprises extensions, and/or is at least partially tooth-shaped (e.g., the float comprises protrusions, protuberances or extensions (which can be claw-shaped) at the bottom of the float), or any combination thereof, optionally wherein the protrusions, protuberances, extensions, tooth-like shape of a portion of the float, or any combination thereof are configured to provide additional surface area for contact and engagement between the float and the thixotropic material. For example, the additional surface area for contact, engagement, adherence, or any combination thereof between the float and the thixotropic material can be provided at a location where the float is intended or configured to contact the thixotropic material before centrifugation begins or at a location where the float is intended to contact the thixotropic material after centrifugation to form a barrier comprising the float and the thixotropic material, or any combination thereof.

In some embodiments, the biological sample is autologous. In some embodiments, the biological sample comprises mammalian blood. In some embodiments, the mammalian blood comprises human blood. In some embodiments, the biological sample comprises whole blood.

Still further embodiments provide a biological sample comprising a first component comprising, consisting essentially of, or consisting of a plasma fraction, and a second component comprising, consisting essentially of, or consisting of lymphocytes, monocytes, and erythrocytes. In some embodiments, a relative centrifugal force is applied for a time sufficient to form a barrier (e.g., formed by a portion of the float and the gel or thixotropic material) between the first component and the second component. In other embodiments, a relative centrifugal force is applied for a time sufficient to form a barrier between the plasma fraction and the second component comprising lymphocytes, monocytes, and erythrocytes.

In certain embodiments, the plasma fraction comprises platelets. In some embodiments, different fractions of the plasma fraction comprise different concentrations of plasma. As an example, in some embodiments, the plasma fraction comprises platelet rich plasma (PRP) and platelet poor plasma (PPP).

Some embodiments further comprise the step of removing at least a portion of the first component (e.g., a supernatant, which can be plasma, or second phase), to provide PPP for example, which can be further processed to provide PRP. This at least a portion (e.g., PPP) of the first component (e.g., a supernatant, which can be plasma) is typically removed from the top of the first component (e.g., plasma), while the remaining portion (e.g., PRP) is the portion of the first component (e.g., plasma) that remains after removing the at least a portion (e.g., PPP) of the first component (e.g., plasma). In some embodiments, the at least a portion (e.g., PPP) of the first component (e.g., plasma) makes up at least 25, 30, 35, 40, 45, 50, 55, 60, 65, 70, 75, 80, 85 or 90% by volume of the first component (e.g., plasma), no more than 25, 30, 35, 40, 45, 50, 55, 60, 65, 70, 75, 80, 85 or 90% by volume of the first component (e.g., plasma), or any combination thereof. Accordingly, in some embodiments, to create the PRP, from about twenty-five percent (25%) to about ninety percent (90%) of the first component is removed, optionally about thirty percent (30%) to about eighty-five percent (85%) of the first component is removed, about thirty-five percent (35%) to about eighty percent (80%) of the first component is removed, about forty percent (40%) to about seventy-five percent (75%) of the first component is removed, about forty-five percent (45%) to about seventy percent (70%) of the first component is removed, about fifty percent (50%) to about sixty-five percent (65%) of the first component is removed, optionally about fifty percent (50%), about sixty percent (60%), about seventy percent (70%), about eighty percent (80%), or about ninety percent (90%), of the first component is removed (e.g., thereby providing PPP). In some embodiments, the remaining portion (e.g., PRP) of the first component (e.g., plasma) that remains after removing the at least a portion (e.g., PPP) of the first component (e.g., plasma), makes up at least 10, 15, 20, 25, 30, 35, 40, 45, 50, 55, 60, 65, 70, 75, 80, 85 or 90% by volume of the plasma, no more than 10, 15, 20, 25, 30, 35, 40, 45, 50, 55, 60, 65, 70, 75, 80, 85 or 90% by volume of the plasma, or any combination thereof.

In some embodiments, a relative centrifugal force ("RCF") of from about 500 g to about 5000 g is applied to said tubular body. In other embodiments, an RCF of from about 750 g to about 5000 g is applied to said tubular body. While in other embodiments, an RCF of from about 1000 g to about 5000 g is applied to said tubular body. In yet other embodiments, an RCF of from about 1500 g to about 5000 g is applied to said tubular body. In some embodiments, an RCF of from about 2000 g to about 5000 g is applied to said tubular body. In some embodiments, an RCF of from about 2500 g to about 5000 g is applied to said tubular body. In some embodiments, an RCF of from about 3000 g to about 5000 g is applied to said tubular body. In other embodiments, an RCF of from about 3000 g to about 4000 g is applied to said tubular body. While in other embodiments, an RCF of from about 1500 g to about 2500 g is applied to said tubular body. In some embodiments, the RCF applied to said tubular body is at least 500, 750, 1000, 1250, 1300, 1350, 1400, 1450, 1500, 1550, 1600, 1650, 1700, 1750, 2000, 3000, 4000 or 5000 g; no more than 500, 750, 1000, 1250, 1300, 1350, 1400, 1450, 1500, 1550, 1600, 1650, 1700, 1750, 2000, 3000, 4000 or 5000 g; or any combination thereof.

The RCF forces are applied to said tubular body for a duration adequate to separate the sample components. As one skilled in the art would recognize, those durations will vary depending upon the sample to be separated, size of the tube, the RCF applied and other factors. In some embodiments, the RCF is applied for at least 4, 5, 6, 7, 8, 9, 10, 11, 12, 13, 14, or 15 minutes; no more than 5, 6, 7, 8, 9, 10, 11, 12, 13, 14, 15 or 30 minutes; or any combination thereof.

In some embodiments, the RCF creates a plasma-float-gel interface between a surface of the float-gel assembly and a surface of the plasma fraction. In some embodiments, the plasma-float-gel interface comprises platelets. In certain embodiments, the platelets in the plasma-float-gel interface are releasably bound to a surface of the gel. In some embodiments, agitation releases platelets from the plasma-float-gel interface. In some embodiments, the platelets released from the plasma-float-gel interface are suspended in the plasma fraction.

In some embodiments, the tubular body further comprises (or contains) an anticoagulant. In some embodiments, the anticoagulant is selected from: a citrate salt (e.g. buffered sodium citrate); an EDTA salt (potassium-ethylenediamine tetra-acid); citrate-theophylline-adenosine-dipyridamole (CTAD); hirudin, benzyl sulfonyl-d-Arg-Pro-4-amidinobenzylamide (BAPA); citric/citrate dextrose (ACD); heparin; an iodoacetate salt; an oxalate salt; a fluoride salt; and a combination of two or more thereof. In such embodiments, it is possible that the biological sample has been pre-treated with anticoagulant or the biological sample does not need to be anticoagulated.

Other embodiments provide compositions comprising a product of any one of the methods or systems described herein. Still further embodiments provide for the use of a composition comprising a product of any one of the methods or systems described herein for treating or preventing alopecia, bed sores, wrinkles, pain, tendonitis, arthritis, acne, scarring, crow's feet, orthopedic issues (e.g., ligament sprains and tears), and/or skin lesions.

Still further embodiments provide systems for separating components of a sample comprising: a sample; a tubular body; a means for applying RCF to said tubular body (e.g. a centrifuge); a thixotropic material; a float; and a means for agitating said tubular body. In some embodiments, the systems described herein further comprise a means for measuring color in a biological sample. In some embodiments, the means for measuring color in a biological sample is selected from a spectrophotometer and a densitometer. In some embodiments, the system comprises any component, device, or material described herein. In some embodiments, the system or any selection of the components of the system can be used to perform any method described herein.

In some embodiments, the centrifuge is selected from a fixed angle centrifuge, horizontal spin centrifuge, or a swinging bucket centrifuge.

In some embodiments, the means for agitating the tubular body is adapted to linearly agitate the tubular body. In some embodiments, the means for agitating the tubular body is a tube rocker.

Some embodiments of the present disclosure provide a system as described herein further comprising a platelet counter. Other embodiments further comprise a processor. In some embodiments, the processor is wirelessly coupled to the means for applying an RCF; the means for agitating the tubular body; the means for measuring color in a biological sample; and the platelet counter. In some embodiments, the means for applying an RCF; the means for agitating the tubular body; the means for measuring color in a biological sample; the platelet counter; and the processor are contained in a single apparatus.

As used herein, the term "available platelet count" (or "APC") is intended to refer to the number of platelets that are readily accessible to the clinician for administration to a subject in need thereof. As examples, the readily accessible platelets could be defined as consisting of or comprising (1) platelets that occur in a phase or portion of a phase that can be extracted and administered to a subject (e.g., intravenously administered to a human); (2) platelets that are above a barrier formed by a float, thixotropic material (e.g., gel) and the inner wall of a tubular body, optionally when an opening of the tubular body (e.g., test tube) is facing upwardly, optionally when the central axis or longitudinal axis or the length of the tubular body is vertically oriented; (3) platelets that are not trapped below the barrier formed by the float, thixotropic material and the inner wall of a tubular body or embedded in the barrier, optionally when an opening of the tubular body (e.g., test tube) is facing upwardly, optionally when the central axis or longitudinal axis or the length of the tubular body is vertically oriented or (4) a combination thereof. APC is expressed in units as the number of platelets per microliter.

In some embodiments, the methods and systems described herein increase the APC of plasma or PRP extracted from whole blood by at least about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% versus (i.e., relative to) the APC of plasma or PRP extracted from the whole blood by a control system. For example, if the APC count of the control system is X, the APC of plasma or PRP for some embodiments described herein can be X+100% of X, which equals 2X.

As used herein, "control system," as a first example, can mean a comparative plasma or PRP system, which comparative plasma or PRP system is defined relative to test system (e.g, any embodiment of a system disclosed herein) being examined with both used to extract plasma or PRP from a single sample of whole blood (e.g., a homogeneous sample of whole blood so that the initial samples of whole blood are essentially identical). Both the test plasma or PRP system and the comparative plasma or PRP system use the same centrifugal separator and are operated using the same conditions and configuration, except for the use or non-use of a separator float, and the configuration of the gel and separator float within the test plasma or PRP system. Accordingly, the test plasma or PRP system can comprise any combination of features possessed by the systems disclosed in the present disclosure while any one of, or any combination of the features can be omitted from the comparative plasma or PRP system. The comparative plasma or PRP tube has a size that is the same as the size of the test plasma or PRP tube. The comparative plasma or PRP system uses gel within the comparative plasma or PRP tube in an amount effective to separate the plasma from other portions of the whole blood after centrifugation but does not include a separator float. Meanwhile, the test PRP system uses the same gel and a separator float inside the test plasma or PRP tube, the gel being present in the test plasma or PRP tube in an amount effective, in combination with the separator float, to separate the plasma from other portions of the whole blood after centrifugation. Although the terms comparative plasma or PRP tube and test plasma or PRP tube are used for ease of identification, it is worthwhile to point out that for comparison purposes, the comparative plasma or PRP tube and the test plasma or PRP tube can be identical, although their contents (e.g., (i) thixotropic material (e.g., gel) versus thixotropic material (e.g., gel) and float, (ii) the volume of the thixotropic material (e.g., gel), (iii) type of thixotropic material, or (iv) any combination thereof) can be different or the same as desired. For comparison purposes, prior to centrifugation using the test plasma or PRP system and the comparative plasma or PRP system, a volume of the whole blood sample is placed in the test plasma or PRP tube of the test plasma or PRP system, and the same volume of the whole blood sample (e.g., as described in the Instructions for Use of the comparative plasma or PRP system) is placed in the comparative PRP tube of the comparative PRP system. Centrifugation of each whole blood sample occurs in the test plasma or PRP system and the comparative plasma or PRP system at a specified relative centrifugal force (rcf) (e.g., 500, 750, 1000, 1250, 1300, 1350, 1400, 1450, 1500, 1550, 1600, 1650, 1700, 1750, 2000, 3000, 4000 or 5000 g; in accordance with the instructions for use of the comparative plasma or PRP system; in accordance with a relative centrifugal force specified for any embodiment of the present application; or any combination thereof) for a set period of time (e.g., 5, 6, 7, 8, 9, 10, 11, 12, 13, 14 or 15 minutes; in accordance with the instructions for use of the comparative plasma or PRP system; in accordance with a centrifugation time specified for any embodiment of the present application; (i) for a comparative plasma or PRP system centrifugation time sufficient to separate the red blood cells and plasma in the comparative plasma or PRP system and (ii) for a test plasma or PRP system centrifugation time sufficient to separate the red blood cells and plasma in the test plasma or PRP system, respectively; or any combination thereof). After centrifugation is performed for a set period of time or a time sufficient to separate the second component (e.g., red blood cells) and the first component (e.g. plasma) in the comparative plasma or PRP system and the test plasma or PRP system, the first component (e.g., plasma or second phase) is located above the barrier comprising the thixotropic material. Next, (i) the entirety of the first component (e.g., plasma) can be agitated (to suspend platelets) and withdrawn from each of the test plasma or PRP system and the comparative plasma or PRP system; or (ii) a supernatant or top portion (e.g. PPP) of the first component (e.g., plasma) can be removed from each of the comparative plasma or PRP system and the test plasma or PRP system to leave behind a remaining portion (e.g., PRP) of the first component. The supernatant or top portion (e.g., PPP) of the first component can be an amount in accordance with the instructions for use of the comparative plasma or PRP system; can be an amount in accordance with any embodiment described in this disclosure; can make up at least 25, 30, 35, 40, 45, 50, 55, 60, 65, 70, 75, 80, 85 or 90% by volume of the first component (e.g., plasma); can make up no more than 25, 30, 35, 40, 45, 50, 55, 60, 65, 70, 75, 80, 85 or 90% by volume of the first component (e.g., plasma); or any combination thereof. If proceeding with the option in which the supernatant or top portion of the first component is removed, then (i) the remaining portion (e.g., PRP) from the comparative plasma or PRP system and (ii) the remaining portion (e.g., PRP) from the test plasma or PRP system is agitated (e.g., in accordance with the Instructions for Use of the comparative plasma or PRP system; is agitated by being oscillated about a starting point along a vertical axis at an amplitude of three inches above the starting point and three inches below the starting point at a rate of 4 complete oscillations per second for 10, 20, 30, 40, 50, 60, 70, 80, 90, 100, 110 or 120 seconds, is agitated in accordance with any embodiment in this disclosure; or any combination thereof). After obtaining either the first component (e.g., plasma) after agitation of the first component or the remaining portion (e.g., PRP) after agitation of the remaining portion, a comparison can be made of the number of platelets per microliter or available platelet count (APC) of (i) the plasma or PRP of the comparative plasma or PRP system and (ii) the plasma or PRP of the test plasma or PRP system. After performing this protocol, the number of platelets per microliter or APC of the volume of the plasma or PRP extracted from the control system can be defined as a comparative platelet concentration or APC count equal to X. Meanwhile, the platelet concentration or APC count of the volume of the plasma or PRP extracted using some embodiments of the test PRP system described herein can be defined as an test platelet concentration or APC count equal to X+A*X, where A is at least about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%; and optionally where A can be up to about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. Further improvements are expected to be possible with the embodiments described herein.

As used herein, "control system," as a second example, can mean a comparative system, which comparative system is defined relative to the test system being examined with both used to separate plasma from a single sample of whole blood (e.g., a homogeneous sample of whole blood so that the initial samples of whole blood are essentially identical). Both the test system and the comparative system use the same centrifugal separator. The test system can comprise any combination of features possessed by the systems disclosed in the present disclosure (e.g., the use of a separator float, for example, the claw-shaped float of FIG. 11, the configuration of the gel in the test system, the configuration of the separator float within the test system, or any combination thereof) while any one of, or any combination of the features are omitted from the comparative system. The comparative system may be a gel only system available in the market. The comparative system uses gel within the comparative tube in an amount effective to separate the plasma from other portions of the whole blood after centrifugation but does not also include a separator float. Meanwhile the test system uses gel and a separator float, the gel being present in the test system in an amount effective, in combination with the separator float, to separate the plasma from other portions of the whole blood after centrifugation. Although the terms comparative system and test system are used for ease of identification, it is worthwhile to point out that for comparison purposes, the comparative tube and the test tube can be identical, although their contents (e.g., (i) thixotropic material (e.g., gel) versus thixotropic material (e.g., gel) and float, (ii) the volume of the thixotropic material (e.g. gel), (iii) type of thixotropic material (e.g. gel), or (iv) any combination thereof) can be different or the same as desired. For comparison purposes, prior to centrifugation using the test system and the comparative system, a volume of the whole blood sample is placed in the test system tube and the volume of the whole blood sample as described in the Instructions for Use (IFU) is placed in the comparative system tube of the comparative system. Then, after centrifugation sufficient to accomplish separation of the blood in the comparative system in accordance with the IFU of the comparative system or any embodiment described in this disclosure and the test system in accordance with the IFU of the comparative system or any embodiment described in this disclosure and after agitation is performed with the test system, the comparative system, or both in accordance with the IFU of the comparative system or any embodiment described in this disclosure, the resulting plasma is extracted from both the test system tube and the comparative system tube. (Note: examples of removing plasma, PPP, or PRP are provided herein and techniques can also be provided in Instructions for Use of the comparative system. For purposes of the comparison, the quantity of plasma removed can be a fixed percentage from the top of the plasma phase of both the test system and the comparative system using the same removal protocol. The fixed percentage can be any percentage described in this disclosure, for example, at least 25, 30, 35, 40, 45, 50, 55, 60, 65, 70, 75, 80, 85 or 90% by volume of the plasma; no more than 25, 30, 35, 40, 45, 50, 55, 60, 65, 70, 75, 80, 85 or 90% by volume of the plasma; or any combination thereof. By comparing platelet count results in the unit volumes of plasma in the test system and the comparative system obtained after following the IFU of the comparative system, the steps for any embodiment described herein, or both, respectively, valid comparisons can be made.) After performing this protocol, the resulting platelet count provides the available platelet count (APC) of the comparative system and the test system, respectively. The APC in a unit volume from the comparative system can be defined as a comparative APC count equal to X. Meanwhile, the APC in the same unit volume using some embodiments of the test system described herein can be defined as an test APC count equal to $X+A*X$, where A is at least about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%; and optionally where A can be up to about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. Further improvements are expected to be possible with the embodiments described herein.

In some embodiments, the methods and systems described herein provide a product (e.g., PRP) having an APC of greater than about 375,000 platelets/microliter, about 400,000 platelets/microliter, about 425,000 platelets/microliter, about 450,000 platelets/microliter, about 475,000 platelets/microliter, about 500,000 platelets/microliter, about 525,000 platelets/microliter, about 550,000 platelets/microliter, about 575,000 platelets/microliter, about 600,000 platelets/microliter, about 625,000 platelets/microliter, about 650,000 platelets/microliter, about 675,000 platelets/microliter, about 700,000 platelets/microliter, about 725,000 platelets/microliter, about 750,000 platelets/microliter, about 775,000 platelets/microliter, about 800,000 platelets/microliter, about 825,000 platelets/microliter, about 850,000 platelets/microliter, about 875,000 platelets/microliter, about 900,000 platelets/microliter, about 925,000 platelets/microliter, about 950,000 platelets/microliter, or about 975,000 platelets/microliter. In some embodiments, the methods and systems described herein provide a product (e.g., PRP) having an APC within a range whose endpoints are any APC listed in this paragraph.

Other embodiments provide methods for: suspending platelets in a post-centrifugation biological sample (or centrifuged biological sample); increasing APC in a biological sample or portion thereof (e.g., separating a biological sample into (i) a platelet-rich plasma (PRP) with an increased APC relative to the biological sample and (ii) a remainder of the biological sample); and/or enriching the platelet count in a biological sample or portion thereof (e.g., separating a biological sample into (i) a platelet-rich plasma (PRP) with an increased platelet count relative to the biological sample and (ii) a remainder of the biological sample). In some embodiments, the methods comprise: centrifuging a collection tube containing a biological sample, a float and a thixotropic gel; and agitating the collection tube at an angle and rate effective to create a layer of foam on top of said biological sample. Optionally, the methods use any system, any component of a system, or any combination of components of a system described herein.

FIG. 1 depicts an embodiment of a tube for separating components of a sample, post-centrifugation of a biologic sample. As shown, tube 100, includes an inner surface 107 which defines an inner diameter D; and an outer surface 108.

In some embodiments, inner surface 107 is coated with a material. In some embodiments, inner surface 107 is coated with an inert material, e.g. silicon dioxide. In some embodiments, inner surface 107 is coated with an anticoagulant 106 or the anti-coagulant 106 is disposed within the tube. Tube 100 can be made from any material known in the art capable of receiving and maintaining a sample (e.g. a liquid biological sample, such as human blood) before, during and after centrifugation. FIG. 1 further depicts float 103, which can be of various shapes and sizes. As depicted herein, the lower portion (e.g., bottom) of the float 103 is claw-shaped. As further depicted, the float 103 below the top surface is encompassed, encased, surrounded or a combination thereof by the thixotropic material 101. The claw-shaped portion of the float can be useful to provide additional surface area for the thixotropic material to engage the float. Without being bound by theory, it is believed that the greater surface area can help provide a stronger seal between some floats and thixotropic materials. FIG. 1 also depicts various components of a sample (e.g. human blood) post-centrifugation. In particular, as depicted in FIG. 1, tube 100 contains a red blood cell component 102 and a plasma component 105, which contains—inter alia—platelets. Tube 100 also includes a stopper 104, which can be configured to maintain vacuum within the tube 100 for extended periods of time (e.g. 18-36 months). A plasma-float-thixotropic material interface 106 can play a role in platelet capture and performance of the systems and apparatus described herein.

Figure 2:
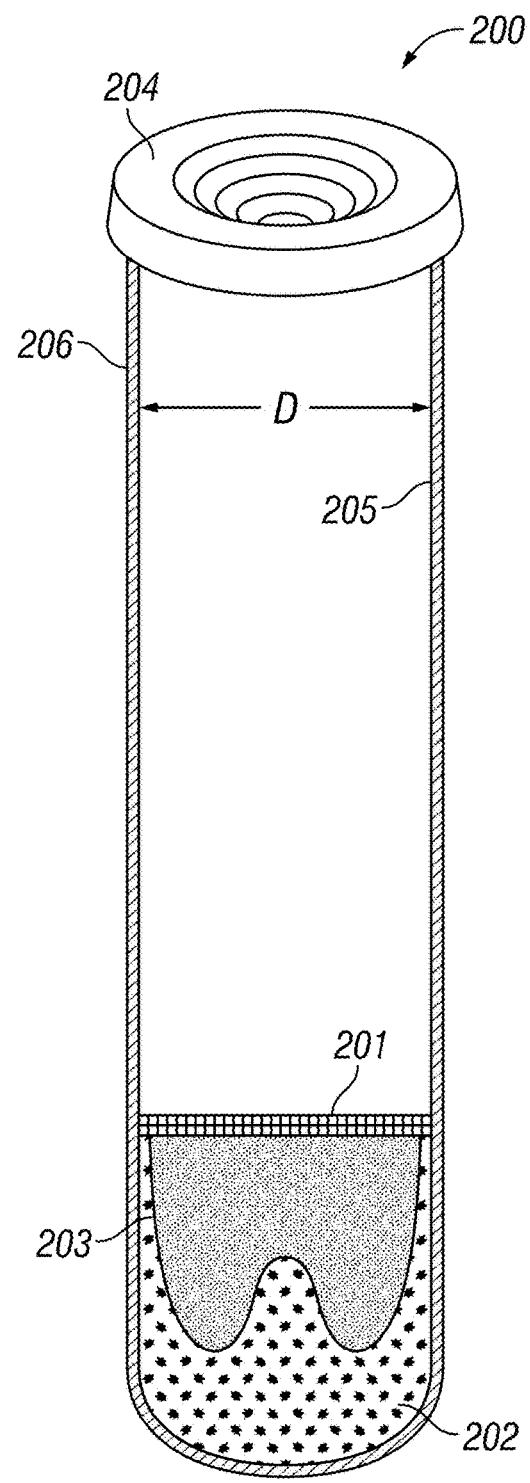
FIG. 2 depicts a partial cross section view of an embodiment of a tube for separating components of a sample, prior to introduction of a biological sample and pre-centrifugation.

FIG. 2 depicts an embodiment of a tube for separating components of a sample, prior to admission of a biologic sample and pre-centrifugation. As shown, the float 203 and thixotropic material 202 are configured to remain in place within the tube 200 during transport. In some embodiments, the thixotropic material 202 and the float 203 remain in a substantially fixed position within tube 200 during transport. Examples of a substantially fixed position within the tube during transport means that the thixotropic material, during transport, is not flowable, engages with the inner surface of the tubular body (e.g., tube 200) so that the thixotropic material remains stationary relative to the inner surface of the tubular body, and the float is embedded in the thixotropic material and also remains stationary relative to the inner surface of the tubular body. In some embodiments, it can be acceptable for the thixotropic material and float to move somewhat relative to the tubular body. For example, in some embodiments, no point on the float, no boundary of the thixotropic material, or neither moves along a central axis or length of the tube by more than 15, 10, 9, 8, 7, 6, 5, 4, 3, 2 or 1% of the length of the float along the longitudinal axis or the central axis or the length of the float prior to centrifugation. Tube 200 also has an inner surface 205 which defines an inner diameter D; and an outer surface 206. Tube 200 includes a stopper 204, which can be configured to maintain vacuum within tube 200 for extended periods of time (e.g. 18-36 months). Tube 200 also includes anticoagulant 201. In some embodiments, the anticoagulant can be any anticoagulant known in the art suitable for use with products designed for human use.

Figure 3A:
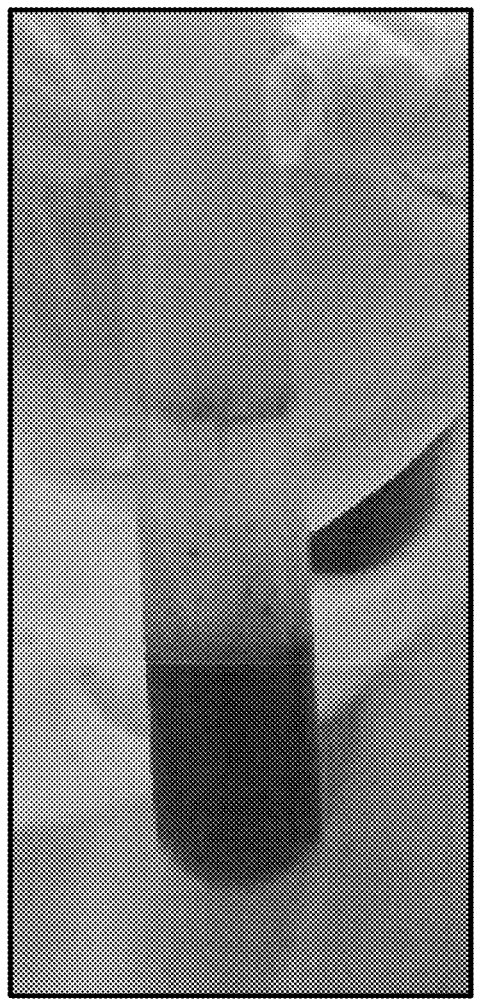
FIGS. 3A and 3B depict embodiments of tubes for separating components of a sample, post-centrifugation.
Figure 3B:
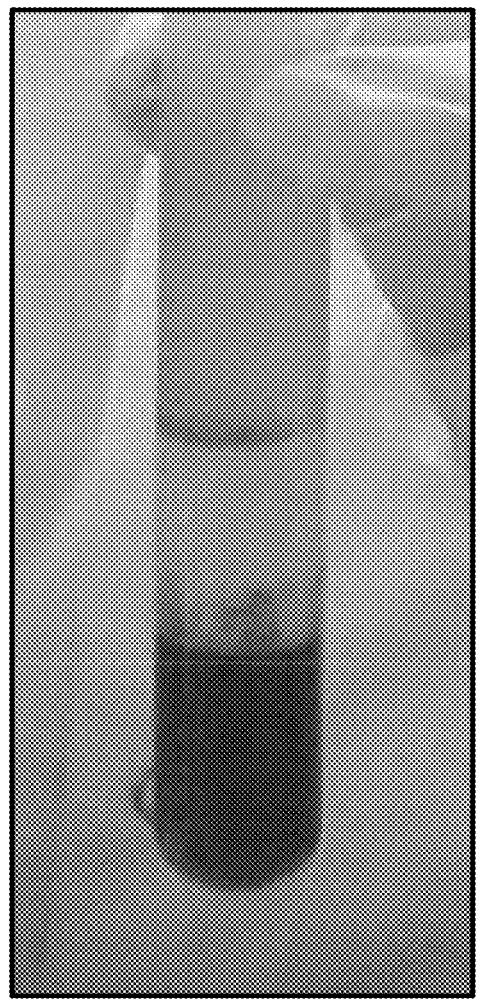

FIG. 3A and FIG. 3B illustrate how a system comprising a float and a gel can be used to separate blood cells (in the lower portion of the tube) and platelet-rich plasma (PRP) (in the upper portion of the tube) following centrifugation.

FIG. 4A depicts a system (i.e. system in which the tubular body was subject to centrifugation at a fixed angle between vertical and horizontal) wherein an amount of thixotropic material M is observed above the float post-centrifugation. This can occur, for example, when the system includes too much gel while the density of the gel is equal to or near the density of the float, or if the initial configuration of the system includes gel above the top surface of the float and if the system is not subject to centrifugation for enough time to reach a position that is closer to equilibrium position in which a gel is positioned below the top surface of the float. As one skilled in the art would appreciate, this thixotropic material can adversely impact platelet capture, thereby reducing the performance of a separation system. As such, comparing the post-centrifugation results of FIG. 4A (less preferable results with an embodiment of the disclosure) to FIG. 4B (more preferable results with an embodiment of the disclosure) highlights the effect of the combination of features developed by the present inventors and that despite some embodiments being more preferable than other embodiments, various embodiments are useful to achieve separation of a whole blood sample into blood and PRP.

Figure 5:
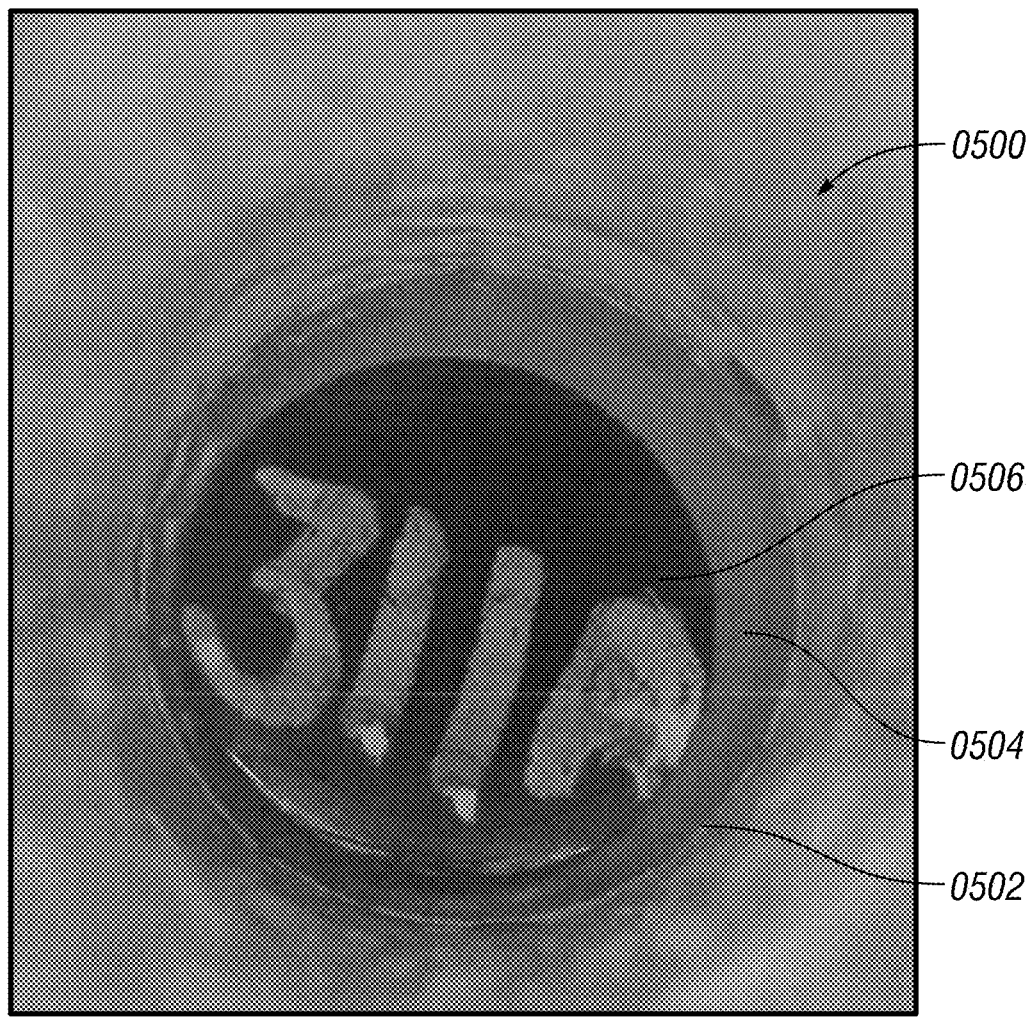
FIG. 5 is a top perspective view of an embodiment of a float-gel barrier created post-centrifugation by an embodiment of a method and system of the present disclosure.
Figure 10:
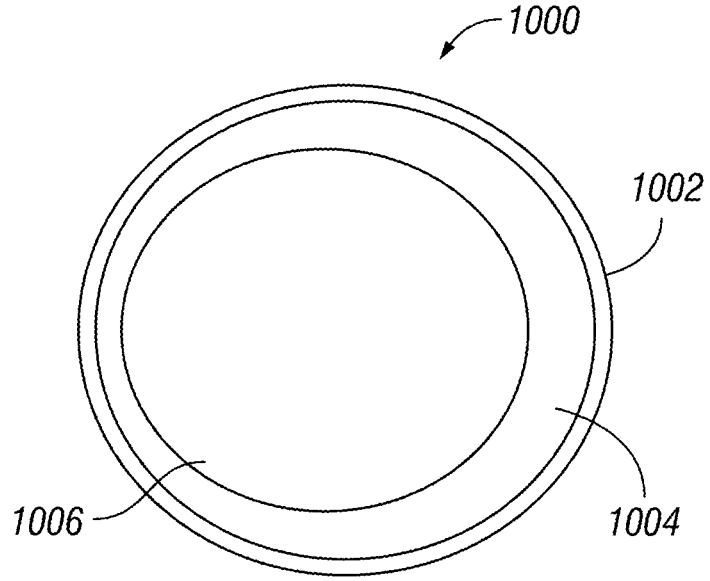
FIG. 10 depicts a top view of one embodiment of a float without protuberances within a tube in accordance with some embodiments of the present disclosure.

FIG. 5 illustrates an embodiment of a system 0500 comprising a float 0506 surrounded by thixotropic material 0504 (e.g., gel). The thixotropic material is positioned between the float and the inner surface of a tubular body 0502 (e.g., tube) to provide a barrier or seal. FIG. 10 also illustrates an embodiment of a system 1000 comprising a float 1006 surrounded by thixotropic material 1004 (e.g., gel). The thixotropic material is positioned between the float and the inner surface of a tubular body 1002 (e.g., tube) to provide a barrier or seal.

Figure 6:
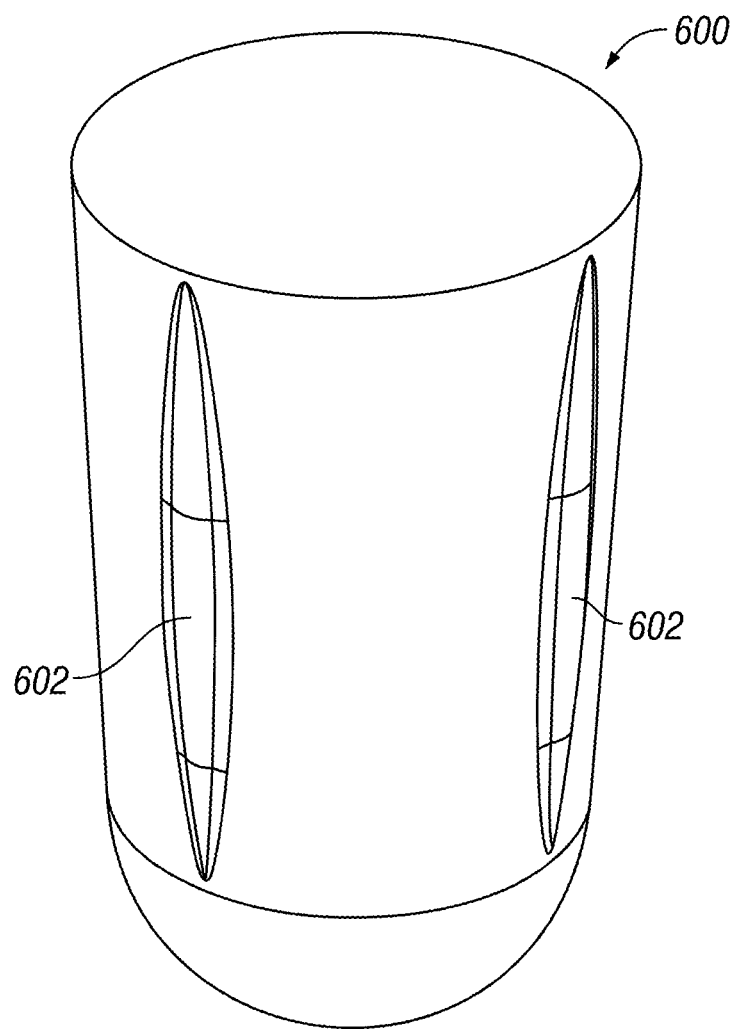
FIG. 6 depicts a float according to some embodiments of the present disclosure.

FIG. 6 illustrates an embodiment of a float design having a bullet-like shape. As can be seen, the float 600 comprises an optional protuberance 602 as part of an optional plurality of protuberances 602 that extend from the surface of the float adjacent to the inner wall of the tube. As depicted, each protuberance forms a ridge. While the float 600 depicts the protuberances as longitudinal ridges, the plurality of protuberances on a float can be in such geometries and located at such points around the surface of the float adjacent to the inner surface of the tube such that the float longitudinal axis or length or central axis aligns with the tube longitudinal axis or length or central axis. The bottom portion of the float can be adapted to conform to the bottom of the tube. As depicted, each protuberance 602 is also configured for its length to be oriented substantially vertically when the float 600 is floating freely in a tube having a vertically oriented central axis. The ridge can be interrupted along its length so that gel more easily envelops the surface of the float. The protuberances provide additional surface area for gel adherence. However, the length of each protuberance can also be oriented tangentially to the outer surface of the float 600 or oriented at up to a selected offset angle (e.g., no more than 30, 25, 20, 15, 10, 9, 8, 7, 6, 5, 4, 3, 2 or 1 degrees) from tangent to the outer surface of the float. In some embodiments, the length of each protuberance can be offset from a central axis of the float by an angle (e.g., no more than 30, 25, 20, 15, 10, 9, 8, 7, 6, 5, 4, 3, 2 or 1 degrees).

Advantageously, the protuberances 602 along the side of the float add stability and help to ensure a good seal by more or less aligning the longitudinal axis or length or central axis of the float along the tube longitudinal axis central axis or length and thus enabling the gel or thixotropic material to better encircle the float. Accordingly, the protuberance length and extension from the float surface can also be configured so that the central axis of the float is oriented within a selected tolerance angle (e.g., no more than 30, 25, 20, 15, 10, 9, 8, 7, 6, 5, 4, 3, 2 or 1 degrees) from parallel to the central axis of the tube when the float floats freely in a tube having a vertically oriented central axis.

As illustrated, the diameter of the float, including the protuberances, is configured to be less than the diameter of the tube. This is a distinguishing feature of some embodiments disclosed herein relative to floats having a float diameter, whether with ridges or without ridges, that equals or exceeds the tube inner diameter. An additional distinguishing feature of some of the embodiments disclosed relative to other systems is the simpler combined use of gel or a thixotropic material in combination with the float as compared to other systems that require (i) one or a plurality of gel ports in a device; (ii) at least two pieces that move relative to each other; (iii) at least two pieces where each piece has a different density than the other piece; (iv) an aperture or channel configured to allow material to pass through the device from top to bottom or bottom to top or both during centrifugation; (v) a plunger to squeeze material out of the ports; (vi) a bladder, one or a plurality of ports, a piston, other mechanism or combination thereof to discharge gel from the device during centrifugation, for example, by crushing gel pellets, using a mechanism to eject gel from the device during centrifugation, or any combination thereof; (vii) or any combination thereof.

In contrast, embodiments of a float according to the present disclosure optionally (i) can be made of a single piece or multiple pieces that are configured to be fixed and immobile relative to each other, (ii) can be made of a solid construction (e.g., solid phase as opposed to being a liquid or gas, solid in the sense of being filled and not hollow, or any combination thereof) without apertures (e.g., ports or thixotropic material ports), without an inner void, or without any combination thereof, (iii) can be made with a hollow construction provided by an inner void and having no aperture or port to connect the inner void to the exterior of the float, (iv) can be made of a single piece or a plurality of pieces that are all made of the same material or materials and configured to have the same density within +/−10, 9, 8, 7, 6, 5, 4, 3, 2 or 1% of the density of the more dense piece, or (v) any combination thereof.

A third distinguishing feature of some embodiments disclosed herein relative to other floats is that deformation of the float or tube during centrifugation and the corresponding precision engineering and manufacturing required in a float only PRP tube, is not required. For example, comparative floats can have a diameter that is as large as or larger than the inner diameter of a tube when the float is not compressed or subject to centrifugation. Accordingly, these comparative floats can require the application of centrifugation to reduce the diameter of the comparative floats or radially expand the tube and enable the comparative floats to move along the length of the tube. In contrast, embodiments described herein can be provided with an outer diameter (e.g., the diameter corresponding to a circle that circumscribes the float and any protuberances or ridges) that is smaller than the inner diameter of a tube and therefore not dependent on tube radial expansion, float compression, or a reduced float diameter caused by centrifugation to be able to move along the length of a tube. Nonetheless, the embodiments disclosed herein can have an outer diameter (e.g., the diameter corresponding to a circle that circumscribes the float and any protuberances or ridges) that is configured to be large enough that the central axis of the float is oriented within a selected tolerance angle (e.g., no more than 30, 25, 20, 15, 10, 9, 8, 7, 6, 5, 4, 3, 2 or 1 degrees) from parallel to the central axis of the tube when the float floats freely in a tube having a vertically oriented central axis.

Figure 7B:
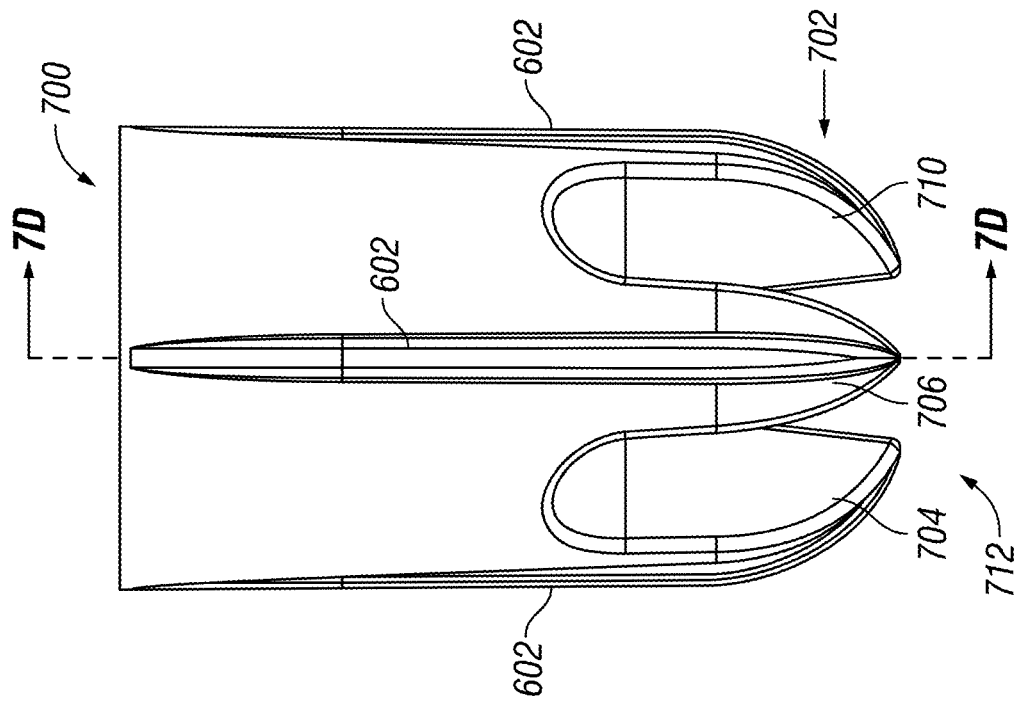
FIGS. 7A-7D depict various views of an alternative embodiment of a float according to some embodiments of the present disclosure.
Figure 7A:
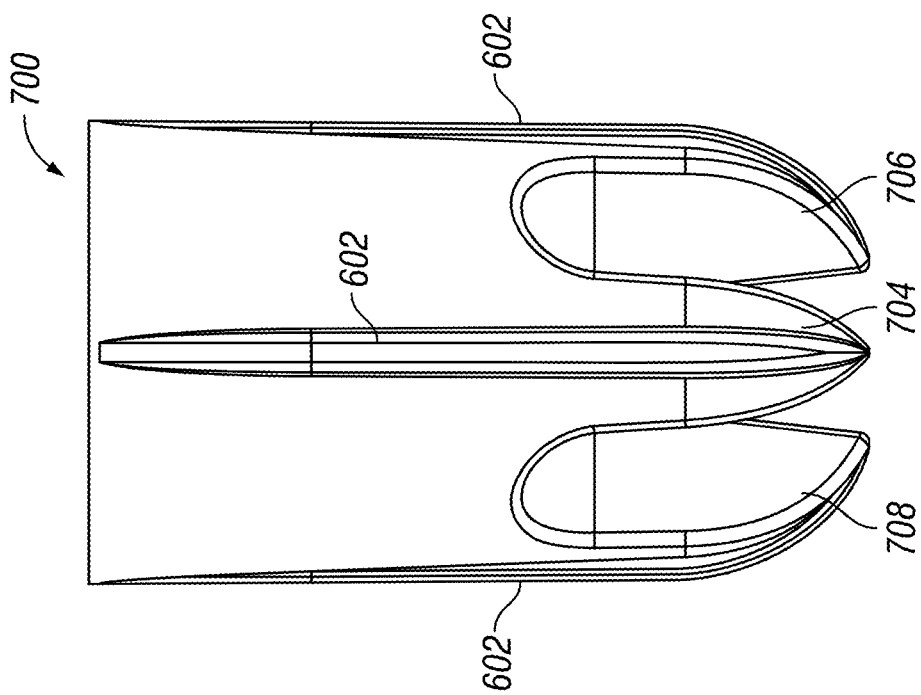
Figure 7C:
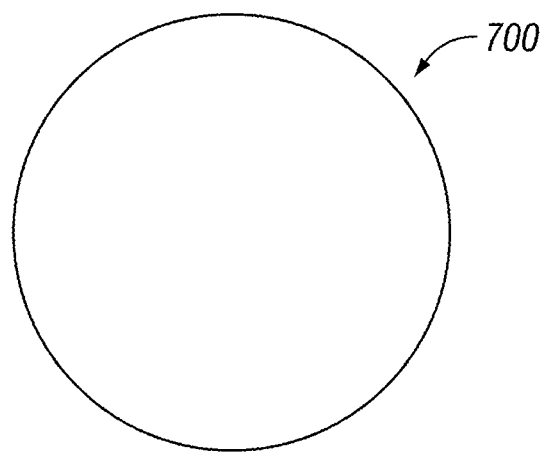
Figure 7D:
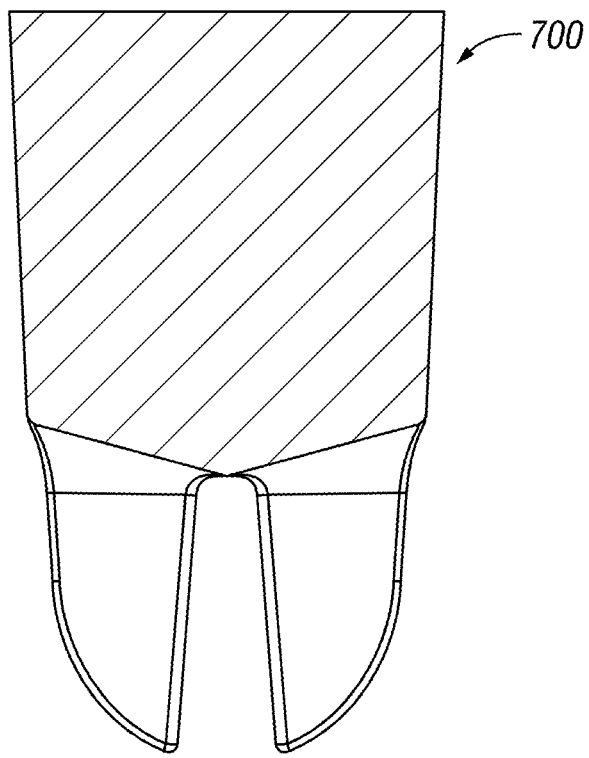

FIG. 7A depicts a side view of an embodiment of a float 700 of the present disclosure, a lower portion 702 of the float (which includes, for example, the bottom portion 712 of the float) having four claw-shaped protrusions 704, 706, 708, 710 and having protuberances 602 (e.g., four ridges, optionally one or more for each claw-shaped protrusion) along the outer surface of the float. FIG. 7B depicts a side view of the float of FIG. 7A rotated about its axis 90 degrees. FIG. 7C is a top plan view of the float of FIG. 7A. FIG. 7D is a sectional view of the side of the float of FIG. 7A. The location of the section shown in FIG. 7D is illustrated in FIG. 7B.

Figure 8B:
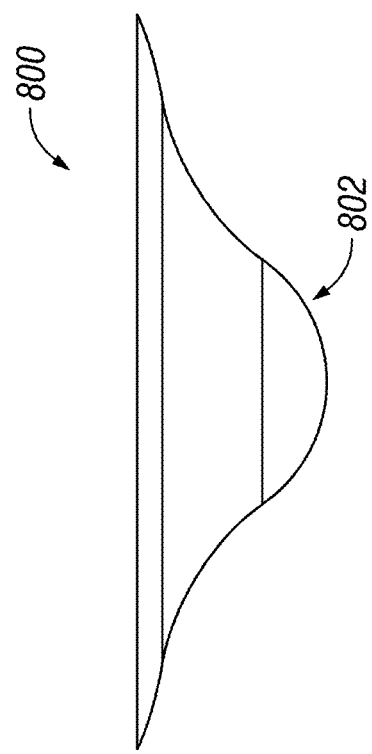
FIGS. 8A and 8B depict an alternative embodiment of a float according to some embodiments of the present disclosure.
Figure 8A:
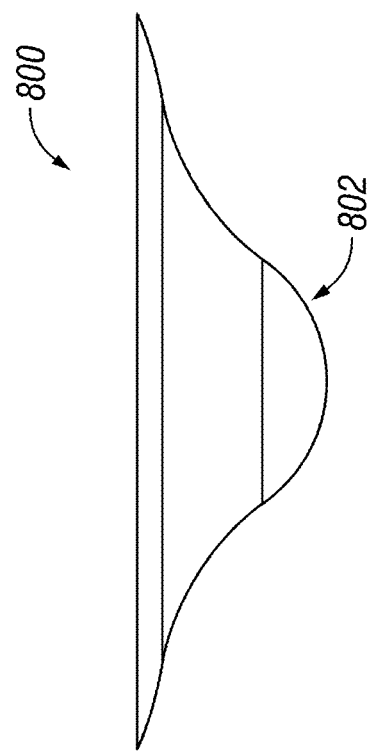

FIG. 8A depicts a side view of an embodiment of a float 800 of the present disclosure, the opposite side being a mirror image of FIG. 8A. As can be seen in FIG. 8A, a lower portion 802 of the float has a bell-like shape. FIG. 8B depicts a side view of the float of FIG. 8A rotated about its axis 90 degrees, the opposite side of the float being a mirror image of FIG. 8B.

Figure 9:
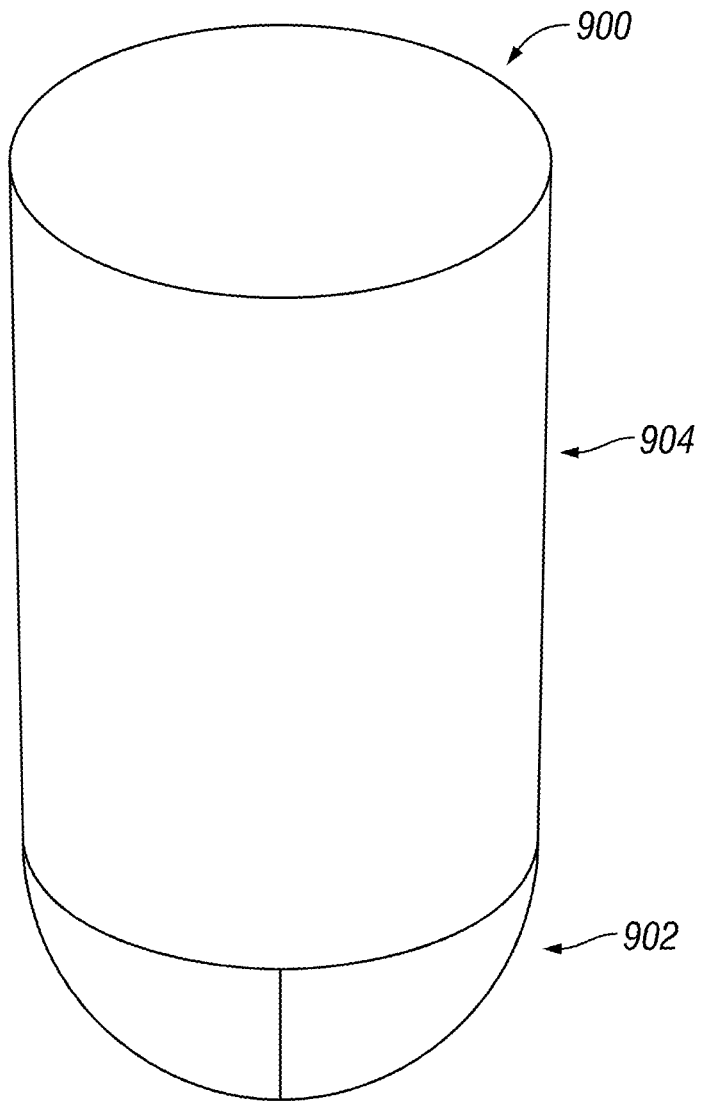
FIG. 9 depicts an alternative embodiment of a float according to some embodiments of the present disclosure.

FIG. 9 depicts a perspective view from the top of an embodiment of a float 900 of the present disclosure, a lower portion 902 of the float having a hemispherical shape and an upper portion 904 of the float having a cylindrical shape, which, in some embodiments, can be somewhat inwardly tapered from top to bottom to provide the upper portion 904 with the shape of a truncated cone. As can be seen, in some embodiments, the float 900 as a whole, resembles a bullet shape. The lower portion can be shaped to conform with the tube geometry. Additionally, as illustrated in FIG. 9, in some embodiments, the float can comprise a plurality of pieces.

Figure 17:
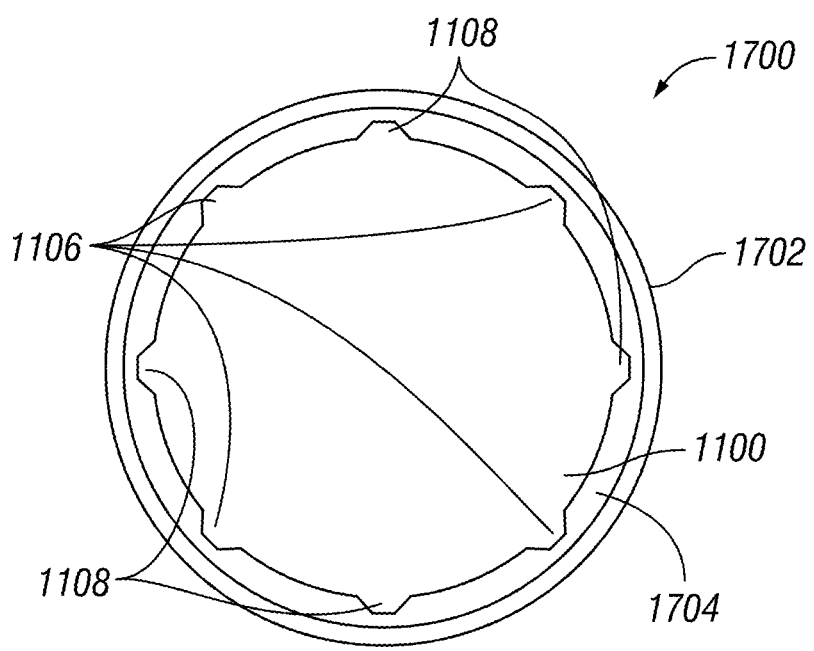
FIG. 17 depicts a top view of the embodiment of the float of FIG. 11 placed in a tubular body with a thixotropic material.

FIG. 10 depicts a system 1000 comprising an embodiment of a float 1006 without features corresponding to local recesses or protrusions on the outer surface of the float (e.g. protuberances or ridges). that the float is circumferentially surrounded by thixotropic material 1004, which along with the float 1006 and the inner surface of a tubular body 1002, forms a barrier. For example, this barrier can be used to separate two phases of a sample. As can be seen in FIG. 10, the central axis of the float 1006 is not concentric with the central axis of the tubular body 1002. This configuration can be less preferable for forming an impermeable or substantially impermeable barrier when compared to a system in which the float and a central axis of the tubular body are closer to being concentric, for example, as illustrated in FIG. 17. Nonetheless, such an embodiment can still function and provide improvements relative to existing systems.

Figure 11:
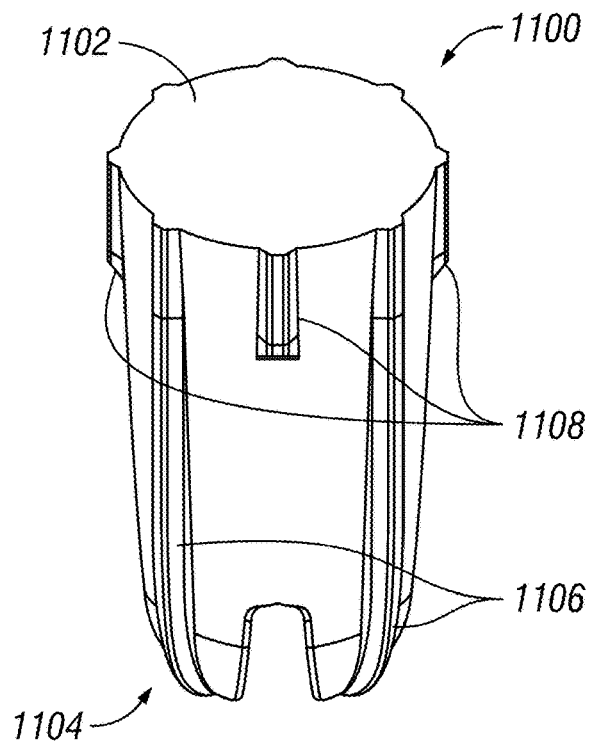
FIG. 11 depicts a top perspective view of an embodiment of a float with protuberances in accordance with some embodiments of the present disclosure.
Figure 12:
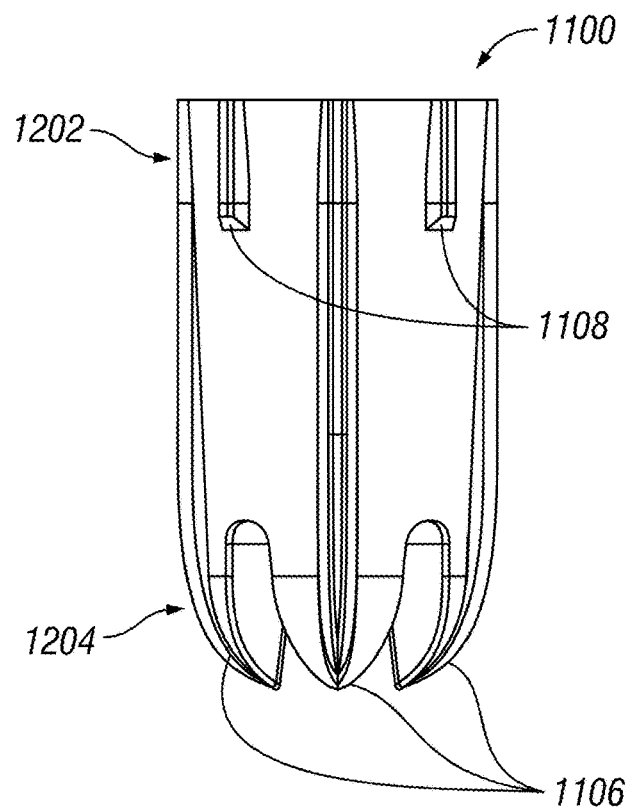
FIG. 12 depicts a side view of the float of FIG. 11.
Figure 13:
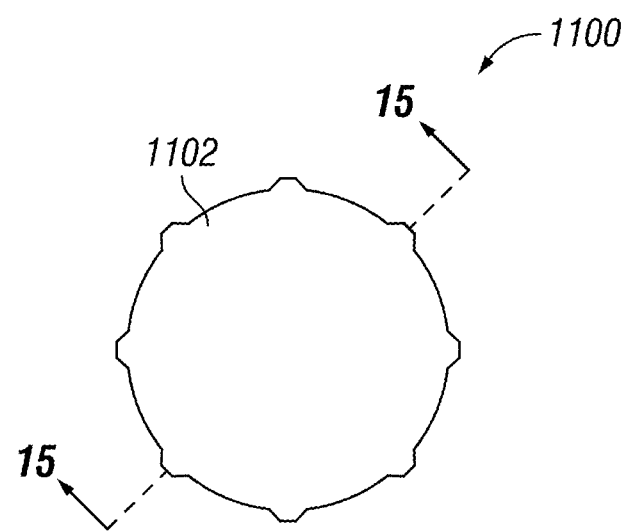
FIG. 13 depicts a top plan view of the float of FIG. 11.
Figure 14:
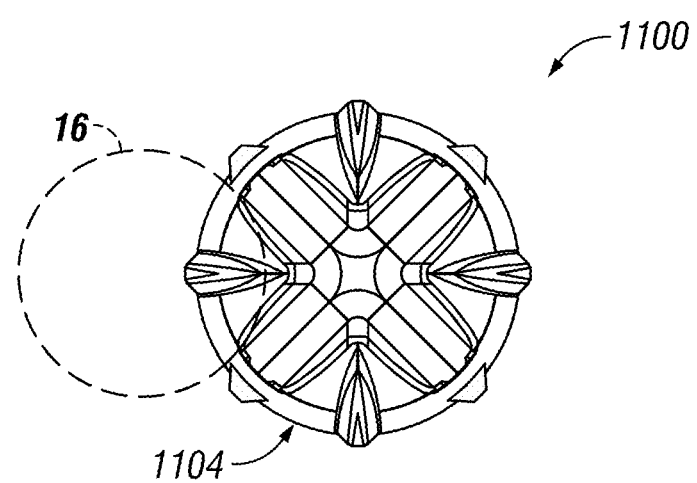
FIG. 14 depicts a bottom plan view of the float of FIG. 11.
Figure 15:
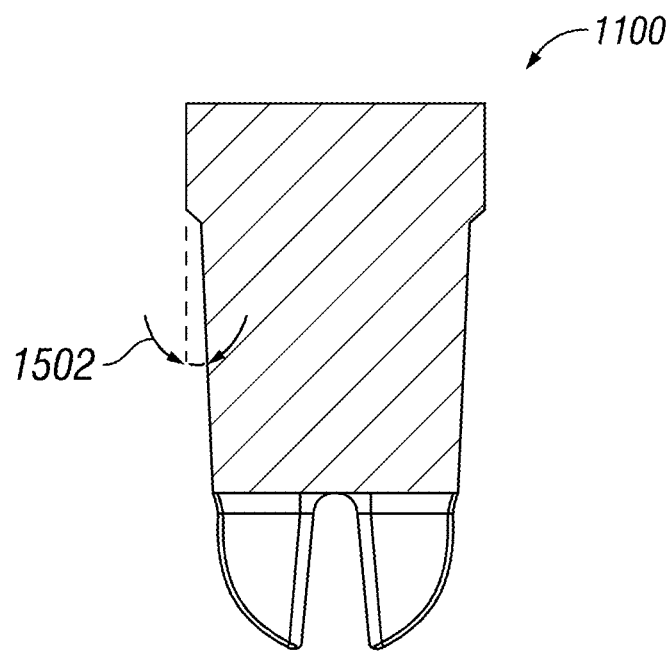
FIG. 15 depicts a sectional view of the float of FIG. 11 taken in the direction of the arrows shown in FIG. 13 and along the plane illustrated in FIG. 13.
Figure 16:
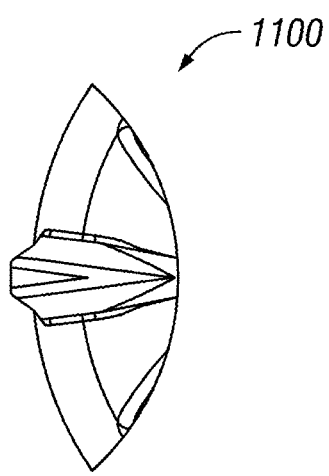
FIG. 16 depicts a detail view of the float of FIG. 11 at the location identified in FIG. 14.

FIGS. 11 to 16 depict an embodiment of a float 1100 comprising protuberances. As illustrated in FIGS. 11 and 12, the float 1100 comprises a lower portion 1104, 1204 comprising claw-like protrusions, a first set of protuberances 1106 (e.g., a set of longer protuberances or ridges), and an upper portion 1202 comprising a second set of protuberances 1108 (e.g., set of shorter protuberances or ridges). FIG. 13 illustrates the top surface 1102 of the float. FIG. 14 illustrates the bottom surface 1104 of the float. FIG. 15 illustrates a sectional view of the float 1100 taken along the plane as depicted in FIG. 13. FIG. 16 illustrates a detail at the location illustrated in FIG. 14.

FIG. 17 depicts a top view of the float of FIG. 11 inside a tube. As illustrated, the float 1100 is circumferentially surrounded by thixotropic material 1704. Additionally, as illustrated, the float 1100, the thixotropic material 1704 and the inner surface of a tubular body 1702, form a barrier. As an example, the barrier can be used to separate a first phase and a second phase of a sample after centrifugation of the sample. FIG. 17 illustrates how protuberances 1106, 1108 can be used to help align the central axis of the float with the central axis of the tubular body, which can be preferable for forming an impermeable or substantially impermeable barrier when compared to a float that is less concentric with the tubular body, for example, as illustrated in FIG. 10.

Other embodiments of the float, having other shapes, sizes, or combinations thereof, are also possible.

For avoidance of doubt, at least a portion of any one of the methods described herein could be suitable for use with any one of the apparatus described herein, or in any one of the systems described herein.

Statements of the Disclosure include:

Statement 1: A system for separating components of a sample, the system comprising: an apparatus comprising: a tubular body for receiving a liquid biological sample; a thixotropic material; and a float comprising: a core; a top surface; and a bottom surface; wherein the float has a specific gravity less than or equal to the specific gravity of the thixotropic material; optionally wherein the thixotropic material is positioned along a bottom inner surface of the tubular body; optionally wherein the thixotropic material is engaged (e.g., adhesively, frictionally, or a combination thereof) with the bottom inner surface of the tubular body; optionally wherein a portion of the float (e.g., bottom portion of the float) is embedded in the thixotropic material; optionally wherein the float and thixotropic material are configured to remain in place within the tubular body during transport (e.g., at 25° C. and 101.325 kPa); optionally the thixotropic material is configured so that at 25° C. and 101.325 kPa: (i) the thixotropic material is not flowable, (ii) the thixotropic material engages (e.g., adhesively, frictionally or a combination thereof) with the bottom inner surface of the tubular body (e.g., so that the thixotropic material remains stationary or essentially stationary relative to the bottom inner surface of the tubular body under the force of gravity), (iii) when the float is embedded in the thixotropic material, the float remains stationary or essentially stationary relative to the bottom inner surface of the tubular body under the force of gravity, or (iv) a combination thereof; optionally the float is solid; optionally the float is a single, integral piece; optionally the float is non-porous; optionally the float is configured not to deform under any value, range or combination of ranges of relative centrifugal force described in this disclosure; optionally the float comprises a plurality of mutually spaced protuberances (e.g., ridges); and optionally the protuberances or ridges are longitudinally oriented within 30, 25, 20, 15, 10, 9, 8, 7, 6, 5, 4, 3, 2 or 1 degrees of parallel to a central axis, longitudinal axis, length or combination thereof of the float).

Statement 2: The system according to Statement 1, wherein the float has a specific gravity less than the specific gravity of the thixotropic material.

Statement 3: The system according to Statement 1 or Statement 2, wherein the float has a diameter less than or equal to the inner diameter of the tubular body, optionally wherein the float has a diameter that is at least 50, 55, 60, 65, 70, 75, 80, 85, 90, 91, 92, 93, 94, 95, 96, 97, 98, 99, 99.1, 99.2, 99.3, 99.4, 99.5, 99.6, 99.7, or 99.8% of the inner diameter of the tubular body, and optionally wherein the float has a diameter that is no more than 55, 60, 65, 70, 75, 80, 85, 90, 91, 92, 93, 94, 95, 96, 97, 98, 99, 99.1, 99.2, 99.3, 99.4, 99.5, 99.6, 99.7, 99.8 or 99.9% of the inner diameter of the tubular body.

Statement 4: The system according to any one of Statements 1 to 3, wherein (i) optionally the thixotropic material comprises a polymer selected from: a polyester; a polyolefin; a polyacrylate; and a combination of two or more thereof or (ii) optionally the thixotropic material comprises hydrogenated styrene-butadiene rubber, silica, white oil, antioxidants, or any combination thereof.

Statement 5: The system according to any one of Statements 1 to 4, wherein the float has a hardness of from about 10 to about 60 Shore A, optionally wherein the float has an impervious, non-tacky surface.

Statement 6: The system according to any one of Statements 1 to 5, wherein (i) optionally the float has a specific gravity of from about 1.0 g/mL to about 1.1 g/mL, optionally from about 1.01 g/mL to about 1.09 g/mL, or from about 1.02 g/mL to about 1.08 g/mL, or from about 1.03 g/mL to about 1.07 g/mL, or from about 1.04 g/mL to about 1.06 g/mL, or about 1.05 g/mL, or from about 1.02 to about 1.04 g/mL, or about 1.025 to 1.035 g/mL, or about 1.03 g/mL; or (ii) optionally the float has a density at 25° C. of at least 1.02, 1.03, 1.04, 1.05, 1.06, 1.07 or 1.08 g/cm$^3$; a density at 25° C. that is no more than 1.03, 1.04, 1.05, 1.06, 1.07, 1.08 or 1.09 g/cm$^3$; a density at 25° C. that is less than the density of red blood cells (e.g., from the sample) at 25° C.; a density at 25° C. that is greater than the density of PRP (e.g., from the sample) at 25° C.; a density at 25° C. less than the density at 25° C. of a thixotropic material (e.g., gel) configured to form a barrier with the float; a density at 25° C. equal to the density at 25° C. of a thixotropic material (e.g., gel) configured to form a barrier with the float; or any combination thereof.

Statement 7: The system according to Statement 6, wherein the float has a specific gravity of about 1.03 g/mL.

Statement 8: The system according to any one of Statements 1 to 7, wherein (i) the thixotropic material has a specific gravity of from about 1.0 g/mL to about 1.1 g/mL, optionally from about 1.01 g/mL to about 1.09 g/mL, or from about 1.02 g/mL to about 1.08 g/mL, or from about 1.03 g/mL to about 1.07 g/mL, or from about 1.04 g/mL to about 1.06 g/mL, or about 1.045 g/mL, or about 1.05 g/mL, or about 1.035 to about 1.055 g/cm$^3$; or (ii) optionally the thixotropic material (e.g., gel) has a density at 25° C. of at least 1.02, 1.03, 1.04, 1.05, 1.06, 1.07 or 1.08 g/cm$^3$; a density at 25° C. that is no more than 1.03, 1.04, 1.05, 1.06, 1.07, 1.08 or 1.09 g/cm$^3$; a density at 25° C. that is less than the density of red blood cells (e.g., from the sample) at 25° C.; a density at 25° C. that is greater than the density of PRP (e.g., from the sample) at 25° C.; a density at 25° C. greater than the density at 25° C. of a float configured to form a barrier with the gel; a density at 25° C. equal to the density at 25° C. of a float configured to form a barrier with the thixotropic material (e.g., gel); or any combination thereof.

Statement 9: The system according to any one of Statements 1 to 8, wherein the float has a geometry and surface or either configured to limit platelet adhesion, e.g., wherein a surface of the float and/or the tube, or any portion thereof such as the top surface of the tube is treated/pre-treated (e.g., with a coating, material, polymer, plastic, immobilized liquid (IL) layer, fluoropolymers, polytetrafluoroethylene (PTFE), perfluorocarbons, perfluorodecalin, perfluoroperhydrophenanethrene, almond oil, coconut oil, olive oil, canola oil, silicone oil, perfluoropolyethers, perfluorotripentylamines, tethered-liquid perfluorocarbon (TLP) IL layer, expanded polytetrafluoroethylene (ePTFE), or any combination thereof) to limit platelet adhesion, optionally wherein a surface of the float comprises a material that limits platelet adhesion.

Statement 10: The system according to any one of Statements 1 to 9, wherein the float comprises one or more protuberances 602.

Statement 11: The system according to any one of Statements 1 to 10, wherein the float comprises a plurality of protuberances 602.

Statement 12: The system according to Statement 10 or Statement 11, wherein the protuberances 602 are positioned along the surfaces adjacent to the inner walls of the tubular body.

Statement 13: The system according to any one of Statements 9 to 11, wherein the protuberances 602 are configured to substantially maintain the central axis of the float along the central axis of the tubular body (e.g., the central axis of the float is not more than 30, 25, 20, 15, 10, 9, 8, 7, 6, 5, 4, 3, 2, or 1 degrees from being parallel away from being parallel to the central axis of the tubular body).

Statement 14: The system according to any one of Statements 9 to 12, wherein the protuberances 602 are equidistantly spaced along a surface of the float.

Statement 15: The system according to Statement 14, wherein the protuberances 602 are equidistantly spaced along a surface of the float adjacent to the inner walls of the tubular body.

Statement 16: The system according to any of Statements 10 to 15, wherein the protuberances comprise a different material than the core of the float.

Statement 17: The system according to any one of Statements 1 to 16, wherein the top surface of the float and the bottom surface of the float have substantially similar diameters (e.g., a circle circumscribing the radially outermost portions of the bottom surface of the float has a diameter that is at least 0.6, 0.65, 0.7, 0.75, 0.8, 0.85, 0.90, 0.91, 0.92, 0.93, 0.94, 0.95, 0.96, 0.97, 0.98, or 0.99 times and up to 0.5, 0.6, 07, 0.8, 0.9, 0.91, 0.92, 0.93, 0.94, 0.95, 0.96, 0.97, 0.98, 0.99, or 1 times the diameter of a circle circumscribing the outermost portions at the top surface of the float).

Statement 18: The system according to any one of Statements 1 to 17, wherein the float is substantially cylindrical (e.g., if the float is allowed to sink completely into a test fluid that is less dense than the float, then the volume of the test fluid displaced by the float is at least 0.5, 0.6, 0.7, 0.8, 0.9, 0.91, 0.92, 0.93, 0.94, 0.95, 0.96, 0.97, 0.98 or 0.99 times and up to 1 times the volume of a cylinder that circumscribes the float).

Statement 19: The system according to any one of Statements 1 to 18, wherein the top surface of the float has a greater diameter than the bottom surface of the float.

Statement 20: The system according to any one of Statements 1 to 16, wherein the float is conical.

Statement 21: The system according to any one of Statements 1 to 17 wherein the float is hypocycloid in cross-section.

Statement 22: The system according to any one of Statements 1 to 19, wherein the surface of the float adjacent to the tubular body has a saw-tooth or crenelated pattern.

Statement 23: The system according to any one of Statements 1 to 19, wherein the surface of the float adjacent to the tubular body has a sinusoidal pattern.

Statement 24: The system according to any one of Statements 1 to 16, wherein the float is substantially spherical (e.g., if the float is allowed to sink completely into a test fluid that is less dense than the float, then the volume of the test fluid displaced by the float is at least 0.5, 0.6, 0.7, 0.8, 0.9, 0.91, 0.92, 0.93, 0.94, 0.95, 0.96, 0.97, 0.98 or 0.99 times and up to 1 times the volume of a sphere that circumscribes the float).

Statement 25: The system according to any one of Statements 1 to 23, wherein the float further comprises a cavity (e.g. exterior cavity, for example, in the form of a recess in the outer surface of the float).

Statement 26: The system according to Statement 25, wherein the cavity has a volume greater than about 10%, about 15%, about 20%, about 25%, about 30%, about 35%, about 40%, about 45%, or about 50%, of the total volume of the float and optionally less than 100%, 90%, 80%, 70%, 60%, 50%, 45%, 40%, 35%, 30%, 25%, 20% or 15% of the total volume of the float, the total volume of the float consisting of all points on any imaginary line between any two points on the surface of the float, and optionally the cavity is configured to provide more surface area for the thixotropic material to envelop and thereby promote a better seal.

Statement 27: The system according to Statement 24 or Statement 25, wherein the float profile is tooth-shaped; wherein a plurality of protrusions or extensions (e.g., shaped like claws) extend from the main float body.

Statement 28: The system according to any one of Statements 1 to 27, wherein an inner wall of the tubular body comprises a coating.

Statement 29: The system according to Statement 28, wherein the coating comprises an inert material.

Statement 30: The system according to any one of Statements 1 to 29, wherein the float further comprises a means for signaling the user that the components of the biological sample are adequately separated.

Statement 31: The system according to any one of Statements 1 to 30, wherein the float further comprises a means for signaling the user that the components of the biological sample are adequately separated, after centrifugation.

Statement 32: The system according to Statement 30 or Statement 31, wherein the means for signaling the user that the components of the biological sample are adequately separated comprises a visually perceivable indicator.

Statement 33: The system according to Statement 32, wherein the visually perceivable indicator is selected from a line; a symbol; a color change; an image; and a combination of two or more thereof.

Statement 34: The system according to any one of Statements 1 to 33, wherein the float and the thixotropic material are different in color.

Statement 35: The system according to any one of Statements 1 to 34, wherein the float and thixotropic material are releasably coupled.

Statement 36: The system according to any one of Statements 1 to 35, wherein the volume and rheological profile of the thixotropic gel and the dimensions of the float are configured to permit density separation of the components of the sample by centrifugation.

Statement 37: The system according to any one of Statements 1 to 36, wherein the volume and rheological profile of the thixotropic gel and the dimensions of the float are configured to create a passageway between an outer surface of the float and an inner wall of the tubular body, during centrifugation.

Statement 38: The system according to any one of Statements 1 to 37, wherein the volume and rheological profile of the thixotropic gel and the dimensions of the float are configured to create a substantially impermeable seal between the surface of the float adjacent to the tubular body and an inner wall of the tubular body while the top surface of the float is maintained, in whole or in part, above the thixotropic gel, after centrifugation.

Statement 39: The system according to any one of Statements 1 to 38, wherein the volume and rheological profile of the thixotropic gel and the dimensions of the float are configured to create a substantially impermeable seal between the surface of the float adjacent to the tubular body and an inner wall of the tubular body, after centrifugation.

Statement 40: The system according to any one of Statements 1 to 39, wherein the volume and rheological profile of the thixotropic gel and the dimensions of the float are configured to create an impermeable seal between the surface of the float adjacent to the tubular body and an inner wall of the tubular body while the top surface of the float is maintained, in whole or in part, above the thixotropic gel, after centrifugation.

Statement 41: The system according to any one of Statements 1 to 40, wherein the volume and rheological profile of the thixotropic gel and the dimensions of the float are configured to create an impermeable seal between the surface of the float adjacent to the tubular body and an inner wall of the tubular body, after centrifugation.

Statement 42: The system according to any one of Statements 1 to 41, wherein the thixotropic material has a specific gravity less than the specific gravity of red blood cells and greater than plasma.

Statement 43: The system according to any one of Statements 1 to 42, optionally wherein the thixotropic material and the float have a specific gravity greater than the specific gravity of plasma; and optionally wherein an interior of the tubular body is provided at any vacuum pressure described in this disclosure.

Statement 44: The system according to any one of Statements 1 to 43, further comprising an anticoagulant.

Statement 45: The system according to any one of Statements 1 to 44, further comprising an anticoagulant disposed within the apparatus.

Statement 46: The system according to Statement 43 or Statement 44, wherein the anticoagulant is selected from a citrate salt (e.g. sodium citrate) and ethylenediaminetetraacetic acid (EDTA).

Statement 47: A system for separating components of a liquid biological sample comprising: a tubular body; a float; and a thixotropic material; wherein the volume and rheological profile of the thixotropic material (e.g., gel) and the dimensions of the float are configured to permit density separation of the components of the sample by centrifugation; optionally wherein the thixotropic material is positioned along a bottom inner surface of the tubular body; optionally wherein the thixotropic material is engaged (e.g., adhesively, frictionally, or a combination thereof) with the bottom inner surface of the tubular body; optionally wherein a portion of the float (e.g., bottom portion of the float) is embedded in the thixotropic material; optionally wherein the float and thixotropic material are configured to remain in place within the tubular body during transport (e.g., when the interior of the tubular body is at ambient conditions, at 25° C., at 101.325 kPa, at a vacuum pressure described herein, or any combination thereof); and optionally the thixotropic material is configured so that at 25° C. and 101.325 kPa or a vacuum pressure described herein: (i) the thixotropic material is not flowable, (ii) the thixotropic material engages (e.g., adhesively, frictionally or a combination thereof) with the bottom inner surface of the tubular body (e.g., so that the thixotropic material remains stationary or essentially stationary relative to the bottom inner surface of the tubular body under the force of gravity), (iii) when the float is embedded in the thixotropic material, the float remains stationary or essentially stationary relative to the bottom inner surface of the tubular body under the force of gravity, or (iv) a combination thereof; optionally the float is solid; optionally the float is a single, integral piece; optionally the float is non-porous; optionally the float is configured not to deform under any value, range or combination of ranges of relative centrifugal force described in this disclosure; optionally the float comprises a plurality of mutually spaced protuberances (e.g., ridges); and optionally the protuberances or ridges are longitudinally oriented within 30, 25, 20, 15, 10, 9, 8, 7, 6, 5, 4, 3, 2 or 1 degrees of parallel to a central axis, longitudinal axis, length or any combination thereof of the float).

Statement 48: The system according to Statement 47, wherein the volume and rheological profile of the thixotropic material (e.g., gel) and the dimensions of the float are configured to create a passageway between an outer surface of the float adjacent to the inner wall of the tubular body and an inner wall of the tubular body, during centrifugation.

Statement 49: The system according to Statement 47 or Statement 48, wherein the volume and rheological profile of the thixotropic material (e.g., gel) and the dimensions of the float are configured to create a substantially impermeable barrier between an outer surface of the float adjacent to the inner wall of the tubular body and an inner wall of the tubular body, after centrifugation, optionally while all or substantially all of the top surface of the float remains above the barrier formed by the gel surface (e.g., no more than 10, 9, 8, 7, 6, 5, 4, 3, 2 or 1% of the surface area of the top surface of the float is below the barrier formed by the gel surface when the central axis of the tubular body is oriented vertically.

Statement 50: The system according to any one of Statements 47 to 49, wherein the volume and rheological profile of the thixotropic material (e.g., gel) and the dimensions of the float are configured to create an impermeable barrier between an outer surface of the float adjacent to the inner wall of the tubular body and an inner wall of the tubular body, after centrifugation.

Statement 51: The system according to any one of Statements 1 to 50, wherein the sample comprises blood (e.g., human blood).

Statement 52: A method for preparing platelet rich plasma, comprising: providing a system according to Statement and a blood sample; centrifuging the apparatus for a time and speed sufficient to separate the components of the blood sample into a first phase and a second phase, wherein the first phase comprises red blood cells and the second phase comprises plasma; and removing a portion of the second phase to provide a platelet rich plasma.

Statement 53: The method according to Statement 52, wherein the portion removed from the second phase comprises platelet poor plasma.

Statement 54: The method according to Statement 52 or Statement 53, further comprising resuspending platelets in the platelet rich plasma.

Statement 55: The method according to any one of Statements 52 to 54, wherein the float-gel-inner wall assembly (e.g., forming the substantially impermeable barrier) is maintained at equilibrium between the first phase and the second phase.

Statement 56: A method for separating a biological sample, comprising: introducing a biological sample into an apparatus comprising: a tubular body; a float; a thixotropic material (e.g., gel); and optionally an anticoagulant; subjecting the apparatus to centrifugation for a time and speed sufficient to separate the components of the biological sample into a plurality of phases.

Statement 57: The method according to Statement 56, wherein the plurality of phases comprises a first phase comprising red blood cells and a second phase comprising plasma.

Statement 58: The method according to Statement 56 or Statement 57, wherein the float and thixotropic material form a substantially impermeable barrier between an outer surface of the float and an inner wall of the tubular body, optionally while the top surface of the float remains substantially or completely above the barrier formed (e.g., no more than 10, 9, 8, 7, 6, 5, 4, 3, 2 or 1% of the surface area of the top surface of the float is below the barrier formed when the central axis of the tubular body is oriented vertically); optionally wherein the float and thixotropic material are above the first phase, after centrifugation.

Statement 59: A method for treating, preventing or ameliorating a symptom associated with: acne; alopecia; pain; periodontal disease; periodontal defects; chronic wounds; diabetic foot ulcer; traumatic injury; scars; incontinence; and/or wrinkles, comprising administering a product produced by the method according to any one of Statements 52 to 58 to a mammalian subject in need thereof.

Statement 60: A method for increasing, enhancing or promoting: hair growth; tissue healing; tissue regeneration; sexual wellness; bone growth; bone regeneration; and/or periodontal regeneration; comprising administering a product produced by the method according to any one of Statements 52 to 59 to a mammalian subject in need thereof.

Statement 61: A composition comprising a product produced by the method according to any one of claims 51 to 56; and a carrier.

Statement 62: The composition according to Statement 61, wherein the carrier is selected from a pharmaceutically acceptable carrier and a cosmetically acceptable carrier.

Statement 63: The embodiment, system, method or composition of any preceding Statement, optionally wherein substantially impermeable means configured to prevent the mixing of a first phase and a second phase of the sample on opposite surfaces of the substantially impermeable barrier (i) at least when a tubular body, of a set of components comprising (or consisting of) the tubular body, the thixotropic material (e.g., gel), float, first phase and second phase, is stationary and (ii) optionally after the tubular body (containing the thixotropic gel, float, first phase, and second phase) is oscillated about a starting point along a vertical axis at an amplitude of three inches above the starting point and three inches below the starting point at a rate of 4 complete oscillations per second for 10, 20, 30, 40, 50, 60, 70, 80, 90, 100, 110 or 120 seconds, optionally wherein substantially impermeable means configured so that no more than 3, 2, 1, 0.5, 0.4, 0.3, 0.2 or 0.1 wt. % of material from the first phase is permitted to pass the barrier to the second phase and no more than 3, 2, 1, 0.5, 0.4, 0.3, 0.2 or 0.1 wt. % of material from the second phase is permitted to pass the barrier to the first phase, and optionally substantially impermeable means configured to prevent the mixing of a first phase and a second phase of the sample (e.g., liquid biological sample, for example, a blood sample) on opposite surfaces of the substantially impermeable seal at least under a set of conditions that one having ordinary skill in the art would recognize as ordinarily causing a gel only barrier to breach (e.g., after vigorous shaking, for example, as one would shake a spray paint can for two minutes).

EXAMPLES

Example 1

Validation experiments were conducted to evaluate systems comprising floats of different densities and shapes and different volumes of a thixotropic material.

TABLE 1

| Sample | Float Density (g/mL) | Float Design | Gel Density (g/mL) | Gel Volume (mL) | RPM | Platelet Count | Observations |
|---|---|---|---|---|---|---|---|
| Whole Blood | n/a | n/a | n/a | n/a | n/a | 186 | n/a |
| Comp. Ex. I | 1.08 | Bullet | 1.05 | 1.25 | 2000 | n/a | Float did not rise. Leaked when inverted. Additional spins at 2000 and 3500 RPM did not improve outcome. |
| Comp. Ex. II | 1.08 | Bullet | 1.05 | 1.25 | 3500 | n/a | Tube broke. |
| Comp. Ex. III | 1.08 | Bullet | 1.05 | 1.25 | 2000 | n/a | Float moved slightly, but not to a meaningful extent. Additional spin at 2500 RPM did not result in separation. |
| Ex. I | 1.03 | Bullet | 1.05 | 2.5 | 3500 | 333 | Looks great. Gel on bottom and half-way up sides of float. Withstood agitation. Minimal blush. |
| Ex. II | 1.03 | Bullet | 1.05 | 2.5 | 3500 | 496 | Looks great. Gel observed on bottom and most of the way up the float. Withstood agitation. No blush. |

As illustrated by the data described in Table 1 (above), the densities of both the float and gel, and the volumes of each are critical to properly separating the components of the sample and creating a barrier. Specifically, the amount and densities of the gel and float must be precisely tailored to avoid breach and achieve plasma results. The data described in Table 1 (above) demonstrates that systems of the present disclosure demonstrate platelet capture with minimal contamination of the plasma by the higher density components in the sample.

Example 2

Based on the results described in Example 1 (above), additional experiments were conducted with four (4) systems of the present disclosure, which included: two float designs (bullet [see, e.g. FIG. 6] and claw [see, e.g. FIGS. 2 and 7A-7D]) and two gel volumes (2 mL and 3 mL). The results of these experiments are described below in Table 2.

TABLE 2

| Sample | Float Density (g/mL) | Float Design | Gel Density (g/mL) | Gel Volume (mL) | RPM | Platelet Count | Observations |
|---|---|---|---|---|---|---|---|
| Whole Blood | n/a | n/a | n/a | n/a | n/a | 308 | n/a |
| Ex. III | 1.04 | Bullet | 1.05 | 2 | 3500 | 581 | Clear separation of PRP from RBC and WBC. No leakage of RBC despite vigorous shaking. |
| Ex. IV | 1.04 | Claw | 1.05 | 3 | 3500 | 504 | Clear separation of PRP from RBC and WBC. No leakage of RBC despite vigorous shaking. |
| Ex. V | 1.03 | Bullet | 1.05 | 2 | 3500 | 546 | Clear separation of PRP from RBC and WBC. No leakage of RBC despite vigorous shaking. |
| Ex. VI | 1.03 | Claw | 1.05 | 3 | 3500 | 558 | Clear separation of PRP from RBC and WBC. No leakage of RBC despite vigorous shaking. |

As illustrated by the data described in Table 2 (above), all four (4) systems of the present disclosure performed very well. Specifically, there was a clear separation of platelet rich plasma (PRP) from the red blood cells (RBC) and white blood cells (WBC). Platelet counts were well above whole blood in all four experiments. The top surface of the float remained, in whole or significant part, above the barrier formed by the float and gel. The tubes were subjected to vigorous shaking and there was no perceivable leakage of RBC into the PRP volume. As noted previously, this is significant, because in gel-only separation systems, breach can occur with minimal shaking causing leakage of RBC, resulting in a pink or even a red PRP admixture. This is also significant because platelets which might adhere to the limited amount of gel can be successfully dislodged with agitation.

Example 3

In addition to the experiments described in Tables 1 and 2, one "bullet" float and one "claw" float were placed into tubes having a slightly larger diameter than the tubes used in Examples 1 and 2. As illustrated by the results described in Table 3 (below), the fit between the float outer diameter and the tube inner diameter need not be very precise; and more importantly, this data demonstrates that some systems of the present disclosure are able to successfully separate components of a sample despite variations in the inner diameter of the tube, and the float deployed within the tube.

TABLE 3

| Sample | Float Density (g/mL) | Float Design | Gel Density (g/mL) | Gel Quantity (mL) | RPM | Platelet Count | Observations |
| --- | --- | --- | --- | --- | --- | --- | --- |
| Whole Blood | n/a | n/a | n/a | n/a | n/a | 308 | n/a |
| Ex. VII | 1.02 | Bullet | 1.05 | 2 | 3500 | 532 | Clear separation of PRP from RBC and WBC. No leakage of RBC despite vigorous shaking. |
| Ex. VIII | 1.02 | Claw | 1.05 | 3 | 3500 | 563 | Clear separation of PRP from RBC and WBC. No leakage of RBC despite vigorous shaking. |

Additional Embodiments

The following clauses provide additional description of embodiments of the systems, methods, and compositions of this disclosure.

1. A system for separating components of a sample (optionally the system configured to separate the components of the sample (e.g., a liquid biological sample), configured to separate the components of the sample during centrifugation, or any combination thereof), comprising:
   an apparatus comprising:
      a tubular body for receiving sample (e.g. a liquid biological sample);
      a thixotropic material; and
      a float comprising:
         a core;
         a top surface; and
         a bottom surface;
   optionally wherein the float has a specific gravity less than or equal to the specific gravity of the thixotropic material, optionally wherein the system comprises the sample, wherein the specific gravity of the thixotropic material is or is configured to be equal to or less than the specific gravity of the component or separated phase of the sample with the greatest specific gravity, or any combination thereof;
   optionally wherein the thixotropic material is positioned along a bottom inner surface of the tubular body;
   optionally wherein the thixotropic material is engaged (e.g., adhesively, frictionally, or a combination thereof) with the bottom inner surface of the tubular body;
   optionally wherein a portion of the float (e.g., bottom portion of the float) is embedded in the thixotropic material;
   optionally wherein the float and thixotropic material are configured to remain in place within the tubular body during transport (e.g., at 25° C. and 101.325 kPa); and
   optionally the thixotropic material is configured so that at 25° C. and 101.325 kPa: (i) the thixotropic material is not flowable, (ii) the thixotropic material engages (e.g., adhesively, frictionally or a combination thereof) with the bottom inner surface of the tubular body (e.g., so that the thixotropic material remains stationary or essentially stationary relative to the bottom inner surface of the tubular body under the force of gravity), (iii) when the float is embedded in the thixotropic material, the float remains stationary or essentially stationary relative to the bottom inner surface of the tubular body under the force of gravity, or (iv) a combination thereof; optionally the float is solid (e.g., solid phase as opposed to being a liquid or gas, in the sense of being filled and not hollow, or any combination thereof); optionally the float is made with a hollow construction provided by an inner void and optionally the float has no aperture or port to connect the inner void to the exterior of the float; optionally the float is a single, integral piece; optionally the float is non-porous; optionally the float is configured not to deform under any value, range or combination of ranges of relative centrifugal force described in this disclosure; optionally the float comprises a plurality of mutually spaced protuberances (e.g., ridges); and optionally the protuberances or ridges are longitudinally oriented within 30, 25, 20, 15, 10, 9, 8, 7, 6, 5, 4, 3, 2 or 1 degrees of parallel to a central axis, longitudinal axis, length or combination thereof of the float);

optionally the system is configured to separate the components of the sample by centrifugation of the apparatus while the tubular body contains the liquid biological sample, the thixotropic material, and the float; and optionally the tubular body, in combination with a stopper, is configured so that the interior of the tubular body is at an absolute pressure that is a vacuum pressure (for example, such that the vacuum can be used to facilitate drawing a sample that is blood); between 0 and 1 atm; no more than 0.9, 0.8, 0.7, 0.6, 0.5, 0.4, 0.2, 0.1, 0.05, 0.04, 0.03, 0.02, 0.01, 0.005, 0.001, $1\times10^{-4}$, $1\times10^{-5}$, $1\times10^{-6}$, $1\times10^{-7}$, $1\times10^{-8}$, $1\times10^{-9}$, $1\times10^{-10}$, $1\times10^{-11}$, $1\times10^{-12}$, $1\times10^{-13}$, $1\times10^{-14}$, $1\times10^{-15}$ atm; at least 0.9, 0.8, 0.7, 0.6, 0.5, 0.4, 0.2, 0.1, 0.05, 0.04, 0.03, 0.02, 0.01, 0.005, 0.001, $1\times10^{-4}$, $1\times10^{-5}$, $1\times10^{-6}$, $1\times10^{-7}$, $1\times10^{-8}$, $1\times10^{-9}$, $1\times10^{-10}$, $1\times10^{-11}$, $1\times10^{-12}$, $1\times10^{-13}$, $1\times10^{-14}$, $1\times10^{-15}$ atm; or any combination thereof.

2. The system according to clause 1, optionally the float is made of, comprises, consists essentially of or consists of a polymer, a plurality of polymers, acrylonitrile butadiene styrene (ABS), polycarbonate, plastic, rubber, metal, a plurality of metals, metal alloys, or any combination thereof;

optionally wherein the float has a specific gravity less than the specific gravity of the thixotropic material, a specific gravity larger than the specific gravity of the component of the sample with the smallest specific gravity, or any combination thereof optionally wherein the thixotropic material has a specific gravity smaller than the specific gravity of the component of the sample with the largest specific gravity.

3. The system according to clause 1 or clause 2, optionally wherein the float has a circular cross-section, optionally wherein the float (e.g., the circular cross-section of the float) has a diameter, including any protuberances, that is less than or equal to the inner diameter of the tubular body, optionally wherein the float has a diameter, including any protuberances, that is at least 50, 55, 60, 65, 70, 75, 80, 85, 90, 91, 92, 93, 94, 95, 96, 97, 98, 99, 99.1, 99.2, 99.3, 99.4, 99.5, 99.6, 99.7, or 99.8% of the inner diameter of the tubular body, optionally wherein the float has a diameter, including any protuberances, that is no more than 55, 60, 65, 70, 75, 80, 85, 90, 91, 92, 93, 94, 95, 96, 97, 98, 99, 99.1, 99.2, 99.3, 99.4, 99.5, 99.6, 99.7, 99.8 or 99.9% of the inner diameter of the tubular body, wherein the float has a diameter, excluding any protuberances, that is less than or equal to the inner diameter of the tubular body, optionally wherein the float has a diameter, excluding any protuberances, that is at least 50, 55, 60, 65, 70, 75, 80, 85, 90, 91, 92, 93, 94, 95, 96, 97, 98, 99, 99.1, 99.2, 99.3, 99.4, 99.5, 99.6, 99.7, or 99.8% of the inner diameter of the tubular body, optionally wherein the float has a diameter, excluding any protuberances, that is no more than 55, 60, 65, 70, 75, 80, 85, 90, 91, 92, 93, 94, 95, 96, 97, 98, 99, 99.1, 99.2, 99.3, 99.4, 99.5, 99.6, 99.7, 99.8 or 99.9% of the inner diameter of the tubular body, optionally wherein the inner diameter of the tubular body is at least 5, 10, 15, 20, 25, 30, 35, 40, 45, or 50 mm, optionally wherein the inner diameter of the tubular body is no more than 5, 10, 15, 20, 25, 30, 35, 40, 45, or 50 mm, or any combination thereof.

4. The system according to any foregoing clause, wherein the thixotropic material comprises a polymer selected from: a polyester; a polyolefin; a polyacrylate; hydrogenated butadiene rubber, silica, white oil and antioxidants; and a combination of two or more thereof.

5. The system according to any foregoing clause, wherein the float has a shore hardness of from about 1 to about 50, optionally about 5 to about 45, optionally about 10 to about 35, optionally about 15 to about 30, optionally about 20 to about 25, preferably about 30.

6. The system according to any foregoing clause, wherein the float has a specific gravity of at least about 1.0, 1.01, 1.02, 1.03, 1.04, 1.05, 1.06, 1.07, 1.08, 1.09, or 1.1 g/mL, no more than about 1.0, 1.01, 1.02, 1.03, 1.04, 1.05, 1.06, 1.07, 1.08, 1.09, or 1.1 g/mL, or any combination thereof, optionally from about 1.02 to 1.09 g/mL, optionally from about 1.0 g/mL to about 1.1 g/mL, optionally from about 1.01 g/mL to about 1.09 g/mL, or from about 1.02 g/mL to about 1.08 g/mL, or from about 1.03 g/mL to about 1.07 g/mL, or from about 1.04 g/mL to about 1.06 g/mL, or about 1.05 g/mL, about 1.02 to about 1.04 g/mL, or about 1.025 to 1.035 g/mL.

7. The system according to any foregoing clause, wherein the float has a specific gravity of about 1.03 g/mL.

8. The system according to any foregoing clause, wherein the thixotropic material has a specific gravity of at least about 1.0, 1.01, 1.02, 1.03, 1.04, 1.05, 1.06, 1.07, 1.08, 1.09, or 1.1 g/cm$^3$, no more than about 1.0, 1.01, 1.02, 1.03, 1.04, 1.05, 1.06, 1.07, 1.08, 1.09, or 1.1 g/cm$^3$, or any combination thereof, optionally from about 1.02 to 1.09 g/cm$^3$, optionally from about 1.0 g/mL to about 1.1 g/mL, optionally from about 1.01 g/mL to about 1.09 g/mL, or from about 1.02 g/mL to about 1.08 g/mL, or from about 1.03 g/mL to about 1.07 g/mL, or from about 1.04 g/mL to about 1.06 g/mL, or about 1.045 g/mL, or about 1.05 g/mL or about 1.035 to about 1.055 g/cm$^3$.

9. The system according to any foregoing clause, optionally wherein the float has a surface configured to limit platelet adhesion, e.g., wherein a surface of the float and/or tubular body, or any portion thereof (e.g., the top surface of the tubular body) is treated/pre-treated (e.g., with a coating, material, polymer, plastic, immobilized liquid (IL) layer, fluoropolymers, polytetrafluoroethylene (PTFE), perfluorocarbons, perfluorodecalin, perfluoroperhydrophenanethrene, almond oil, coconut oil, olive oil, canola oil, silicone oil, perfluoropolyethers, perfluorotripentylamines, tethered-liquid perfluorocarbon (TLP) IL layer, expanded polytetrafluoroethylene (ePTFE), or any combination thereof) to limit platelet adhesion, optionally wherein a surface of the float comprises a material that limits platelet adhesion, and optionally wherein the float has a geometry (e.g. conical shape in which the bottom is larger than the top), cylindrical shape, dome shape, bell-like shape, spherical shape or rounded shape above a point on the float corresponding to a height on the float where no gel is intended to be located above the height when a barrier has been formed (e.g., the barrier comprising the float, the gel and the inner surface of the tubular body) after centrifugation.

10. The system according to any foregoing clause, wherein the float comprises one or more protuberances.

11. The system according to any foregoing clause, wherein the float comprises a plurality of protuberances.

12. The system according to clause 10 or clause 11, wherein the protuberances are positioned along a surface, a plurality of the surfaces or any of the surfaces configured to be adjacent to an inner wall or the inner walls of the tubular body (e.g., configured to be adjacent to the inner wall or the inner walls before centrifugation, after centrifugation is completed, or any combination thereof.

13. The system according to any one of clauses 10 to 12, wherein the protuberances are configured to substantially maintain the central axis of the float along the central axis of the tubular body.

14. The system according to any one of clauses 10 to 13, wherein the protuberances are equidistantly spaced, laterally, or longitudinally or both, along a surface of the float.

15. The system according to clause 14, wherein the protuberances are equidistantly spaced along a surface of the float adjacent to the inner walls of the tubular body.

16. The system according to any of clauses 10 to 15, wherein the protuberances comprise a different material than the core of the float.

17. The system according to any foregoing clause, wherein the top surface of the float and the bottom surface of the float have substantially similar diameters (e.g., a circle circumscribing the radially outermost portions of the bottom surface of the float has a diameter that is at least 0.2, 0.25, 0.30, 0.35, 0.40, 05.0, 0.55, 0.6, 0.65, 0.7, 0.75, 0.8, 0.85, 0.90, 0.91, 0.92, 0.93, 0.94, 0.95, 0.96, 0.97, 0.98, or 0.99 times and up to 0.5, 0.6, 07, 0.8, 0.9, 0.91, 0.92, 0.93, 0.94, 0.95, 0.96, 0.97, 0.98, 0.99, or 1 times the diameter of a circle circumscribing the outermost portions at the top surface of the float).

18. The system according to any foregoing clause, wherein the float is substantially cylindrical (e.g., if the float is allowed to sink completely into a test fluid that is less dense than the float, then the volume of the test fluid displaced by the float is at least 0.5, 0.6, 0.7, 0.8, 0.9, 0.91, 0.92, 0.93, 0.94, 0.95, 0.96, 0.97, 0.98 or 0.99 times and up to 1 times the volume of a cylinder that circumscribes the float).

19. The system according to any foregoing clause, wherein the top surface of the float has a greater diameter than the bottom surface of the float.

20. The system according to any one of clauses 1 to 17, wherein the float or portion thereof (e.g., lower portion or the bottom) is conical, claw-shaped, bullet-shaped, or any combination thereof.

21. The system according to any one of clauses 1 to 17 wherein the float is hypocycloid along the axis of the tube.

22. The system according to any foregoing clause, wherein the surface of the float adjacent to the tubular body has a saw-tooth or crenelated pattern (e.g., an outer surface with a saw-tooth or crenelated pattern or an outer surface with a saw-tooth or crenelated edge).

23. The system according to any one of clauses 1 to 18, wherein the surface of the float adjacent to the tubular body has a sinusoidal pattern.

24. The system according to any one of clauses 1 to 16, wherein the float is substantially spherical.

25. The system according to any one of clauses 1 to 23, wherein the float further comprises a cavity.

26. The system according to clause 25, wherein the cavity has a volume greater than 50% of the total volume of the float.

27. The system according to any preceding clause, wherein the float or a portion of the float comprises protrusions, comprises protuberances, comprises extensions, is at least partially tooth-shaped (e.g., the float comprises protrusions, protuberances or extensions (which can be claw-shaped) at the bottom of the float), or any combination thereof, optionally wherein the protrusions, protuberances, extensions, tooth-like shape of a portion of the float, or any combination thereof are configured to provide additional surface area for contact, engagement, adherence, or any combination thereof between the float and the thixotropic material, optionally the additional surface area for contact and engagement between the float and the thixotropic material can be provided at a location where the float is intended or configured to contact the thixotropic material before centrifugation begins, at a location where the float is intended to contact the thixotropic material after centrifugation to form a barrier comprising the float and the thixotropic material, or any combination thereof.

28. The system according to any foregoing clause, wherein an inner wall of the tubular body comprises a coating.

29. The system according to clause 28, wherein the coating comprises an inert material.

30. The system according to any foregoing clause, wherein the float further comprises a means for signaling the user that the components of the biological sample are adequately separated.

31. The system according to any foregoing clause, wherein the float further comprises a means for signaling the user that the components of the biological sample are adequately separated, after centrifugation.

32. The system according to clause 30 or clause 31, wherein the means for signaling the user that the components of the biological sample are adequately separated comprises a visually perceivable indicator.

33. The system according to clause 32, wherein the visually perceivable indicator is selected from a line; a symbol; a color change; an image; and a combination of two or more thereof.

34. The system according to any foregoing clause, wherein the float and the thixotropic material are different in color.

35. The system according to any foregoing clause, wherein the float and thixotropic material are releasably coupled.

36. The system according to any foregoing clause, wherein the volume and rheological profile of the thixotropic gel and the dimensions of the float are configured to permit density separation of the components of the sample by centrifugation.

37. The system according to any foregoing clause, wherein the volume and rheological profile of the thixotropic gel and the dimensions of the float are configured to create a passageway between an outer surface of the float and an inner wall of the tubular body, during centrifugation.

38. The system according to any foregoing clause, wherein the volume and rheological profile of the thixotropic gel and the dimensions of the float are configured to create a substantially impermeable seal between the surface of the float adjacent to the tubular body and an inner wall of the tubular body.

39. The system according to any foregoing clause, wherein the volume and rheological profile of the thixotropic gel and the dimensions of the float are configured to create a substantially impermeable seal between the surface of the float adjacent to the tubular body and an inner wall of the tubular body; optionally wherein the float and thixotropic material are above the first phase, after centrifugation.

40. The system according to any foregoing clause, wherein the volume and rheological profile of the thixotropic gel and the dimensions of the float are configured to create an impermeable seal between the surface of the float adjacent to the tubular body and an inner wall of the tubular body; optionally wherein the float and thixotropic material are above the first phase, after centrifugation.

41. The system according to any foregoing clause, wherein the volume and rheological profile of the thixotropic gel and the dimensions of the float are configured to create an impermeable seal between the surface of the float adjacent to the tubular body and an inner wall of the tubular body, after centrifugation.
42. The system according to any foregoing clause, wherein the thixotropic material has a specific gravity less than the specific gravity of red blood cells.
43. The system according to any foregoing clause, wherein the thixotropic material and the float have a specific gravity greater than the specific gravity of plasma.
44. The system according to any foregoing clause, further comprising an anticoagulant.
45. The system according to any foregoing clause, further comprising an anticoagulant disposed within the apparatus.
46. The system according to clause 44 or clause 45, wherein the anticoagulant is selected from a citrate salt (e.g. sodium citrate) and ethylenediaminetetraacetic acid (EDTA).
47. The system according to any foregoing clause, wherein the thixotropic material and float remain in a substantially fixed position (e.g., relative to the tubular body) during transport, optionally wherein remaining in the substantially fixed position means that no point on the float and no boundary of the thixotropic material moves along a central axis or length of the tubular body by more than 15, 10, 9, 8, 7, 6, 5, 4, 3, 2 or 1% of the length of the float along the longitudinal axis or the central axis of the float or the two points on the outer surface of the float that are the furthest apart).
48. A system for separating components of a sample comprising:
   a tubular body;
   a float; and
   a thixotropic material;
      wherein the volume and rheological profile of the thixotropic material and the dimensions of the float are configured to permit density separation of the components of the sample by centrifugation.
49. The system according to clause 48, wherein the volume and rheological profile of the thixotropic material and the dimensions of the float are configured to create a passageway between an outer surface of the float adjacent to the inner wall of the tubular body and an inner wall of the tubular body, during centrifugation.
50. The system according to clause 48 or clause 49, wherein the volume and rheological profile of the thixotropic material and the dimensions of the float are configured to create a substantially impermeable barrier between an outer surface of the float adjacent to the inner wall of the tubular body and an inner wall of the tubular body, after centrifugation, optionally wherein substantially impermeable means configured to prevent the mixing of a first phase and a second phase of the sample on opposite surfaces of the substantially impermeable barrier at least when a set of components comprising the tubular body, the thixotropic material, float, first phase and second phase are stationary.
51. The system according to any one of clauses 48 to 50, wherein the volume and rheological profile of the thixotropic material and the dimensions of the float are configured to create an impermeable barrier between an outer surface of the float adjacent to the inner wall of the tubular body and an inner wall of the tubular body, after centrifugation.
52. The system according to any foregoing clause, wherein the sample comprises blood (e.g., human blood).
53. The system according to any foregoing clause, wherein at least a portion of the top surface of the float is situated above the thixotropic material, after centrifugation.
54. The system according to any foregoing clause, wherein the top surface of the float is situated above the thixotropic material, after centrifugation.
55. A method for preparing platelet rich plasma, comprising:
   providing a system according to any foregoing clause and a blood sample;
   centrifuging the apparatus for a time and speed sufficient to separate the components of the blood sample into a first phase and a second phase, wherein the first phase comprises red blood cells and the second phase comprises plasma; and
   removing a portion of the second phase (e.g., from a tubular body of the apparatus) to provide a platelet rich plasma (e.g., in the tubular body).
56. The method according to clause 55, wherein the portion removed from the second phase comprises platelet poor plasma.
57. The method according to clause 55 or clause 56, further comprising resuspending platelets in the platelet rich plasma, agitating the platelet rich plasma, or a combination thereof.
58. The method according to any one of clauses 55 to 57, wherein the float and thixotropic material are maintained at equilibrium between the first phase and the second phase.
59. A method for separating components in a sample, comprising:
   introducing a sample into an apparatus (e.g., the apparatus of any preceding clause or any apparatus or any system comprising an apparatus disclosed in this application) comprising:
      a tubular body;
      a float;
      a thixotropic material; and
      optionally an anticoagulant; and
   subjecting the apparatus to centrifugation for a time and speed sufficient to separate the components of the sample into a plurality of phases.
60. The method according to clause 59, wherein the plurality of phases comprises a first phase comprising red blood cells and a second phase comprising plasma.
61. The method according to clause 59 or clause 60, wherein the float and thixotropic material form a substantially impermeable barrier between an outer surface of the float and an inner wall of the tubular body, after centrifugation, optionally wherein substantially impermeable means configured to prevent the mixing of a first phase and a second phase of the sample on opposite surfaces of the substantially impermeable barrier at least when the tubular body is stationary.
62. The method according to any one of clauses 59 to 61, wherein after centrifugation, at least a portion of the top surface of the float is situated above the thixotropic material.
63. The method according to any one of clauses 59 to 62, wherein after centrifugation, the top surface of the float is situated above the thixotropic material.
64. A method for treating, preventing, or ameliorating a symptom associated with:
   acne;
   alopecia;
   pain;
   periodontal disease;
   periodontal defects;
   chronic wounds;
   diabetic foot ulcer;
   traumatic injury;

scars;
incontinence; and/or
wrinkles,
comprising administering a product produced by the method according to any one of clauses 55 to 63, to a mammalian subject in need thereof.

65. A method for increasing, enhancing, or promoting:
hair growth;
tissue healing;
tissue regeneration;
sexual wellness;
bone growth;
bone regeneration; and/or
periodontal regeneration;
comprising administering a product produced by the method according to any one of clauses 55 to 63 to a mammalian subject in need thereof.

66. The method of any preceding method clause, wherein the step of removing a portion of the second phase to provide a platelet rich plasma comprises:
removing platelet poor plasma from the second phase (e.g., from a top portion of the second phase or plasma), thereby leaving behind a remaining portion of the second phase (e.g., a bottom portion of the second phase or plasma);
agitating the remaining portion of the second phase (e.g., to suspend platelets in the second phase) to provide an agitated remaining portion; and
removing the agitated remaining portion from the apparatus, thereby providing the platelet rich plasma;
optionally the step of removing the platelet poor plasma comprises removing at least 25, 30, 35, 40, 45, 50, 55, 60, 65, 70, 75, 80, 85 or 90% by volume of the second phase or plasma; no more than 25, 30, 35, 40, 45, 50, 55, 60, 65, 70, 75, 80, 85 or 90% by volume of the second phase or plasma; or any combination thereof;
optionally the step of agitating the remaining portion of the second phase comprises (i) agitation in accordance with instructions for use of the apparatus, (ii) manually shaking the remaining portion of the second phase, (iii) oscillating the remaining portion of the second phase about a starting point along a vertical axis at an amplitude of at least 1, 2, or 3 inches above the starting point (and optionally no more than 1, 2 or 3 inches above the starting point) and at least 1, 2, or 3 inches below the starting point (and optionally no more than 1, 2, or 3 inches below the starting point) at a rate of at least 1, 2, 3, or 4 complete oscillations per second (and optionally no more than 1, 2, 3, or 4 complete oscillations per second), for at least 10, 20, 30, 40, 50, 60, 70, 80, 90, 100, 110 or 120 seconds, (and optionally no more than 10, 20, 30, 40, 50, 60, 70, 80, 90, 100, 110 or 120 second), (iv) agitating in accordance with any embodiment in this disclosure, (v) agitating the remaining portion of the second phase while the remaining portion of the second phase is in the tubular body and optionally while a stopper is coupled to the tubular body to contain the remaining portion of the second phase, or (vi) any combination thereof.

67. The method of any preceding method clause,
optionally wherein before the step of removing a portion of the second phase to provide a platelet rich plasma, the second phase is agitated;
optionally wherein the step of removing a portion of the second phase to provide a platelet rich plasma comprises removing essentially all of the second phase or plasma to provide the platelet rich plasma, removing at least 25, 30, 35, 40, 45, 50, 55, 60, 65, 70, 75, 80, 85, 90, 91, 92, 93, 94, 95, 96, 97, 98, 99, or 100% by volume of the second phase or plasma, removing no more than 25, 30, 35, 40, 45, 50, 55, 60, 65, 70, 75, 80, 85, 90, 91, 92, 93, 94, 95, 96, 97, 98, 99, or 100% by volume of the second phase or plasma, or any combination thereof;
optionally wherein agitating the second phase suspends the platelets in the second phase to provide an agitated second phase; and
optionally removing the agitated second phase from the apparatus, thereby providing the platelet rich plasma; and
optionally the step of agitating the second phase comprises (i) agitation in accordance with instructions for use of the apparatus, (ii) manually shaking the second phase, (iii) oscillating the second phase about a starting point along a vertical axis at an amplitude of at least 1, 2, or 3 inches above the starting point (and optionally no more than 1, 2 or 3 inches above the starting point) and at least 1, 2, or 3 inches below the starting point (and optionally no more than 1, 2, or 3 inches below the starting point) at a rate of at least 1, 2, 3, or 4 complete oscillations per second (and optionally no more than 1, 2, 3, or 4 complete oscillations per second), for at least 10, 20, 30, 40, 50, 60, 70, 80, 90, 100, 110 or 120 seconds, (and optionally no more than 10, 20, 30, 40, 50, 60, 70, 80, 90, 100, 110 or 120 second), (iv) agitating in accordance with any embodiment in this disclosure, (v) agitating the second phase while the second phase is in the tubular body and optionally while a stopper is coupled to the tubular body to contain the second phase, or (vi) any combination thereof.

68. The method of any preceding method clause:
optionally wherein the centrifugation of the tubular body results in the application of a relative centrifugal force (RCF) on the tubular body that is at least 500, 750, 1000, 1250, 1300, 1350, 1400, 1450, 1500, 1550, 1600, 1650, 1700, 1750, 2000, 3000, 4000 or 5000 g; no more than 500, 750, 1000, 1250, 1300, 1350, 1400, 1450, 1500, 1550, 1600, 1650, 1700, 1750, 2000, 3000, 4000 or 5000 g; or any combination thereof;
optionally wherein the RCF is applied to the tubular body for at least 4, 5, 6, 7, 8, 9, 10, 11, 12, 13, 14, or 15 minutes; no more than 5, 6, 7, 8, 9, 10, 11, 12, 13, 14, 15 or 30 minutes; or any combination thereof.

69. A composition comprising a product produced by the method according to any one of clause 55 to 68; and a carrier.

70. The composition according to clause 69, wherein the carrier is selected from a pharmaceutically acceptable carrier and a cosmetically acceptable carrier.

71. The embodiment, system, method or composition of any preceding clause, optionally wherein a first volume is selected from the volume of (a) the second component, (b) the first phase, (c) the phase below the barrier, (d) the component below the barrier, (e) blood cells (e.g. below the barrier), or (f) any combination thereof;
optionally wherein a second volume is selected from the volume of (a) the first component, (b) the second phase, (c) the phase above the barrier, (d) the component above the barrier, (e) plasma, platelets, or any combination thereof (e.g., above the barrier), or (f) any combination thereof;
optionally wherein a third volume is selected from (a) the total volume of the first component and the second component, (b) the total volume of the first phase and the second phase, (c) the total volume of all phases from the sample, (d) the total volume of all components of the sample, (e) the total volume of plasma, platelets and blood cells in the sample, or (f) any combination thereof;

optionally wherein, after centrifugation, the first volume makes up or the system is configured so that the first volume makes up (I) at least 45, 46, 47, 48, 49, 50, 51, 52, 53, 54, 55, 56, 57, 58, 59, 60, 61, 62, 63, 64 or 65% by volume, (II) no more than 45, 46, 47, 48, 49, 50, 51, 52, 53, 54, 55, 56, 57, 58, 59, 60, 61, 62, 63, 64 or 65% by volume, or (III) any combination thereof of the third volume;

optionally wherein, after centrifugation, the second volume makes up or the system is configured so that the second volume makes up (I) at least 35, 36, 37, 38, 39, 40, 41, 42, 43, 44, 45, 46, 47, 48, 49, 50, 51, 52, 53, 54, or 55% by volume, (II) no more than 35, 36, 37, 38, 39, 40, 41, 42, 43, 44, 45, 46, 47, 48, 49, 50, 51, 52, 53, 54, or 55% by volume, or (III) any combination thereof of the third volume;

optionally wherein substantially impermeable means configured to prevent the mixing of a first phase and a second phase of the sample on opposite surfaces of the substantially impermeable barrier (i) at least when a tubular body, of a set of components comprising (or consisting of) the tubular body, the thixotropic material (e.g., gel), float, first phase and second phase, is stationary and (ii) optionally after the tubular body (containing the thixotropic gel, float, first phase, and second phase) is oscillated about a starting point along a vertical axis at an amplitude of three inches above the starting point and three inches below the starting point at a rate of 1, 2, 3 or 4 complete oscillation per second for 10, 20, 30, 40, 50, 60, 70, 80, 90, 100, 110 or 120 seconds, optionally wherein substantially impermeable means configured so that no more than 3, 2, 1, 0.5, 0.4, 0.3, 0.2 or 0.1 wt. % of material from the first phase is permitted to pass the barrier to the second phase and no more than 3, 2, 1, 0.5, 0.4, 0.3, 0.2 or 0.1 wt. % of material from the second phase is permitted to pass the barrier to the first phase, and optionally substantially impermeable means configured to prevent the mixing of a first phase and a second phase of the sample (e.g., liquid biological sample, for example, a blood sample) on opposite surfaces of the substantially impermeable seal at least under a set of conditions that one having ordinary skill in the art would recognize as ordinarily causing a gel only barrier to breach (e.g., after vigorous shaking, for example, as one would shake a spray paint can for two minutes);

or any combination thereof.

72. The embodiment, system, method or composition of any preceding clause, optionally wherein the float (i) is made of a single, integral piece or a plurality of pieces that are configured to be fixed and immobile relative to each other during centrifugation, (ii) is solid and without any aperture (e.g., without any aperture in the form of a port, for example, an aperture configured to permit thixotropic material to pass through the float via the aperture, to permit thixotropic material to pass from an inner void of the float to the exterior of the float, to permit a portion of the first phase of the sample to pass the barrier to the second phase of the sample, to permit a portion of the second phase of the sample to pass the barrier to the first phase of the sample, or any combination thereof), without an inner void, or without any combination thereof), (iii) is hollow, having an inner void and having no aperture or port to connect the inner void to the exterior of the float, (iv) is made of a single, integral piece or a plurality of pieces that are all configured to have the same density within +/−10, 9, 8, 7, 6, 5, 4, 3, 2 or 1% of the density of the most dense piece, is made of the same material or materials, or any combination thereof, (v) optionally wherein the float is solid (e.g., solid phase as opposed to being a liquid or gas, in the sense of being filled and not hollow, in the sense of having no apertures configured to allow fluid (e.g., a thixotropic material, for example a gel) to pass from inside the float to outside the float, in the sense of having no apertures configured to allow fluid (e.g., a portion of the first phase, a portion of the second phase, or a combination thereof) to pass from a first surface of the barrier to an opposite surface of the barrier, or any combination thereof), (vi) optionally the float is a single, integral piece, (vii) optionally the float is non-porous, (viii) optionally the float is configured not to deform under any value, range or combination of ranges of relative centrifugal force described in this disclosure, (ix) optionally the float comprises a plurality of mutually spaced protuberances (e.g., ridges), and optionally the protuberances or ridges are longitudinally oriented within 30, 25, 20, 15, 10, 9, 8, 7, 6, 5, 4, 3, 2 or 1 degrees of parallel to a central axis, longitudinal axis, length or combination thereof of the float; or (x) any combination thereof.

73. Any embodiment disclosed in this application.

74. The embodiment, system, method or composition of any preceding clause, wherein (i) the embodiment, system, method, composition or any combination thereof, (ii) any component of (i), or (ii) or any step of (i): (1) comprises any feature or combination of features disclosed in this application, (2) comprises any structure or combination of structures disclosed in this application, (3) comprises any step or combination of steps disclosed in this application, (4) are configured in any manner or for any purpose disclosed in this application, or (5) any combination thereof.

Although some embodiments have been described using the term about to characterize a value, additional embodiments can be created in which the language including the term "about" in association with a value is replaced with "+/−30, 25, 20, 15, 10, 9, 8, 7, 6, 5, 4, 3, 2 or 1%" of the value. Also, additional embodiments can be created by simply deleting the word "about."

Although several embodiments have been described herein using the wording "substantially impermeable" for any embodiment, system, method or composition of described in this disclosure, and additional embodiment can be created optionally wherein substantially impermeable means configured to prevent the mixing of a first phase and a second phase of the sample on opposite surfaces of the substantially impermeable barrier (i) at least when a tubular body, of a set of components comprising (or consisting of) the tubular body, the thixotropic material (e.g., gel), float, first phase and second phase, is stationary and (ii) optionally after the tubular body (containing the thixotropic gel, float, first phase, and second phase) is oscillated about a starting point along a vertical axis at an amplitude of three inches above the starting point and three inches below the starting point at a rate of 1, 2, 3, or 4 complete oscillations per second for 10, 20, 30, 40, 50, 60, 70, 80, 90, 100, 110 or 120 seconds, optionally wherein substantially impermeable means configured so that no more than 3, 2, 1, 0.5, 0.4, 0.3, 0.2 or 0.1 wt. % of material from the first phase is permitted to pass the barrier to the second phase and no more than 3, 2, 1, 0.5, 0.4, 0.3, 0.2 or 0.1 wt. % of material from the second phase is permitted to pass the barrier to the first phase, and optionally substantially impermeable means configured to prevent the mixing of a first phase and a second phase of the sample (e.g., liquid biological sample, for example, a blood sample) on opposite surfaces of the substantially impermeable seal at least under a set of conditions that one having ordinary skill in the art would recognize as ordinarily causing a gel only barrier to breach (e.g., after vigorous shaking, for example, as one would shake a spray paint can for two minutes).

As used herein, longitudinal axis and central axis of an object are used interchangeably and both mean the longest axis of symmetry present in a symmetrical object, which object can be, for example, a tubular body, optionally in the form of a test tube or a float. As used herein, length refers to a distance between two points, a distance along a specific path or axis (e.g., longitudinal axis or axis of symmetry), the distance between the two points that are the furthest apart on the surface of a referenced object, or any combination thereof.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A system for separating components of a liquid biological sample during centrifugation, the system comprising:
   an apparatus comprising:
   a tubular body for receiving the liquid biological sample;
   a thixotropic material positioned along a bottom inner surface of the tubular body; and
   a float that has a specific gravity less than or equal to a specific gravity of the thixotropic material, and is positioned such that a bottom portion of the float is embedded in the thixotropic material, and is configured not to deform during the centrifugation when the centrifugation occurs at a relative centrifugal force of 500 g.

2. The system according to claim 1, wherein the specific gravity of the float is less than the specific gravity of the thixotropic material.

3. The system according to claim 1, wherein the float has a diameter equal to at least 50% of an inner diameter of the tubular body and no more than 99.9% of the inner diameter of the tubular body.

4. The system according to claim 1, wherein the thixotropic material comprises a polymer selected from: a polyester; a polyolefin; a polyacrylate; hydrogenated styrene-butadiene rubber; and a combination of two or more thereof.

5. The system according to claim 1, wherein the float has a shore hardness of from 1 to 50.

6. The system according to claim 1, wherein the specific gravity of the float is from 1.02 to 1.09.

7. The system according to claim 1, wherein the specific gravity of the float is 1.025 to 1.035.

8. The system according to claim 1, wherein the thixotropic material has a density of from 1.02 to 1.09 g/cm$^3$.

9. The system according to claim 1, wherein the float has a surface configured to limit platelet adhesion.

10. The system according to claim 1, wherein the float comprises one or more protuberances.

11. The system according to claim 1, wherein the float comprises a plurality of protuberances.

12. The system according to claim 11, wherein the protuberances are positioned along a surface of the float configured to be adjacent to an inner wall of the tubular body.

13. The system according to claim 10, wherein the protuberances are configured to substantially maintain a central axis of the float along a central axis of the tubular body.

14. The system according to claim 10, wherein the protuberances are equidistantly spaced, laterally, or longitudinally or both, along a surface of the float.

15. The system according to claim 14, wherein the protuberances are equidistantly spaced along a surface of the float adjacent to the inner walls of the tubular body.

16. The system according to any of claim 10, wherein the protuberances comprise a different material than a core of the float.

17. The system according to claim 1, wherein a circle circumscribing radially outermost portions of a bottom surface of the float has a diameter that is at least 0.6 times and up to 1 times a diameter of a circle circumscribing outermost portions at a top surface of the float.

18. The system according to claim 1, wherein the float is substantially cylindrical, wherein the float is deemed to be substantially cylindrical if, after the float is allowed to sink completely into a test fluid that is less dense than the float, a volume of a the test fluid displaced by the float is at least 0.5 times and up to 1 times a volume of a cylinder that circumscribes the float.

19. The system according to claim 1, wherein a top surface of the float has a greater diameter than a bottom surface of the float.

20. The system according to claim 1, wherein the float is bullet-shaped.

21. The system according to claim 1 wherein a portion of the float is claw-shaped.

22. The system according to claim 1, wherein a surface of the float adjacent to the tubular body has a saw-tooth or crenelated pattern.

23. The system according to claim 1, wherein a surface of the float adjacent to the tubular body has a sinusoidal pattern.

24. The system according to claim 1, wherein the float is substantially spherical, wherein the float is substantially spherical if, after the float is allowed to sink completely into a test fluid that is less dense than the float, a volume of the test fluid displaced by the float is at least 0.5 times and up to 1 times a volume of a sphere that circumscribes the float.

25. The system according to claim 1, wherein the float further comprises a cavity.

26. The system according to claim 25, wherein the cavity has a volume greater than 50% of a total volume of the float.

27. The system according to claim 25, wherein the float is tooth-shaped.

28. The system according to claim 1, wherein an inner wall of the tubular body comprises a coating.

29. The system according to claim 28, wherein the coating comprises an inert material.

30. The system according to claim 1, wherein the specific gravity of the float is larger than a specific gravity of a component of the sample with a smallest specific gravity.

31. The system according to claim 1, wherein the thixotropic material has a specific gravity smaller than a specific gravity of a component of the sample with a largest specific gravity.

32. The system according to claim 1, wherein the tubular body contains a vacuum formed in combination with a stopper.

33. The system according to claim 1, wherein an interior of the tubular body is at an absolute pressure between 0 and 1 atm.

34. The system according to claim 1, wherein the float and the thixotropic material are different in color.

35. The system according to claim 1, wherein the float and thixotropic material are releasably coupled.

36. The system according to claim 1, wherein a volume and rheological profile of the thixotropic gel and dimensions of the float are configured to permit density separation of the components of the sample by centrifugation.

37. The system according to claim 1, wherein a volume and rheological profile of the thixotropic gel and dimensions of the float are configured to create a passageway between an outer surface of the float and an inner wall of the tubular body, during centrifugation.

38. The system according to claim 1, wherein a volume and rheological profile of the thixotropic gel and dimensions of the float are configured to create a substantially impermeable seal between a surface of the float adjacent to the tubular body and an inner wall of the tubular body, wherein substantially impermeable means configured to prevent mixing of a first phase and a second phase of the biological sample on opposite surfaces of the substantially impermeable seal at least when a set of components comprising the tubular body, the thixotropic gel, float, first phase and second phase are stationary.

39. The system according to claim 1, wherein a volume and rheological profile of the thixotropic gel and dimensions of the float are configured to create a substantially impermeable seal between a surface of the float adjacent to the tubular body and an inner wall of the tubular body, wherein substantially impermeable means configured to prevent mixing of a first phase and a second phase of the biological sample on opposite surfaces of the substantially impermeable seal at least when a set of components comprising the tubular body, the thixotropic gel, float, first phase and second phase are stationary.

40. The system according to claim 1, wherein a volume and rheological profile of the thixotropic gel and dimensions of the float are configured to create an impermeable seal between a surface of the float adjacent to the tubular body and an inner wall of the tubular body.

41. The system according to claim 1, wherein a volume and rheological profile of the thixotropic gel and dimensions of the float are configured to create an impermeable seal between a surface of the float adjacent to the tubular body and an inner wall of the tubular body, after centrifugation.

42. The system according to claim 1, wherein the thixotropic material has a specific gravity less than a specific gravity of red blood cells.

43. The system according to claim 1, wherein the thixotropic material and the float have a specific gravity greater than a specific gravity of plasma.

44. The system according to claim 1, further comprising an anticoagulant.

45. The system according to claim 44, wherein the anticoagulant is selected from a citrate salt and ethylenediaminetetraacetic acid (EDTA).

46. The system according to claim 1, wherein the apparatus comprises an anticoagulant.

47. The system according to claim 1, wherein the thixotropic material and float remain in a substantially fixed position relative to the tubular body during transport, wherein remaining in the substantially fixed position means that no point on the float and no boundary of the thixotropic material moves along a central axis or length of the tubular body by more than 15, 10, 9, 8, 7, 6, 5, 4, 3, 2 or 1% of a length of the float along a longitudinal axis or the central axis of the float.

48. The system according to claim 1, wherein the float is solid and has no apertures configured to allow fluid to pass from inside the float to outside the float and has no apertures configured to allow fluid to pass from a first surface of the float to an opposite surface of the float.

49. The system according to claim 1, wherein the float is a single, integral piece or a plurality of pieces that are configured to be fixed and immobile relative to each other during centrifugation.

50. The system according to claim 1, wherein the sample comprises blood.

51. The system according to claim 1, wherein at least a portion of a top surface of the float is situated above the thixotropic material, after centrifugation.

52. The system according to claim 1, wherein a top surface of the float is situated above the thixotropic material, after centrifugation.

53. The system according to claim 1, wherein the float is configured not to deform during the centrifugation when the centrifugation occurs at a relative centrifugal force of 1750 g.

54. A method for preparing platelet rich plasma, using a system for separating components of a liquid biological sample during centrifugation, the method comprising:
providing a system for separating components of a liquid biological sample during centrifugation, the system comprising:
an apparatus comprising:
a tubular body for receiving the liquid biological sample, which is a blood sample;
a thixotropic material positioned along a bottom inner surface of the tubular body; and
a float that has a specific gravity less than or equal to the specific gravity of the thixotropic material, is positioned such that a bottom portion of the float is embedded in the thixotropic material, and is configured not to deform during the centrifugation when the centrifugation occurs at a relative centrifugal force of 500 g;
centrifuging the apparatus for a time and speed sufficient to separate the components of the blood sample into a first phase and a second phase, wherein the first phase comprises red blood cells and the second phase comprises plasma; and
removing a portion of the second phase to provide the platelet rich plasma.

55. The method according to claim 54, wherein the portion removed from the second phase comprises platelet poor plasma.

56. The method according to claim 54, further comprising agitating the platelet rich plasma.

57. The method according to claim 54, wherein the float and the thixotropic material are maintained at equilibrium between the first phase and the second phase.

* * * * *